United States Patent
Kim et al.

(10) Patent No.: US 9,991,452 B2
(45) Date of Patent: Jun. 5, 2018

(54) CONDENSED-CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Sooyon Kim, Yongin (KR); Kwanghyun Kim, Yongin (KR); Youngkook Kim, Yongin (KR); Sanghyun Han, Yongin (KR); Seokhwan Hwang, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 318 days.

(21) Appl. No.: 14/731,641

(22) Filed: Jun. 5, 2015

(65) Prior Publication Data

US 2016/0190448 A1 Jun. 30, 2016

(30) Foreign Application Priority Data

Dec. 30, 2014 (KR) .......................... 10-2014-0194328

(51) Int. Cl.
*H01L 51/00* (2006.01)
*C09K 11/06* (2006.01)
(Continued)

(52) U.S. Cl.
CPC ............ *H01L 51/008* (2013.01); *C07F 5/027* (2013.01); *C07F 7/082* (2013.01); *C07F 7/0812* (2013.01);
(Continued)

(58) Field of Classification Search
CPC ............... H01L 51/008; H01L 51/0052; H01L 51/0054; H01L 51/0058; H01L 51/006;
(Continued)

(56) References Cited

U.S. PATENT DOCUMENTS

2003/0152800 A1  8/2003  Tamao et al.
2003/0157366 A1  8/2003  Matsuura et al.
(Continued)

FOREIGN PATENT DOCUMENTS

EP    1142895 A1    10/2001
JP    2000-294373   10/2000
(Continued)

OTHER PUBLICATIONS

Provisional double patenting rejection over claims of the above-identified application; USPTO Office action dated Oct. 12, 2017, in U.S. Appl. No. 14/743,217.

*Primary Examiner* — Ruiyun Zhang
(74) *Attorney, Agent, or Firm* — Lee & Morse, P.C.

(57) ABSTRACT

A condensed-cyclic compound is represented by Formula 1:

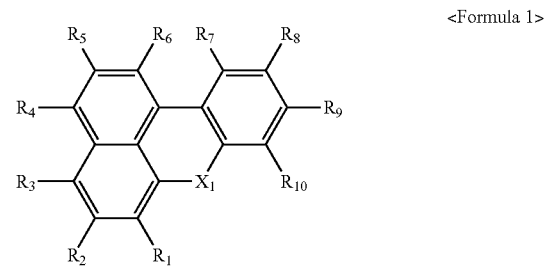

<Formula 1> where $X_1$ and $R_1$ to $R_{10}$ are as defined in the specification, and at least one of $R_1$ to $R_{10}$ is a group represented by Formula 2, and at least one of $R_1$ to $R_{10}$ is a group represented by Formula 3:

(Continued)

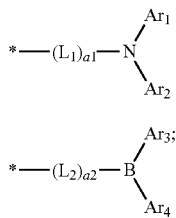

<Formula 2>

<Formula 3> where $L_1$, $L_2$, $Ar_1$ to $Ar_4$, a1 and a2 are as defined in the specification.

20 Claims, 1 Drawing Sheet

(51) Int. Cl.
*C07F 5/02* (2006.01)
*C07F 7/08* (2006.01)
*C09K 11/02* (2006.01)
*H01L 51/50* (2006.01)

(52) U.S. Cl.
CPC ............ *C09K 11/025* (2013.01); *C09K 11/06* (2013.01); *H01L 51/006* (2013.01); *H01L 51/0058* (2013.01); *H01L 51/0061* (2013.01); *H01L 51/0073* (2013.01); *C09K 2211/1007* (2013.01); *C09K 2211/1011* (2013.01); *C09K 2211/1014* (2013.01); *C09K 2211/1022* (2013.01); *C09K 2211/1088* (2013.01); *C09K 2211/1092* (2013.01); *H01L 51/5012* (2013.01)

(58) Field of Classification Search
CPC ............. H01L 51/0061; H01L 51/0073; H01L 51/5012; C07F 5/027; C07F 7/0812; C07F 7/082; C09K 11/025; C09K 11/06; C09K 2211/1011; C09K 2211/1014; C09K 2211/1022; C09K 2211/1088; C09K 2211/1092
USPC .................. 428/690, 917; 252/301.16; 568/1
See application file for complete search history.

(56) References Cited

U.S. PATENT DOCUMENTS

| | | |
|---|---|---|
| 2007/0237984 A1 | 10/2007 | Matsuura et al. |
| 2009/0004485 A1 | 1/2009 | Zheng et al. |
| 2010/0052526 A1 | 3/2010 | Je et al. |
| 2010/0277061 A1 | 11/2010 | Matsuura et al. |
| 2012/0056165 A1 | 3/2012 | Kawamura et al. |
| 2013/0306958 A1 | 11/2013 | Ito et al. |
| 2014/0346482 A1 | 11/2014 | Mizuki et al. |
| 2014/0361266 A1* | 12/2014 | Jung ................... H01L 51/0094 257/40 |

FOREIGN PATENT DOCUMENTS

| | | |
|---|---|---|
| JP | 2003-234192 | 8/2003 |
| JP | 2007-119454 | 5/2007 |
| JP | 2007-123863 | 5/2007 |
| JP | 2008-280331 | 11/2008 |
| JP | 4221050 | 11/2008 |
| JP | 2013-63930 | 4/2013 |
| JP | 2013-63931 | 4/2013 |
| KR | 10-2011-0015213 A | 2/2011 |
| KR | 10-2011-0094271 | 8/2011 |
| KR | 10-1132635 | 3/2012 |
| KR | 10-2014-0032948 | 3/2014 |

* cited by examiner

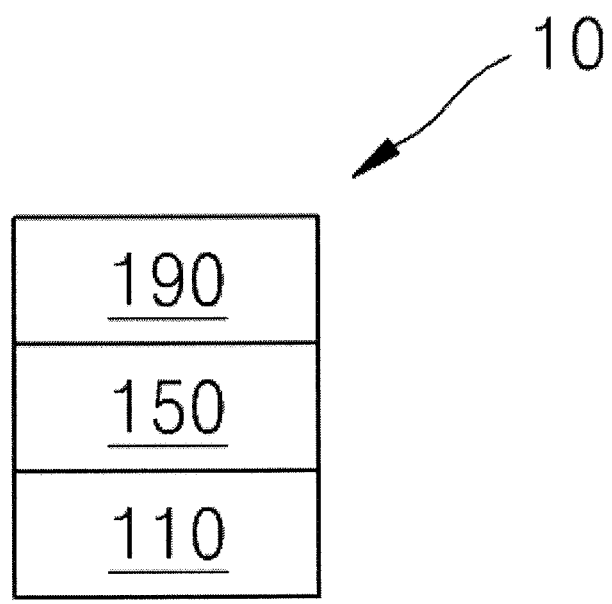

CONDENSED-CYCLIC COMPOUND AND ORGANIC LIGHT-EMITTING DEVICE INCLUDING THE SAME

CROSS-REFERENCE TO RELATED APPLICATION

Korean Patent Application No. 10-2014-0194328, filed on Dec. 30, 2014, in the Korean Intellectual Property Office, and entitled: "Condensed-Cyclic Compound and Organic Light-Emitting Device Including the Same," is incorporated by reference herein in its entirety.

BACKGROUND

1. Field

Embodiments relate to a condensed-cyclic compound and an organic light-emitting device including the same.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. The holes and the electrons are recombined in the emission layer to produce excitons. These excitons change from an excited state to a ground state to thereby generate light.

SUMMARY

Embodiments are directed to a condensed-cyclic compound is represented by Formula 1:

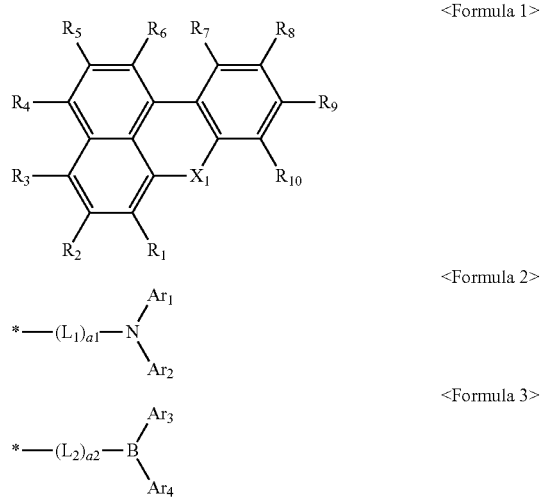

<Formula 1>

<Formula 2>

<Formula 3> wherein, in Formulae 1 to 3, $X_1$ is selected from O, S, N-$(L_3)_{a3}$-$(Ar_5)$, and Si$(R_{11})$$(R_{12})$;

$L_1$ to $L_3$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group:

a1 to a3 are each independently selected from 0, 1, 2, and 3; when a1 is 2 or greater, two or more $L_1$s are identical to or different from each other, when a2 is 2 or greater, two or more $L_2$s are identical to or different from each other, and, when a3 is 2 or greater, two or more $L_2$s are identical to or different from each other;

$Ar_1$ to $Ar_5$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_1$ to $R_{12}$ are each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si$(Q_1)(Q_2)(Q_3)$;

at least one of $R_1$ to $R_{10}$ is a group represented by Formula 2, and at least one of $R_1$ to $R_{10}$ is a group represented by Formula 3;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more exemplary embodiments, an organic light-emitting device includes a first electrode; a second electrode facing the first electrode; and an organic layer that is disposed between the first electrode and the second electrode and comprises an emission layer, wherein the organic layer comprises at least one type of the condensed-cyclic compound.

BRIEF DESCRIPTION OF THE DRAWING

Features will become apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

A condensed-cyclic compound is represented by Formula 1:

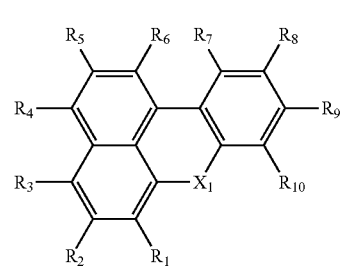

<Formula 1>

In Formula 1, $X_1$ may be selected from O, S, N-($L_3$)$_{a3}$-(Ar$_5$), and Si($R_{11}$)($R_{12}$). In some embodiments, $X_1$ may be O.

In Formula 1, $R_1$ to $R_{12}$ may be each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

In Formula 1, at least one of $R_1$ to $R_{10}$ is a group represented by Formula 2, and at least one of $R_1$ to $R_{10}$ is a group represented by Formula 3.

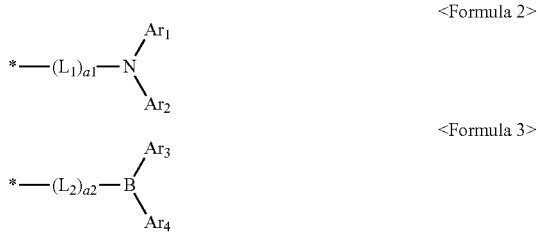

In Formulae 1 to 3, $L_1$ to $L_3$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in Formulae 1 to 3, $L_1$ to $L_3$ may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, in Formulae 1 to 3, $L_1$ to $L_3$ are each independently selected from groups represented by Formulae 3-1 to 3-35:

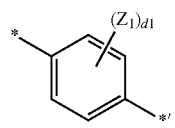

Formula 3-1

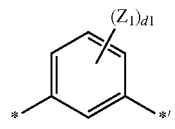

Formula 3-2

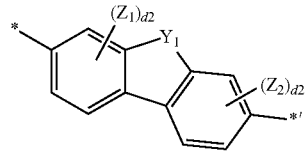

Formula 3-3

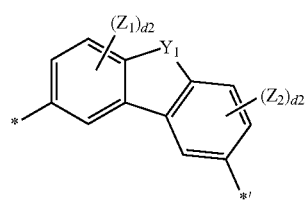

Formula 3-4

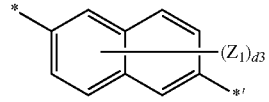

Formula 3-5

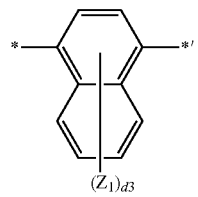

Formula 3-6

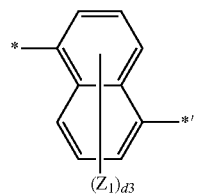

Formula 3-7

-continued

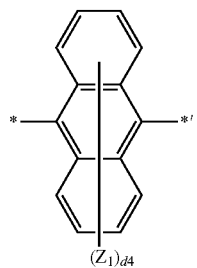

Formula 3-8

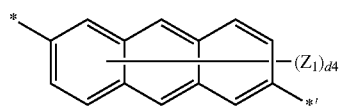

Formula 3-9

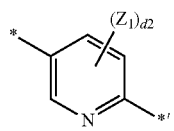

Formula 3-10

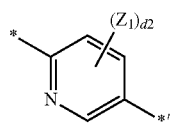

Formula 3-11

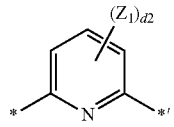

Formula 3-12

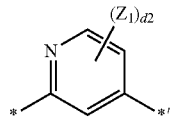

Formula 3-13

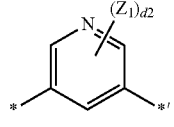

Formula 3-14

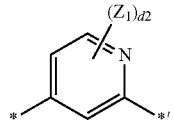

Formula 3-15

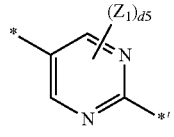

Formula 3-16

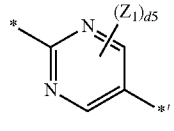

Formula 3-17

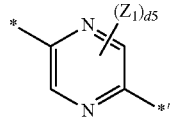

Formula 3-18

-continued

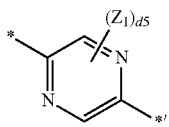
Formula 3-19

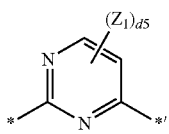
Formula 3-20

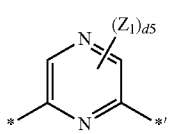
Formula 3-21

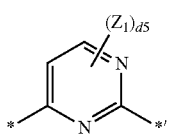
Formula 3-22

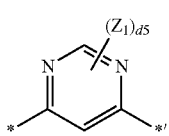
Formula 3-23

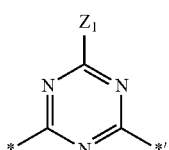
Formula 3-24

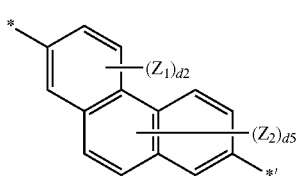
Formula 3-25

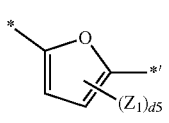
Formula 3-26

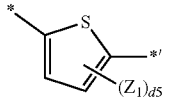
Formula 3-27

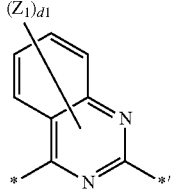
Formula 3-28

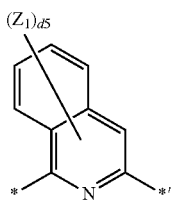
Formula 3-29

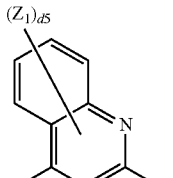
Formula 3-30

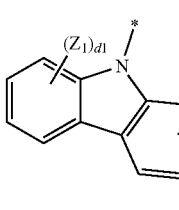
Formula 3-31

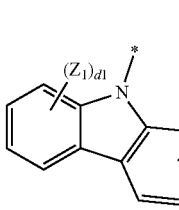
Formula 3-32

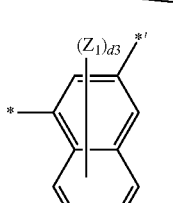
Formula 3-33

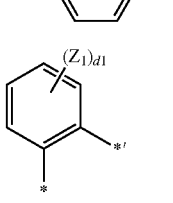
Formula 3-34

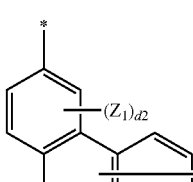
Formula 3-35

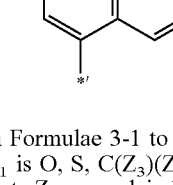

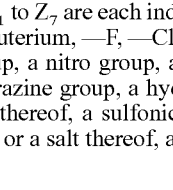

In Formulae 3-1 to 3-35, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

d1 is an integer selected from 1 to 4, d2 is an integer selected from 1 to 3, d3 is an integer selected from 1 to 6, d4 is an integer selected from 1 to 8, d5 is an integer of 1 or 2, d6 is an integer selected from 1 to 5, and * and *' are a binding site to a neighboring atom.

In another embodiment, in Formulae 2 and 2, $L_1$ to $L_3$ may be each independently selected from:

a phenylene group, a naphthylene group, a pyridinylene group, a dibenzofuranylene group, and a dibenzothiophenylene group; and a phenylene group, a naphthylene group, a pyridinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a phenyl group, a naphthyl group, a pyridinyl group, a pyrimidinyl group, and a triazinyl group.

In another embodiment, in Formulae 1 to 3, $L_1$ to $L_3$ may be each independently selected from groups represented by Formulae 4-1 to 4-29:

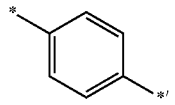

Formula 4-1

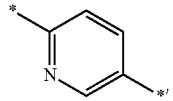

Formula 4-2

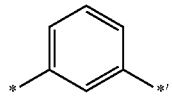

Formula 4-3

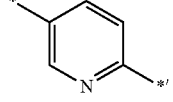

Formula 4-4

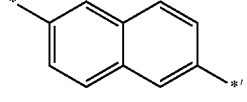

Formula 4-5

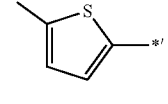

Formula 4-6

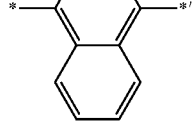

Formula 4-7

-continued

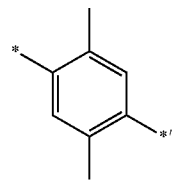

Formula 4-8

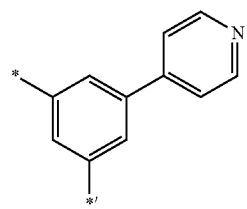

Formula 4-9

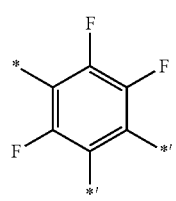

Formula 4-10

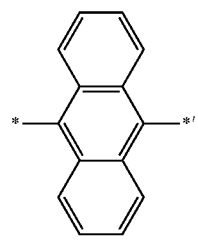

Formula 4-11

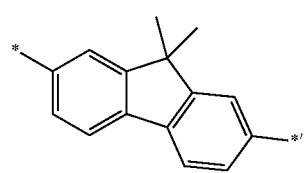

Formula 4-12

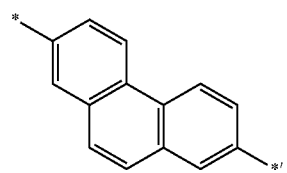

Formula 4-13

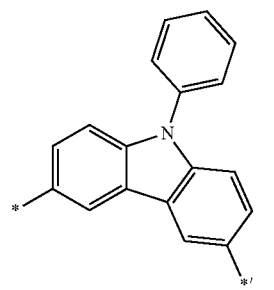

Formula 4-14

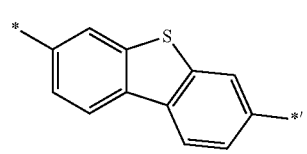

Formula 4-15

-continued

Formula 4-16
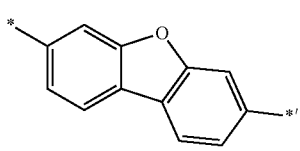

Formula 4-17
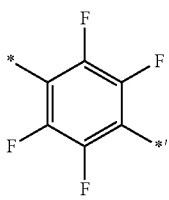

Formula 4-18
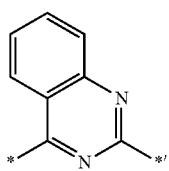

Formula 4-19
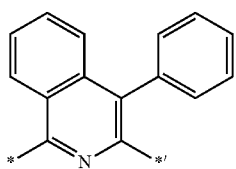

Formula 4-20
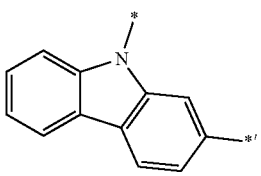

Formula 4-21
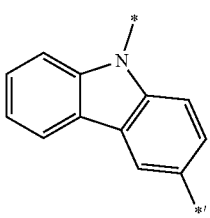

Formula 4-22
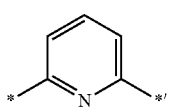

Formula 4-23
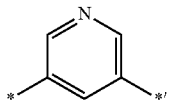

Formula 4-24
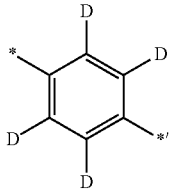

Formula 4-25
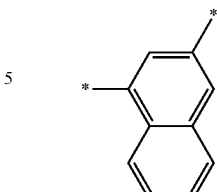

Formula 4-26
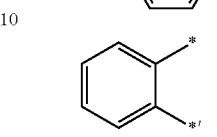

Formula 4-27
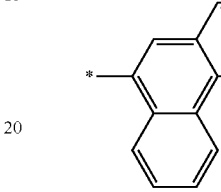

Formula 4-28
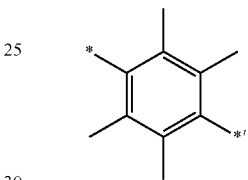

Formula 4-29
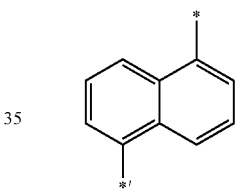

In Formulae 4-1 to 4-29, * and *' are a binding site to a neighboring atom.

In Formulae 1 to 3, a1, a2, and a3 may be each independently selected from 0, 1, 2, and 3. In Formula 2, a1 denotes the number of $L_1$, and, when a1 is 2 or greater, two or more $L_1$s may be identical to or different from each other. For example, when a1 is 0, *-$(L_1)_{a1}$-*' is a single bond. In Formula 3, a2 denotes the number of $L_2$, and, when a2 is 2 or greater, two or more $L_2$s may be identical to or different from each other. For example, when a2 is 0, *-$(L_2)_{a2}$-*' is a single bond. In Formula 1, a3 denotes the number of $L_3$, and, when a3 is 2 or greater, two or more $L_3$s may be identical to or different from each other. For example, when a3 is 0, *-$(L_3)_{a3}$-*' is a single bond. In some embodiments, a1, a2, and a3 may be each independently 0, 1, or 2. In some embodiments, a1, a2, and a3 may be each independently 0 or 1.

In Formulae 2 and 3, $Ar_1$ to $Ar_4$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 1 to 3, $Ar_1$ to $Ar_5$ may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

In another embodiment, in Formulae 1 to 3, $Ar_1$ to $Ar_5$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

In some embodiments, in Formulae 1 to 3, $Ar_1$ to $Ar_5$ may be each independently selected from:

a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

In Formula 1, $R_1$ to $R_{10}$ may be each independently selected from:

a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

In some embodiments, in Formula 1, $R_1$ to $R_{10}$ may be each independently selected from:

a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

In some embodiments, $R_{11}$ and $R_{12}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group; and a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$)

In some embodiments, in Formulae 1 to 3, $Ar_1$ to $Ar_5$ may be each independently selected from groups represented by Formulae 5-1 to 5-43, and $R_1$ to $R_{10}$ may be each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-43, wherein $Q_1$ to $Q_3$ are each independently selected from a $C_1$-$C_{10}$ alkyl group, a $C_1$-$C_{10}$ alkoxy group, a phenyl group, and a naphthyl group:

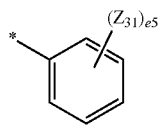

Formula 5-1

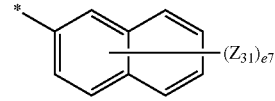

Formula 5-2

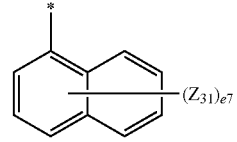

Formula 5-3

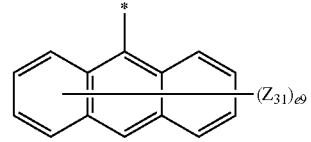

Formula 5-4

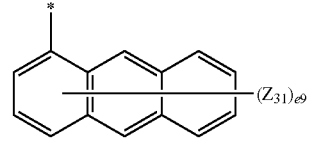

Formula 5-5

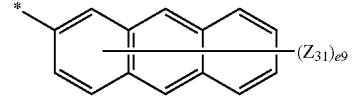

Formula 5-6

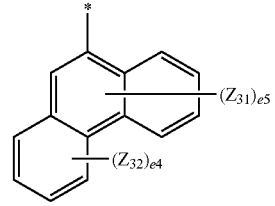

Formula 5-7

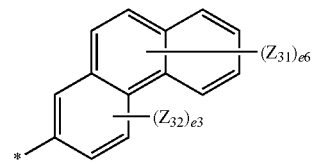

Formula 5-8

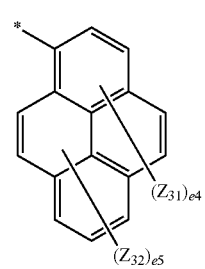

Formula 5-9

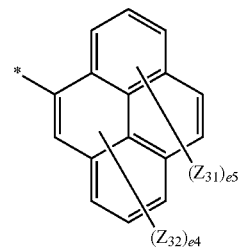

Formula 5-10

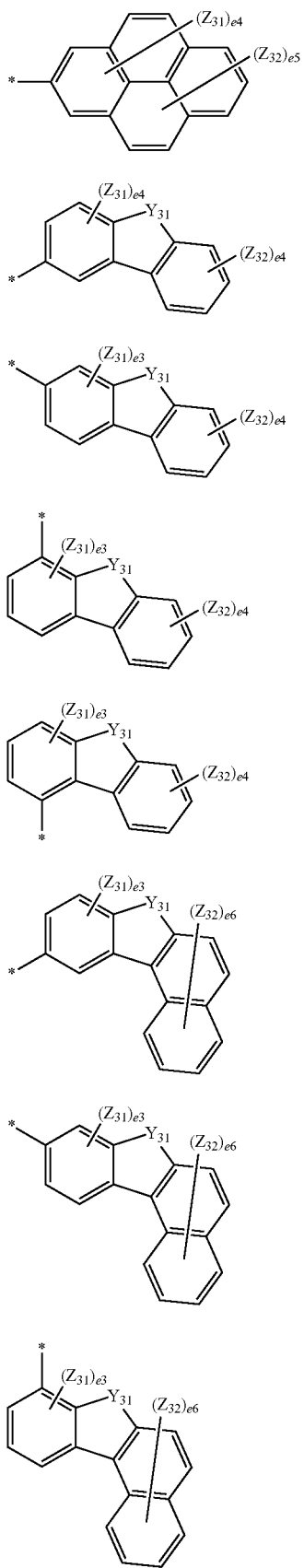
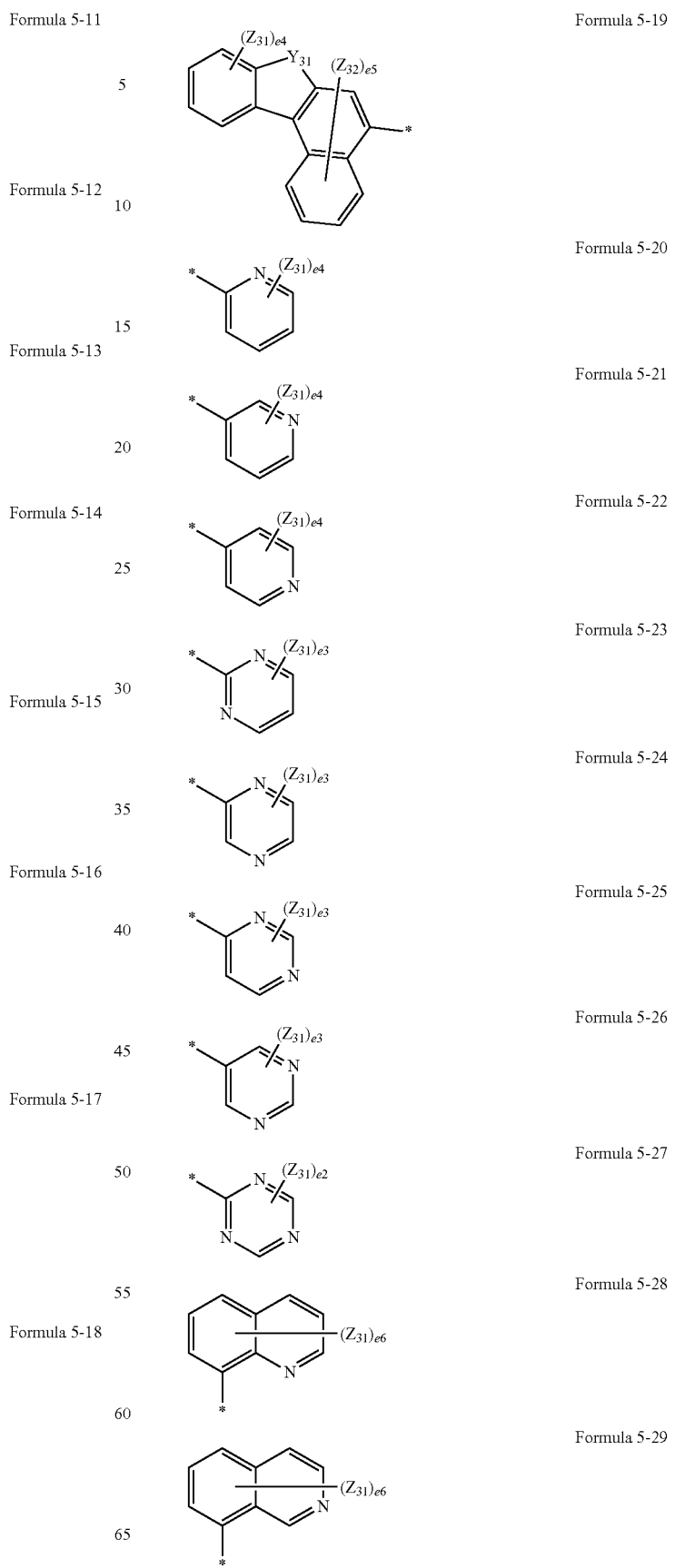

-continued

Formula 5-30 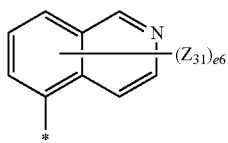

Formula 5-31 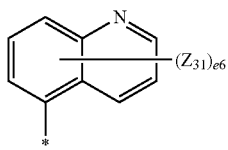

Formula 5-32 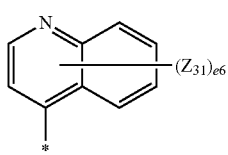

Formula 5-33 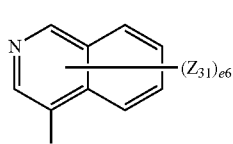

Formula 5-34 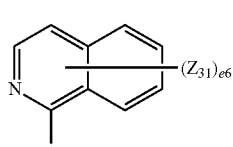

Formula 5-35 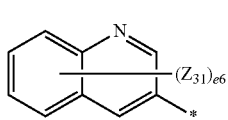

Formula 5-36 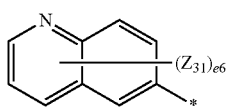

Formula 5-37 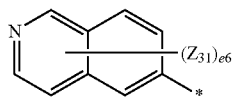

Formula 5-38 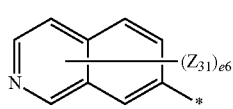

Formula 5-39 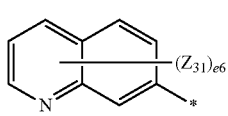

Formula 5-40 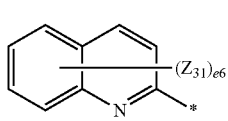

Formula 5-41 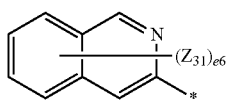

Formula 5-42 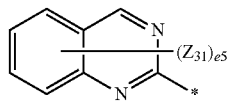

Formula 5-43 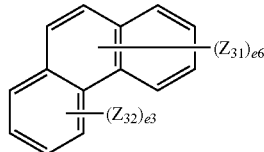

In Formulae 5-1 to 5-43, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e2 is an integer of 1 or 2, e3 is an integer selected from 1 to 3, e4 is an integer selected from 1 to 4, e5 is an integer selected from 1 to 5, e6 is an integer selected from 1 to 6, e7 is an integer selected from 1 to 7, e8 is an integer selected from 1 to 8, e9 is an integer selected from 1 to 9, and * is a binding site to a neighboring atom.

In another embodiment, in Formulae 1 to 3, $Ar_1$ to $Ar_5$ may be each independently selected from groups represented by Formulae 6-1 to 6-40, and $R_1$ to $R_{10}$ may be each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{20}$ alkoxy group, —$Si(Q_1)(Q_2)(Q_3)$, a phenyl group, a naphthyl group, a pyridinyl group, a pyrimidinyl group, and a triazinyl group, wherein $Q_1$ to $Q_3$ are each independently selected from a $C_1$-$C_{10}$ alkyl group, a $C_1$-$C_{10}$ alkoxy group, a phenyl group, and a naphthyl group:

Formula 6-1 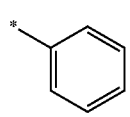

Formula 6-2 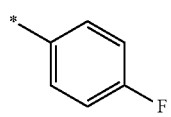

Formula 6-3
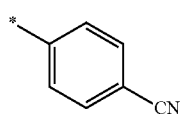
Formula 6-4
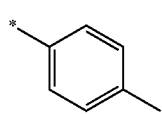
Formula 6-5
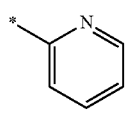
Formula 6-6
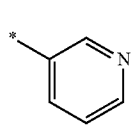
Formula 6-7
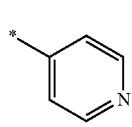
Formula 6-8
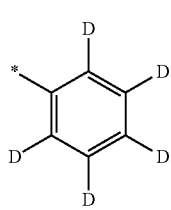
Formula 6-9
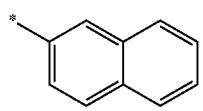
Formula 6-10
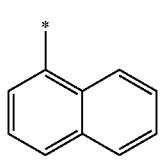
Formula 6-11
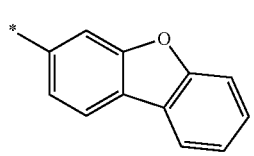
Formula 6-12
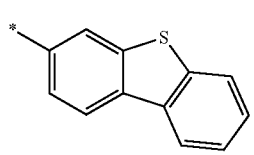
Formula 6-13
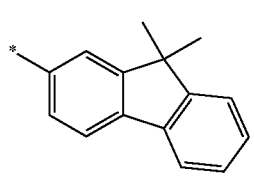
Formula 6-14
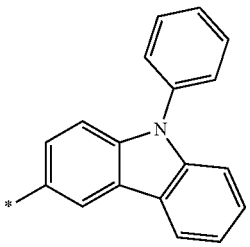
Formula 6-15
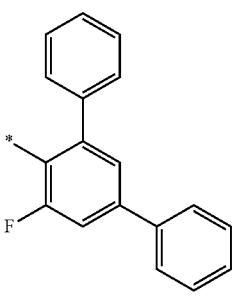
Formula 6-16
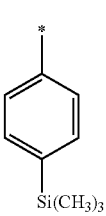
Formula 6-17
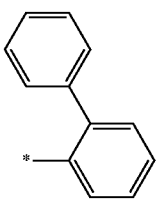
Formula 6-18
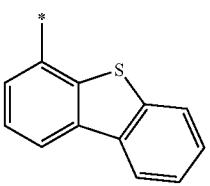
Formula 6-19
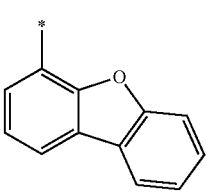
Formula 6-20

-continued
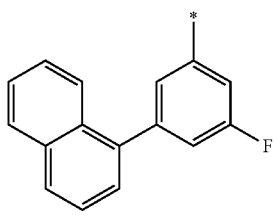
Formula 6-21
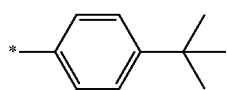
Formula 6-22
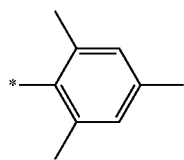
Formula 6-23
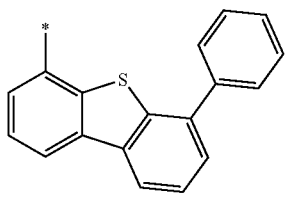
Formula 6-24
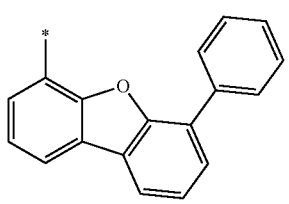
Formula 6-25
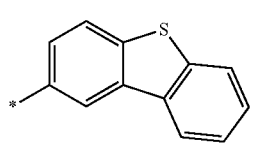
Formula 6-26
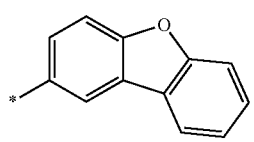
Formlula 6-27
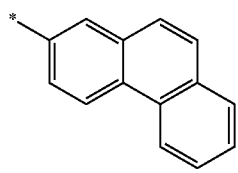
Formula 6-28
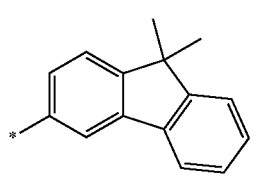
Formula 6-29
-continued
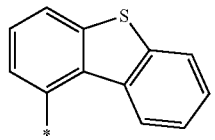
Formula 6-30
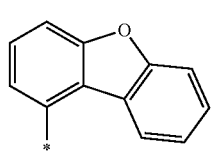
Formula 6-31
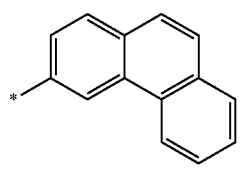
Formula 6-32
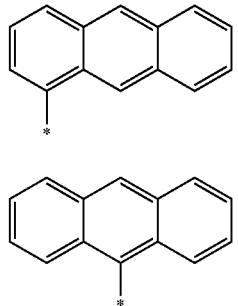
Formula 6-33
Formula 6-34
Formula 6-35
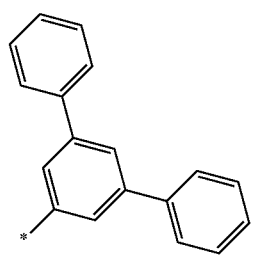
Formula 6-36
Formula 6-37
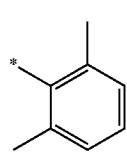
Formula 6-38

-continued

Formula 6-39

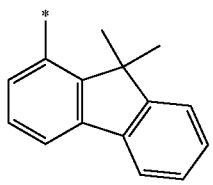

Formula 6-40

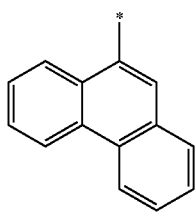

In Formulae 6-1 to 6-40, * is a binding site to a neighboring atom.

In Formula 1, two substituents of $R_1$ to $R_{10}$ may be each selected from a group represented by Formula 2 and a group represented by Formula 3.

In some embodiments, the condensed-cyclic compound represented by Formula 1 may be represented by one of Formulae 1-1 to 1-6:

<Formula 1-1>

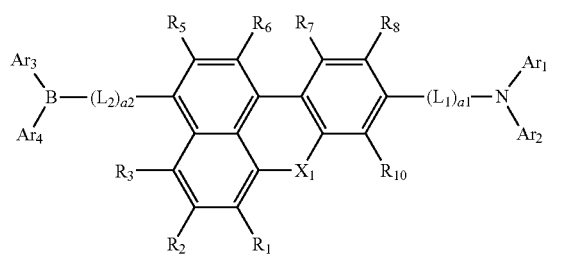

<Formula 1-2>

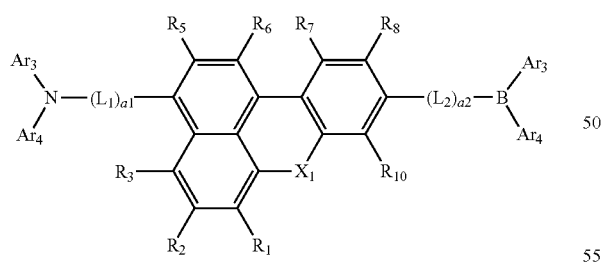

<Formula 1-3>

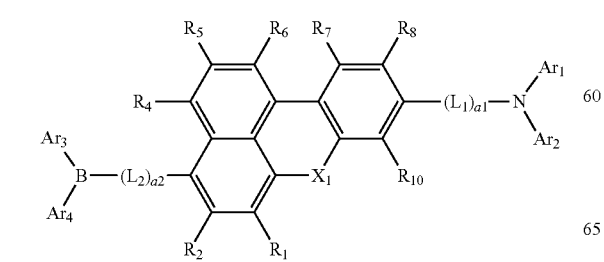

<Formula 1-4>

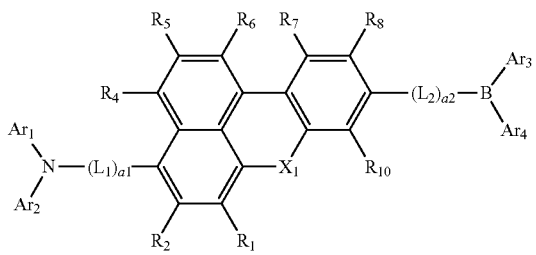

<Formula 1-5>

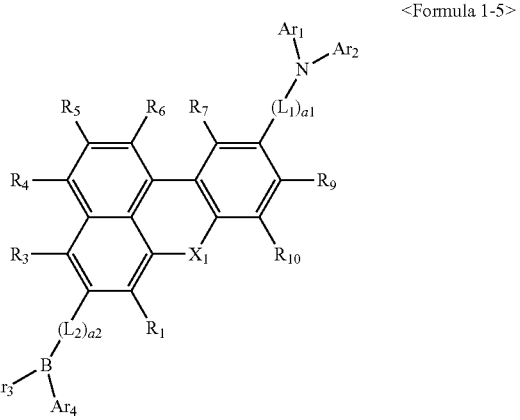

<Formula 1-6>

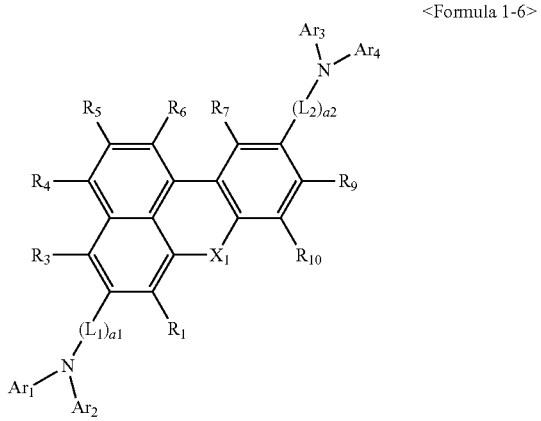

In Formulae 1-1 to 1-6, $X_1$, $L_1$ to $L_3$, a1 to a3, $Ar_1$ to $Ar_5$, and $R_1$ to $R_{12}$ may be each the same as defined herein.

In some embodiments, in Formulae 1-1 to 1-6,
both a1 and a2 may each be 0;
a1 may be 0, and a2 may be 1 or 2;
a1 may be 1 or 2, and a2 may be 0;
both a1 and a2 may each be 1;
a1 may be 1, and a2 may be 2;
a1 may be 2, and a2 may be 1; or
both a1 and a2 may each be 2.

In some embodiments, in Formulae 1-1 to 1-6.
both a1 and a2 may each be 0;
a1 may be 0, and a2 may be 1;
a1 may be 1, and a2 may be 0; or
both a1 and a2 may each be 1.

In some embodiments, in Formulae 1-1 to 1-6,
$Ar_1=Ar_2=Ar_3=Ar_4$;
$Ar_1=Ar_3$, $Ar_2=Ar_4$, and $Ar_2 \neq Ar_3$;
$Ar_1=Ar_3$, $Ar_2 \neq Ar_4$, and $Ar_2 \neq Ar_3$; or
$Ar_1 \neq Ar_2 \neq Ar_3 \neq Ar_4$.

In some embodiments, the condensed-cyclic compound represented by Formula 1 may be represented by one of Formulae 1-1(A) to 1-1(D):

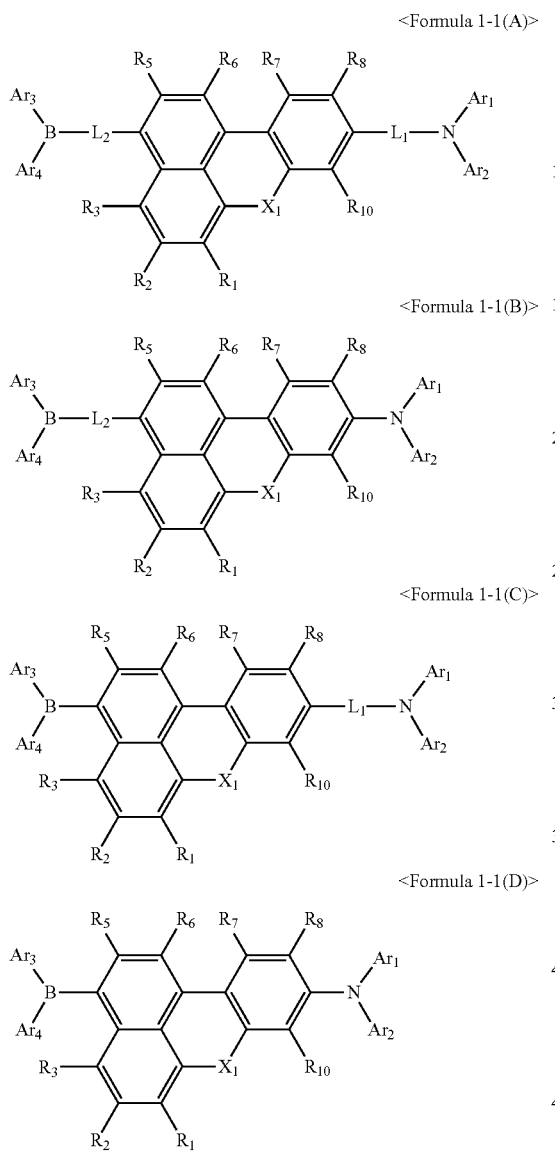

In Formulae 1-1(A) to 1-1(D), $X_1$ may be O or S, $L_1$ and $L_2$ may be each independently selected from a phenylene group, a naphthylene group, a pyridinylene group, a pyrimidinylene group and a triazinylene group; and a phenylene group, a naphthylene group, a pyridinylene group, a pyrimidinylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $Ar_1$ to $Ar_4$ may be each independently selected from groups represented by Formulae 5-1 to 5-43, $R_1$ to $R_3$, $R_5$ to $R_8$, and $R_{10}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group.

In some embodiments, $R_1$ to $R_3$, $R_5$ to $R_8$, and $R_{10}$ may be each independently a hydrogen.

For example, the condensed-cyclic compound represented by Formula 1 may be one of Compounds 1 to 100:

1

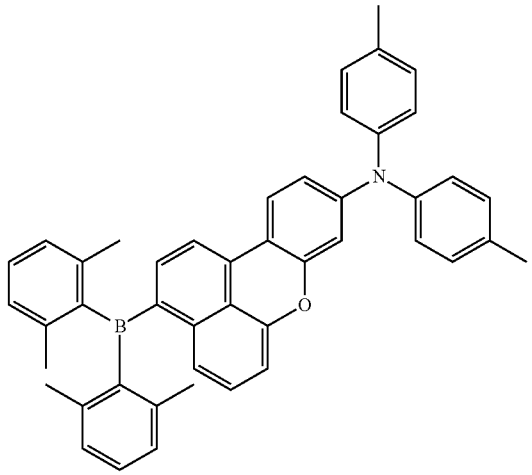

2

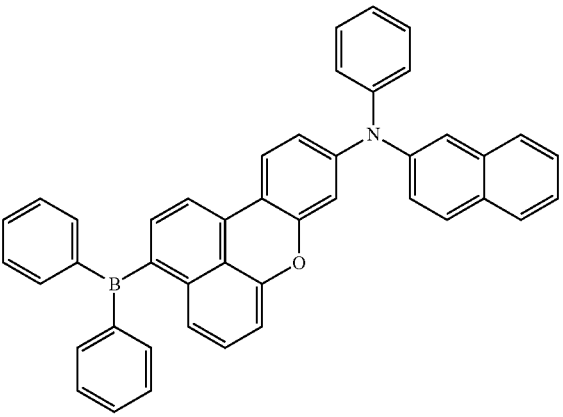

3

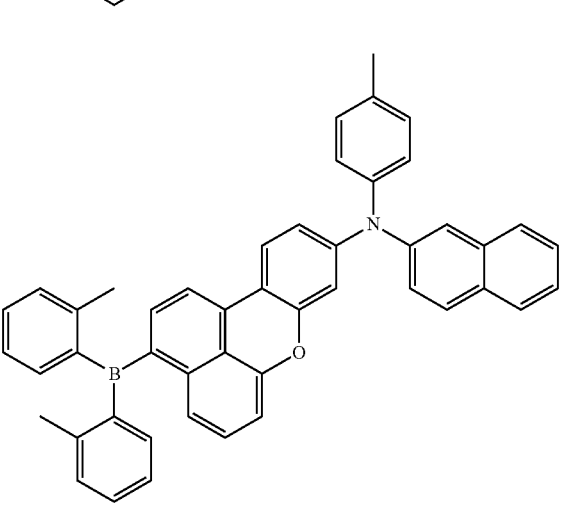

4
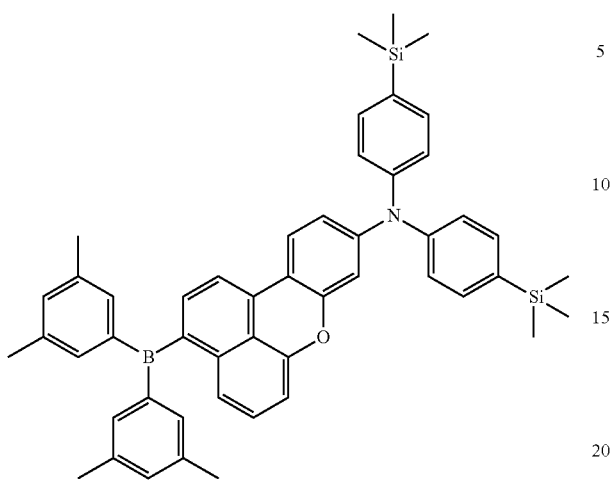
5
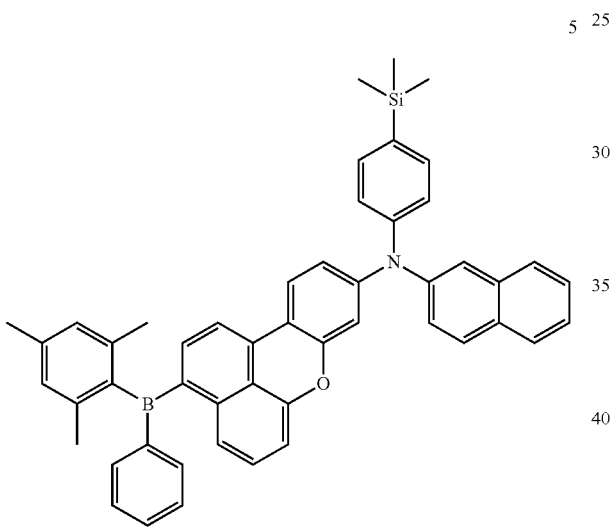
6
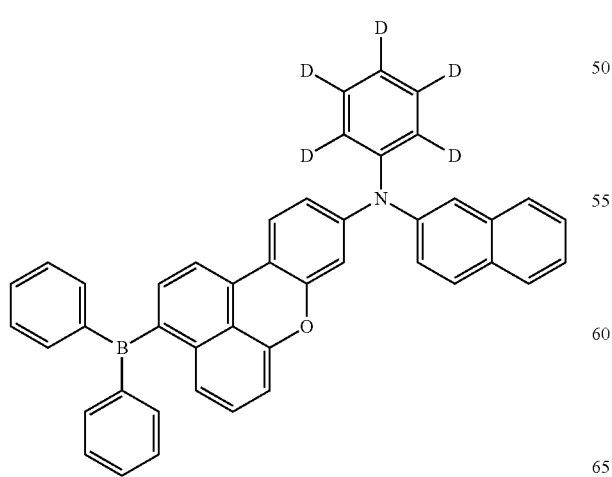
7
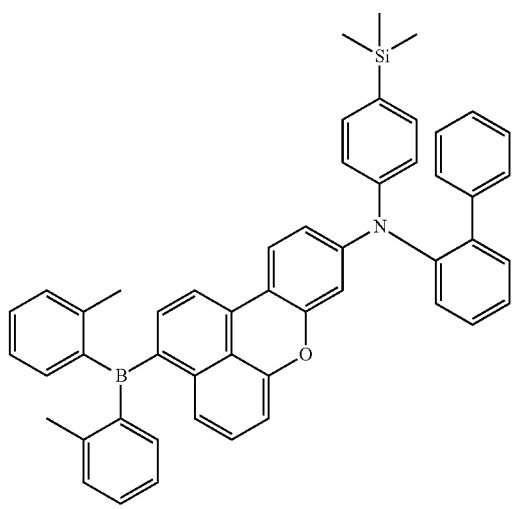
8
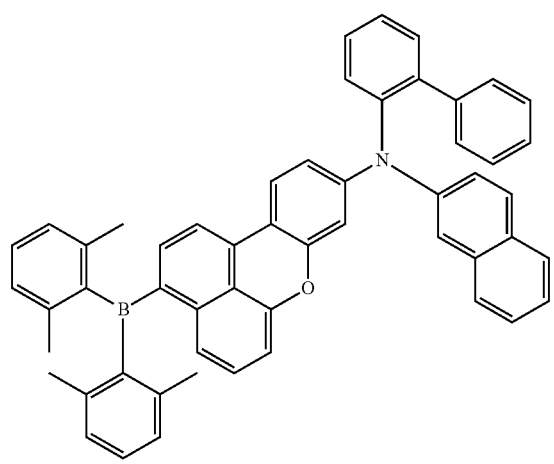
9
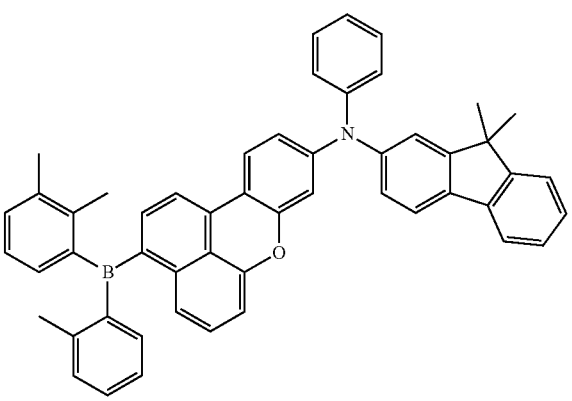

10
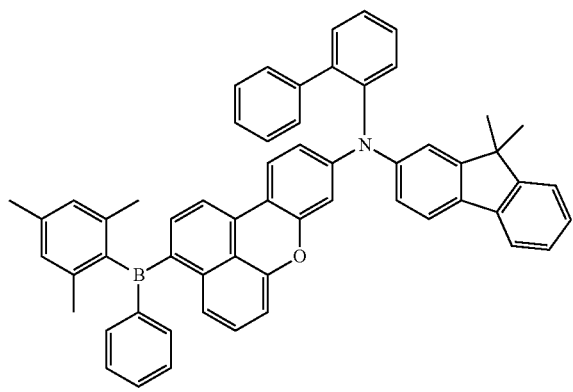
11
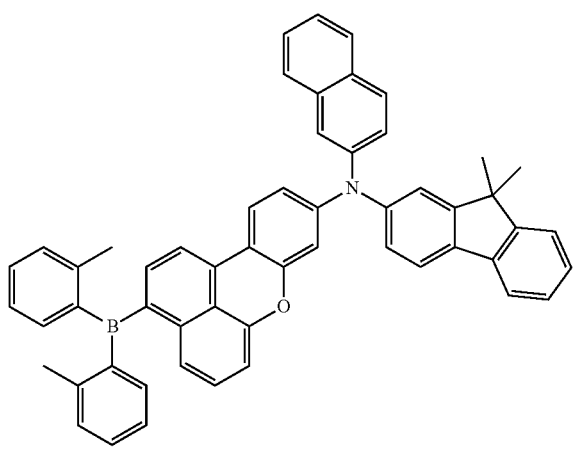
12
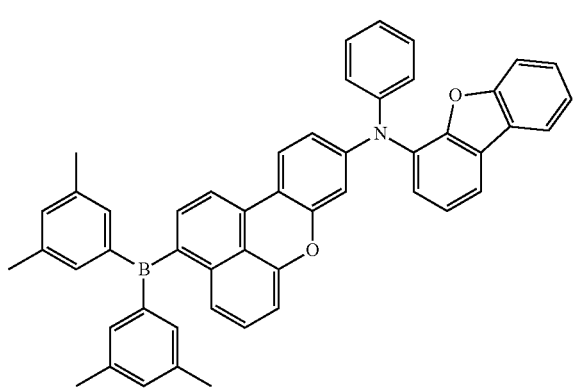
13
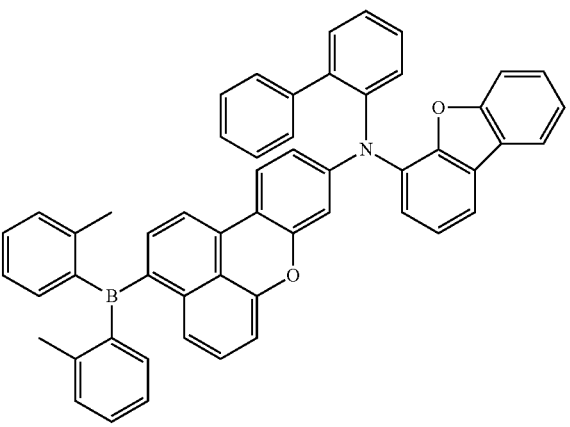
14
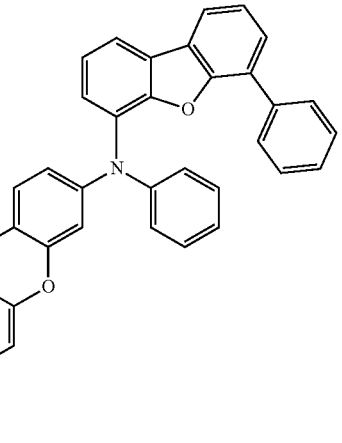
15

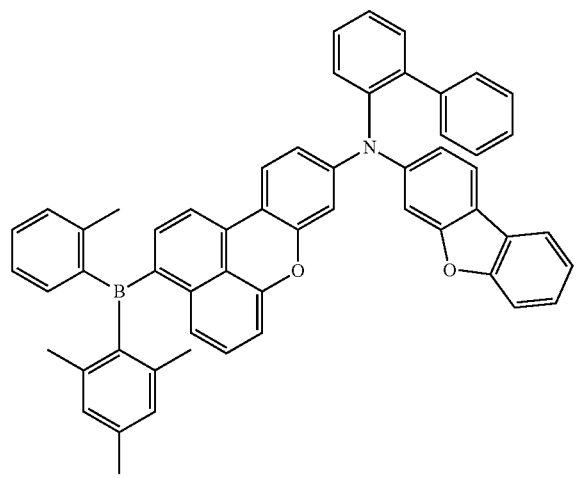
16
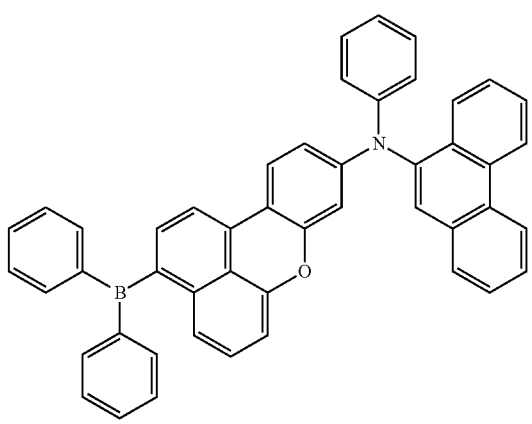
19
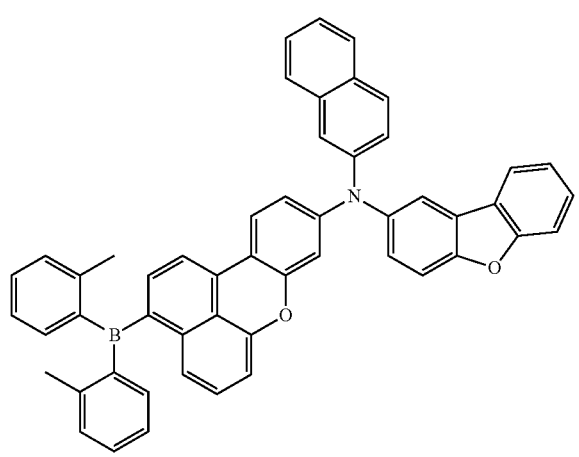
17
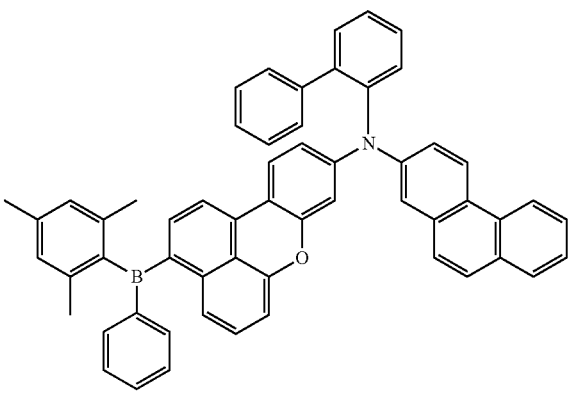
20
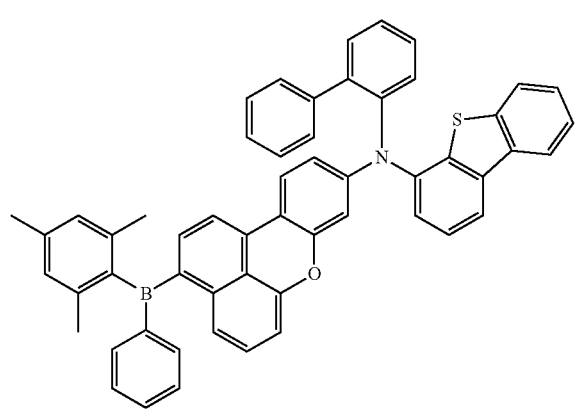
18
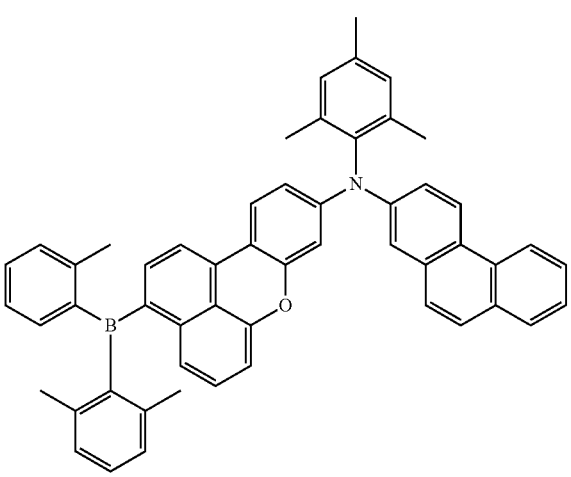
21

22
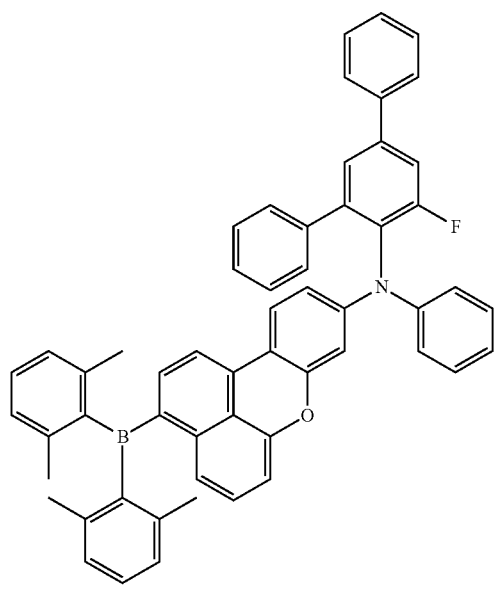
23
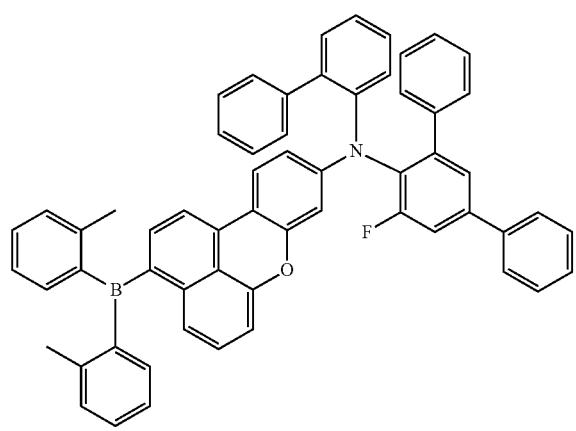
24
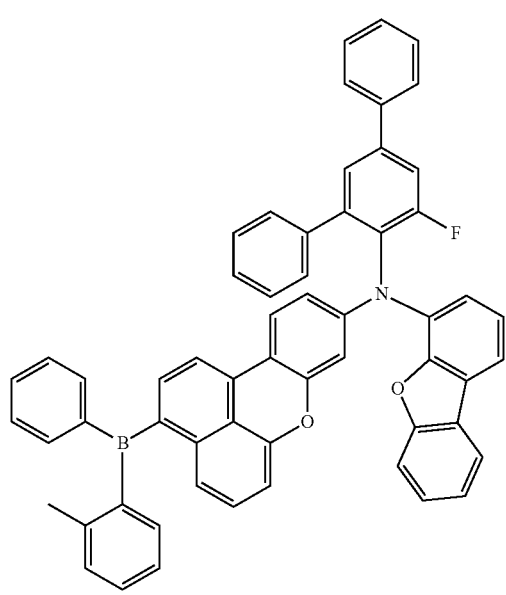
25
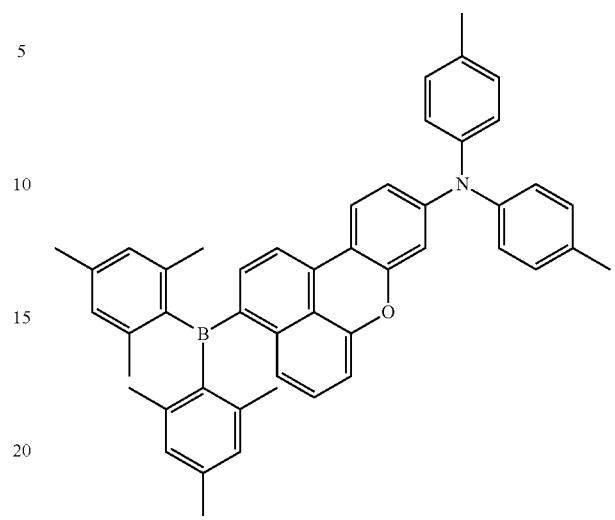
26
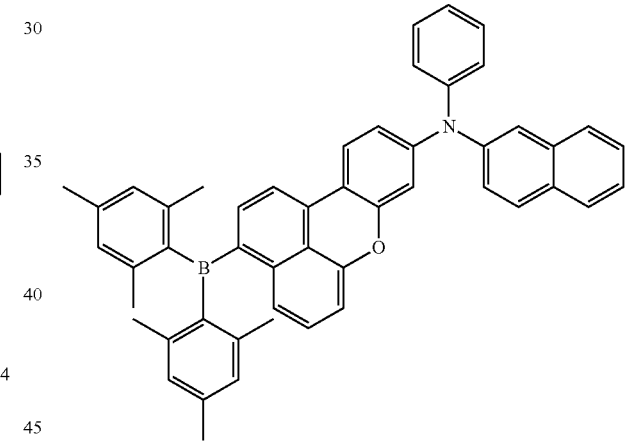
27
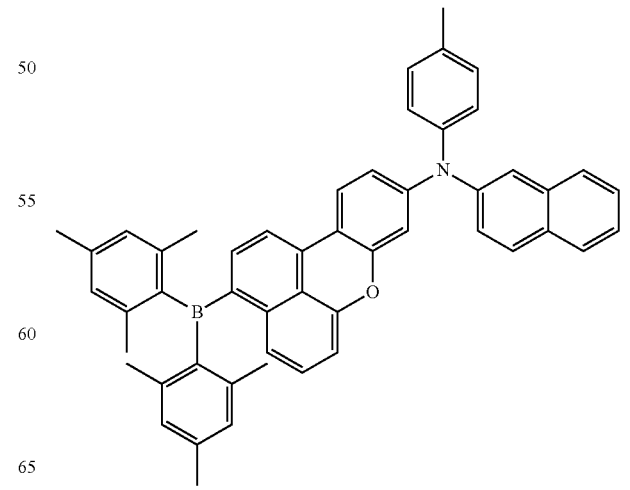

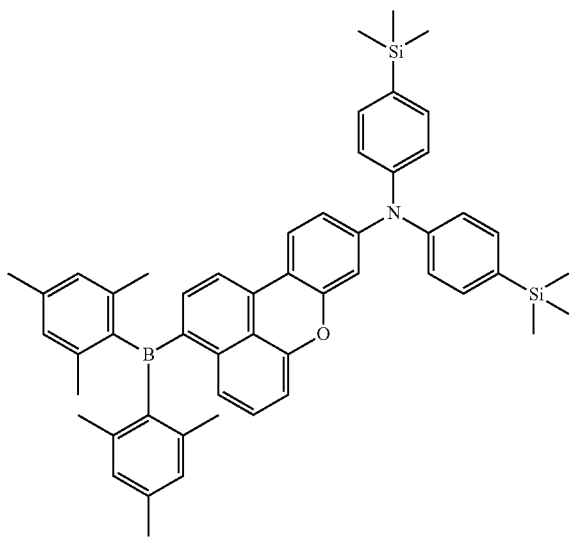
28
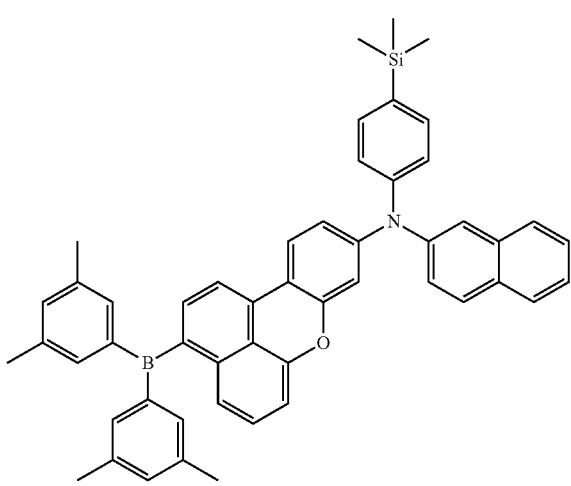
29
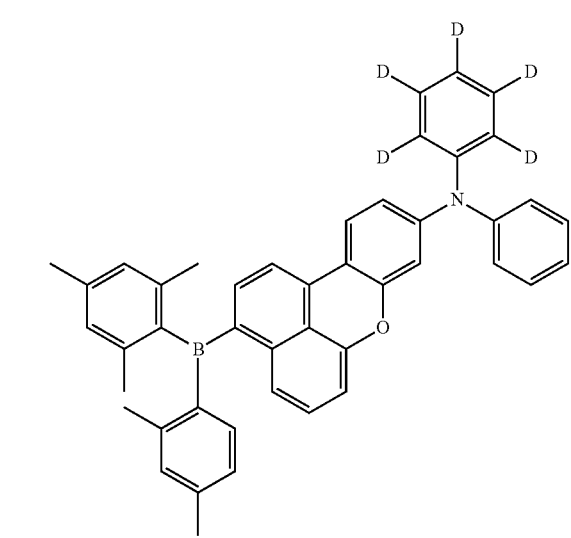
30
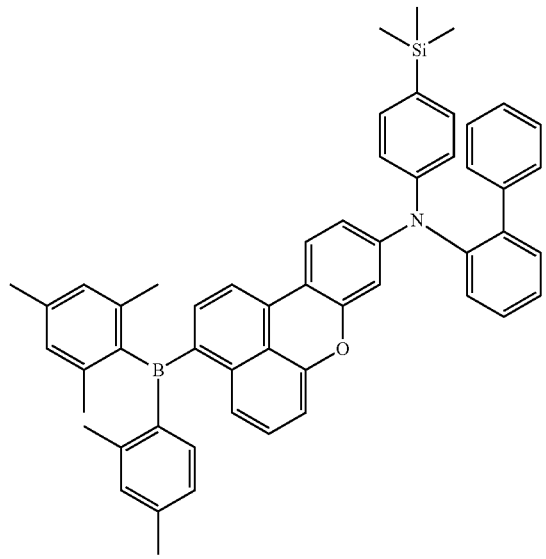
31
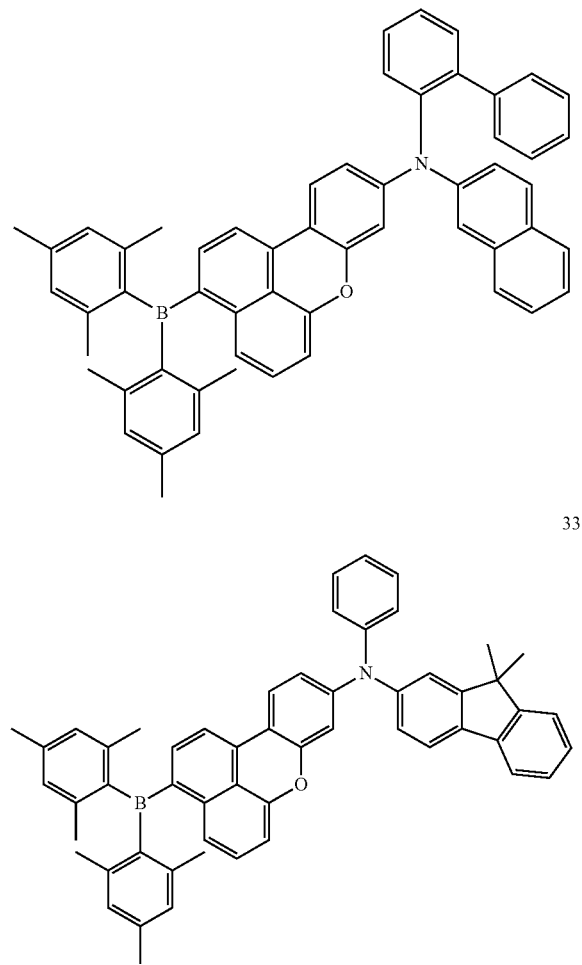

34
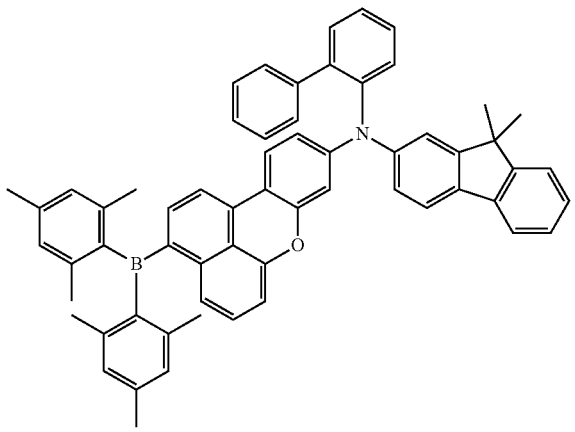
37
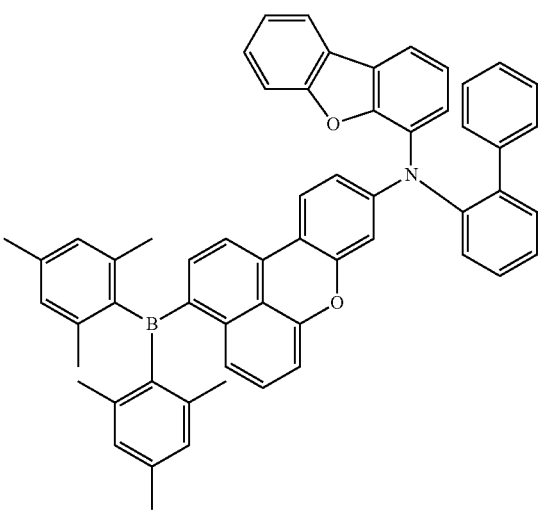
35
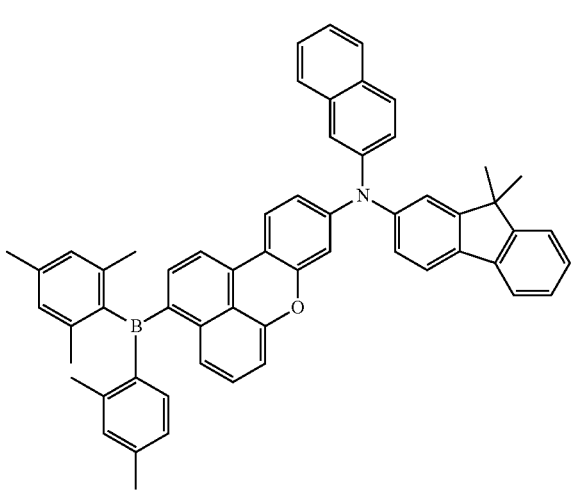
38
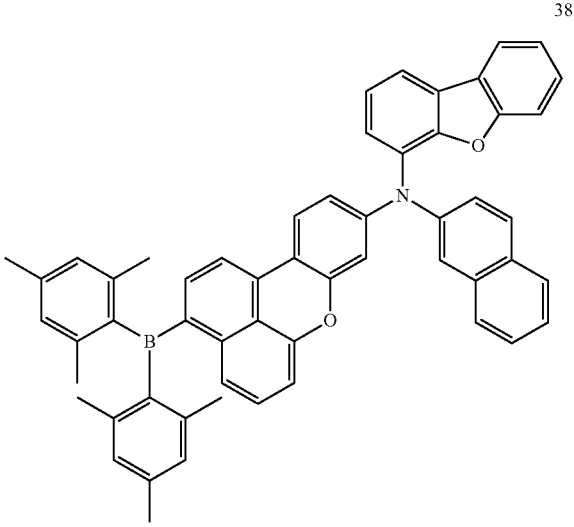
36
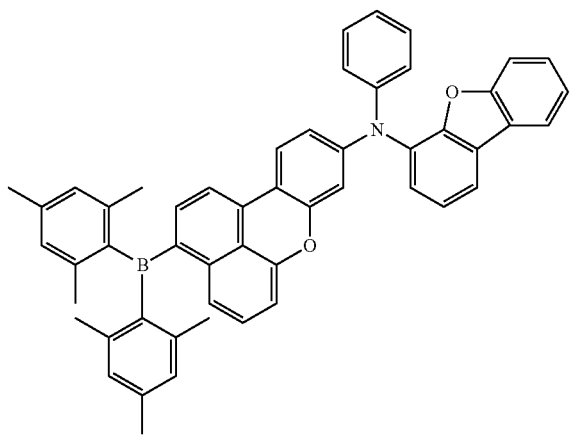
39
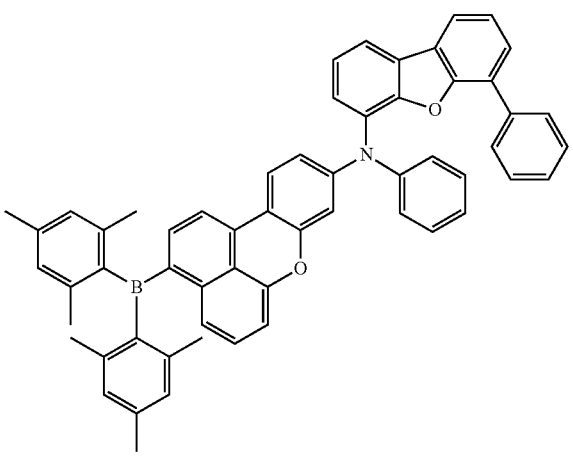

40
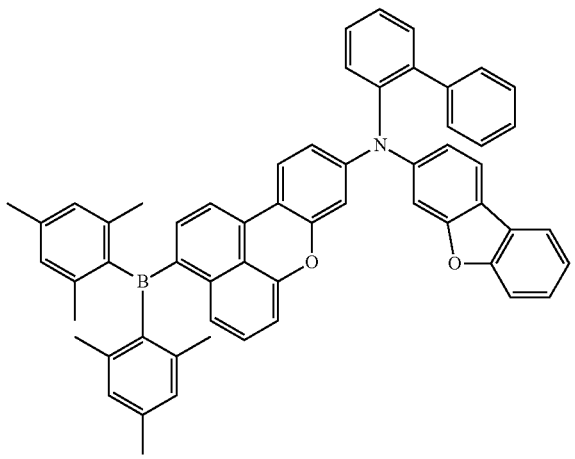
43
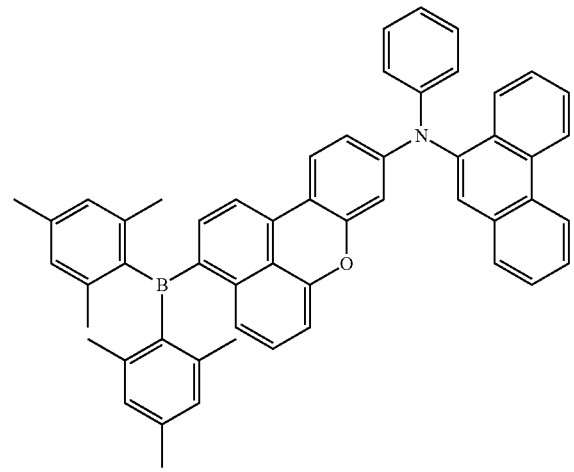
41
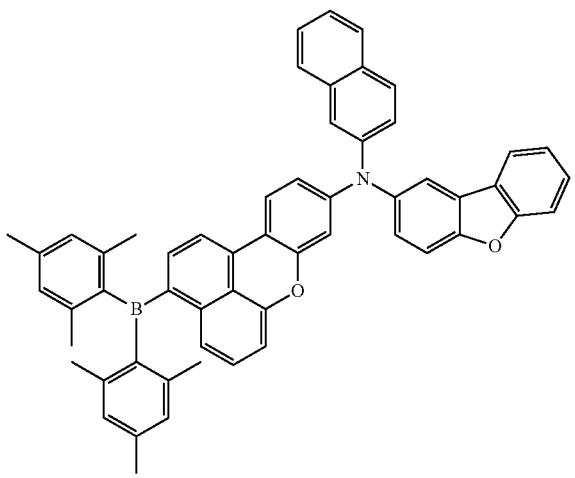
44
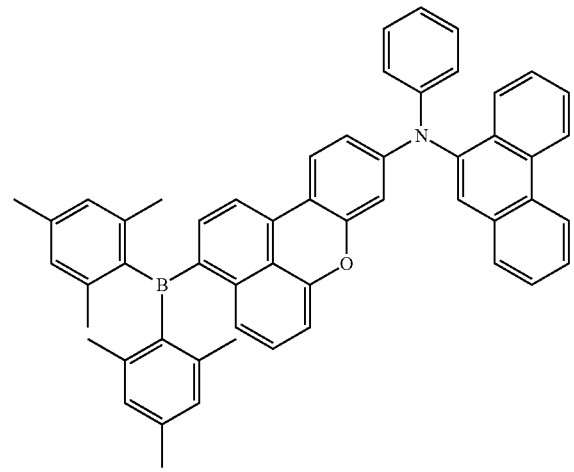
42
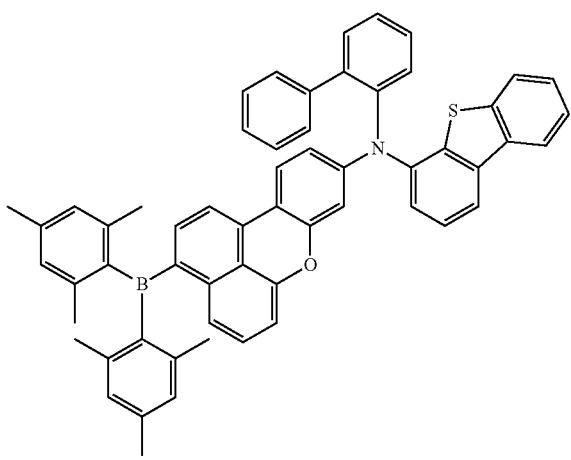
45
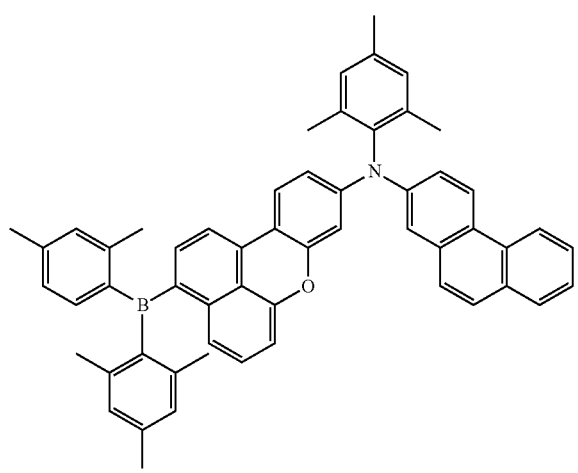

46
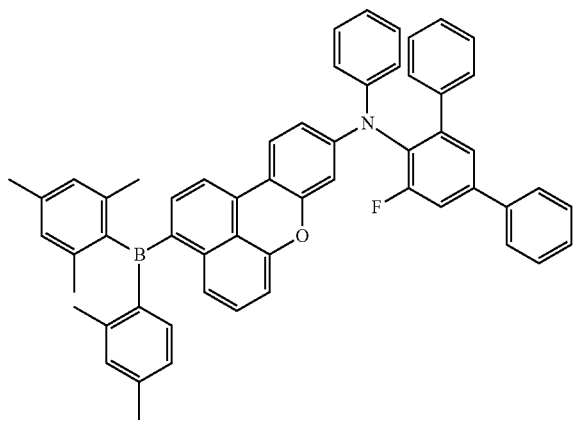
47
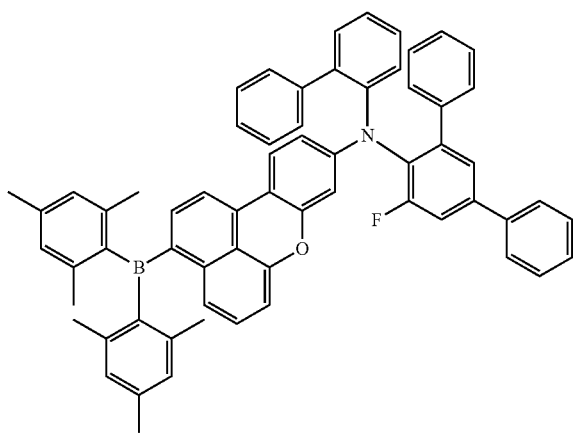
48
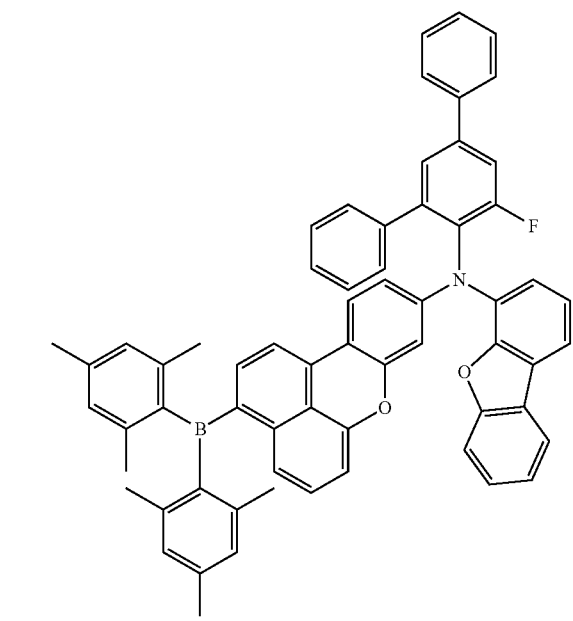
49
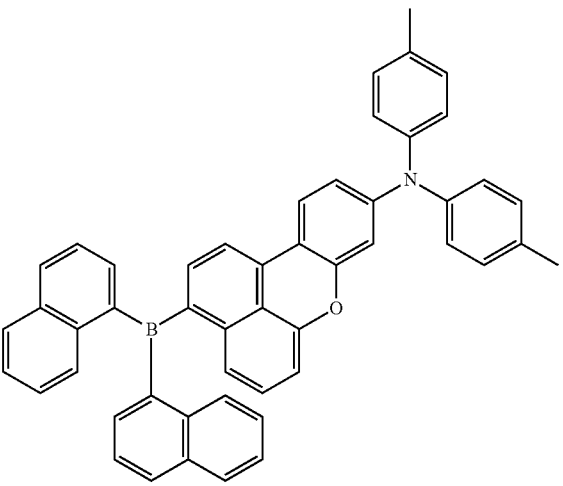
50
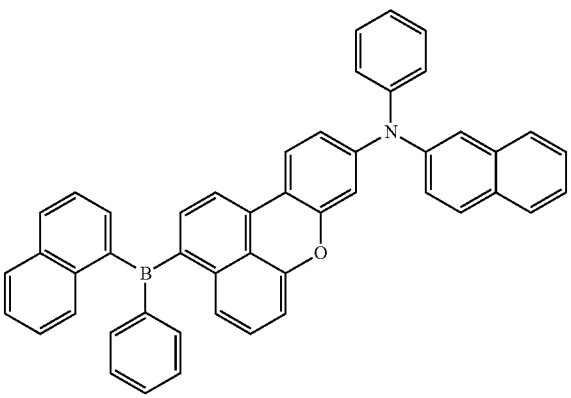
51
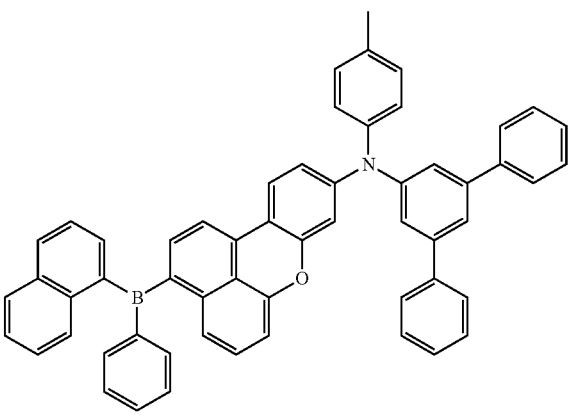

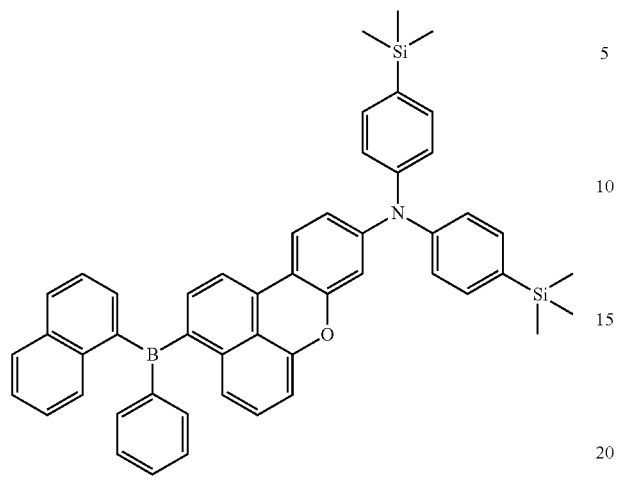
52
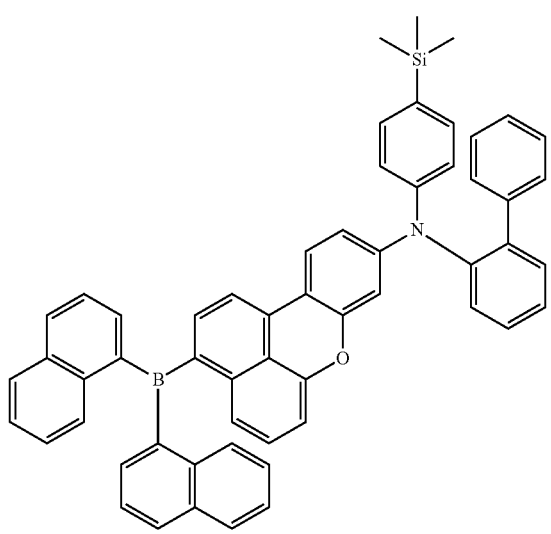
55
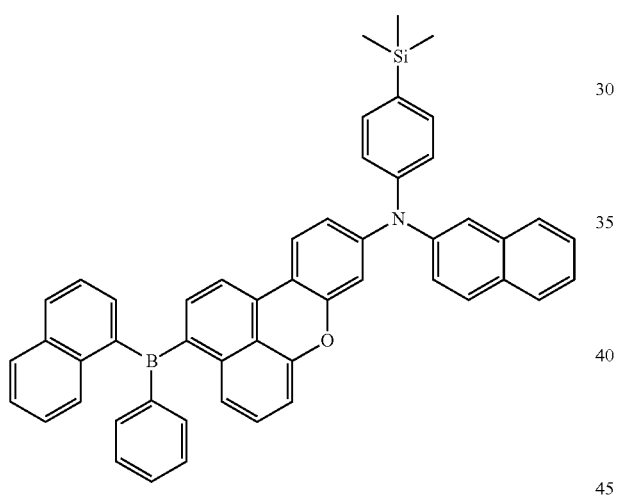
53
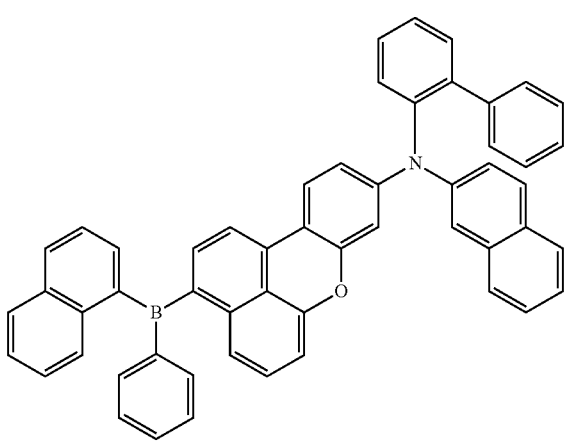
56
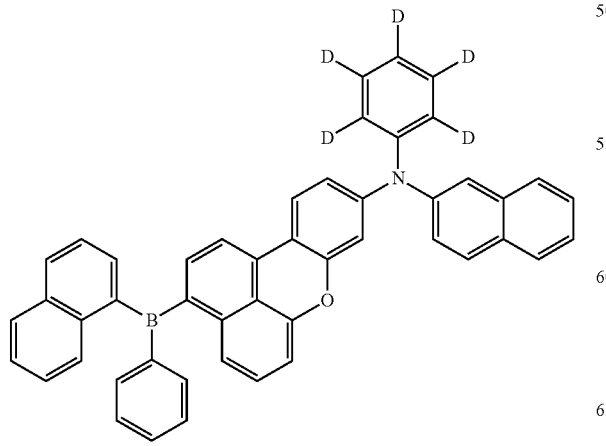
54
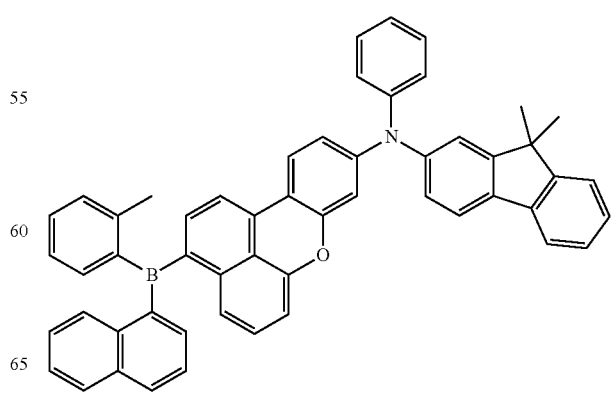
57

58
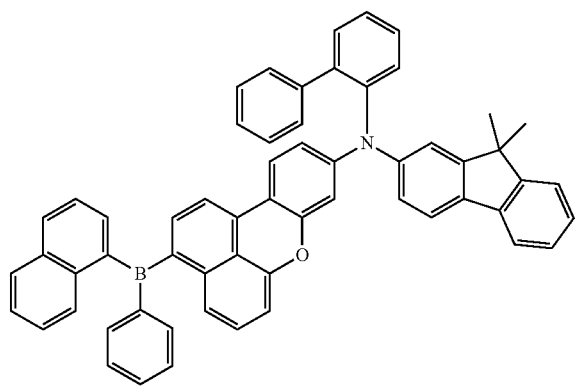
59
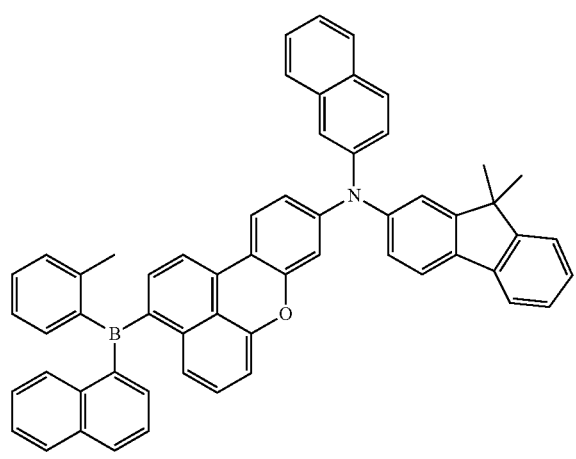
60
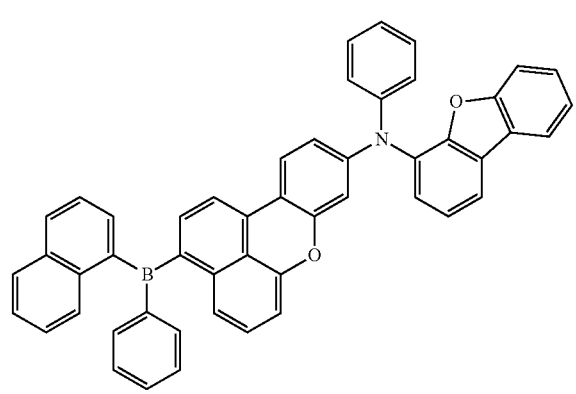
61
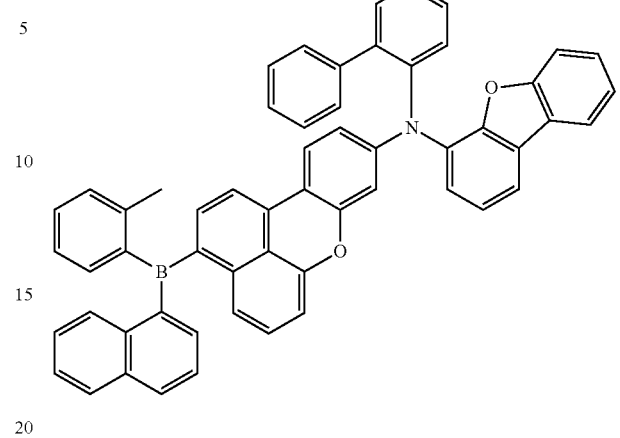
62
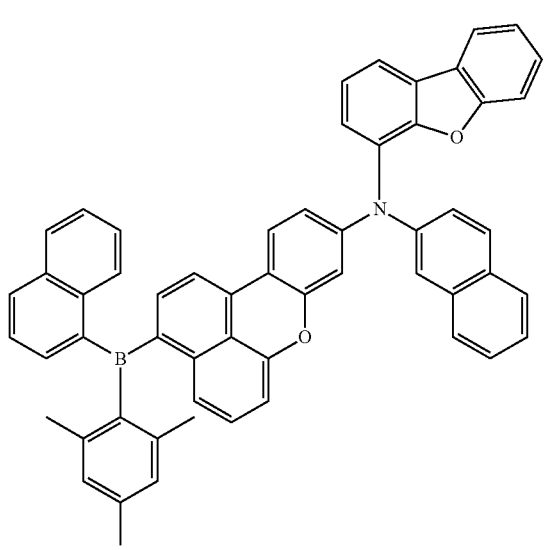
63
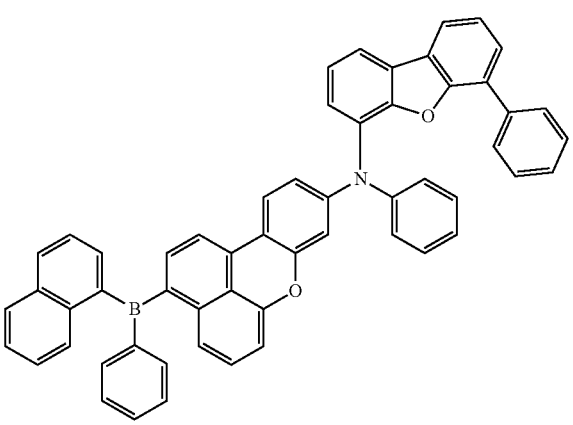

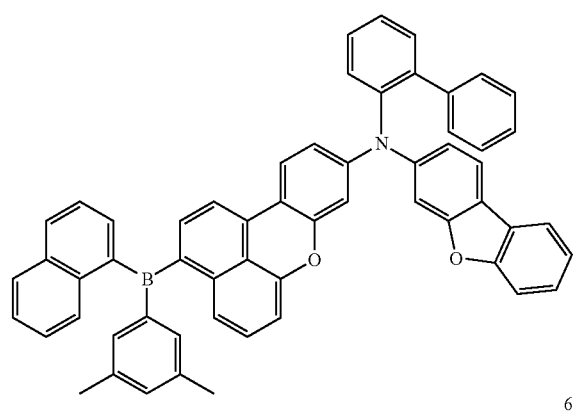
64
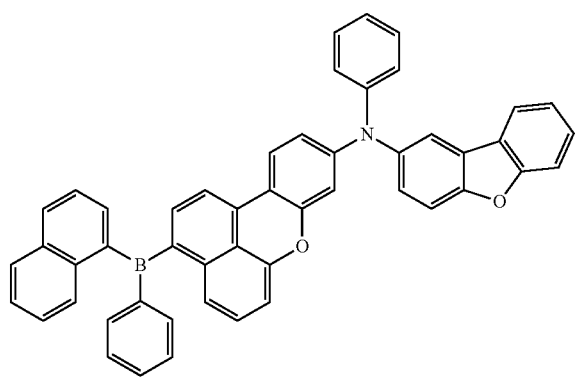
65
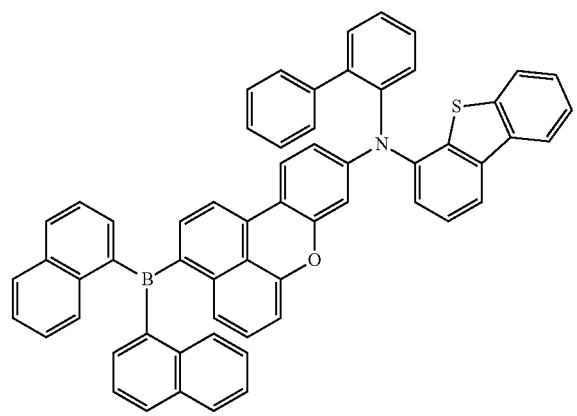
66
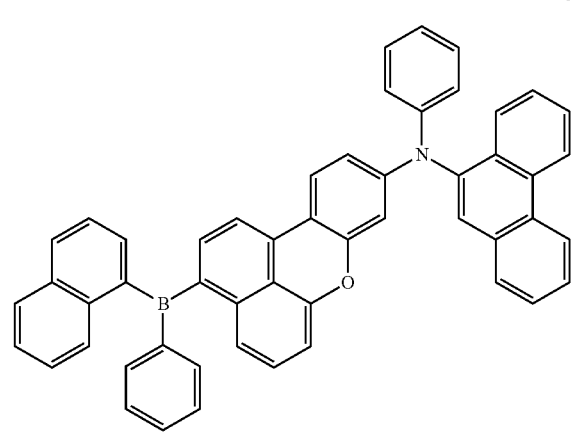
67
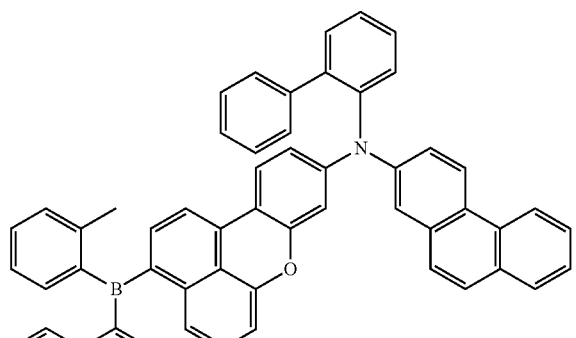
68
69
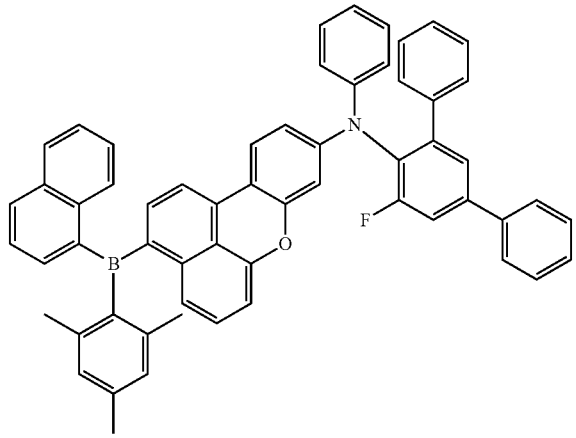
70

71
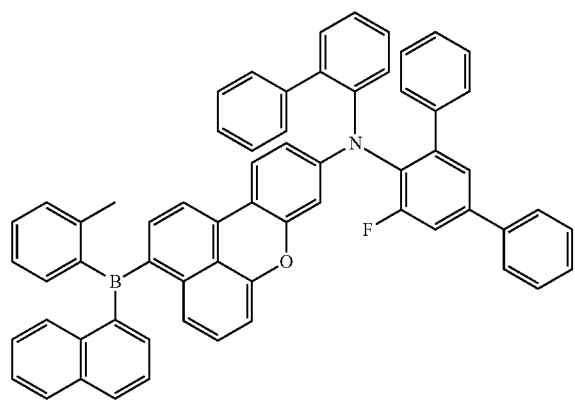
72
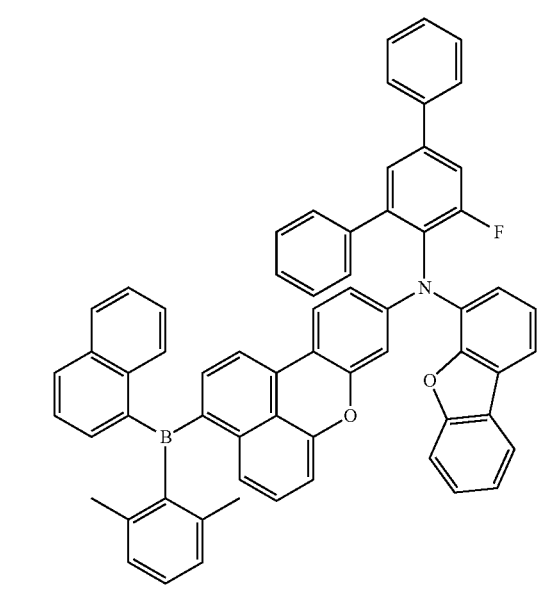
73
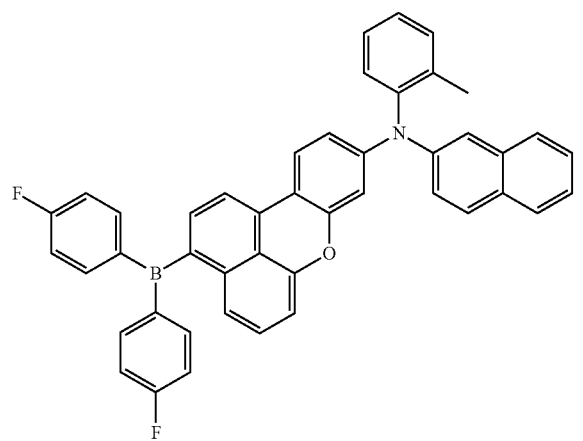
74
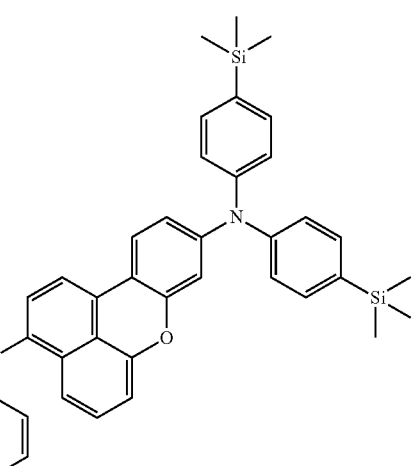
75
76
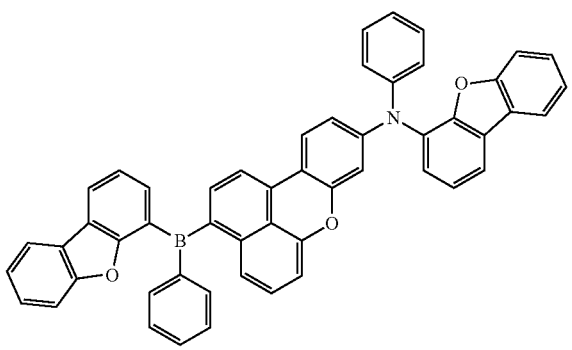

77
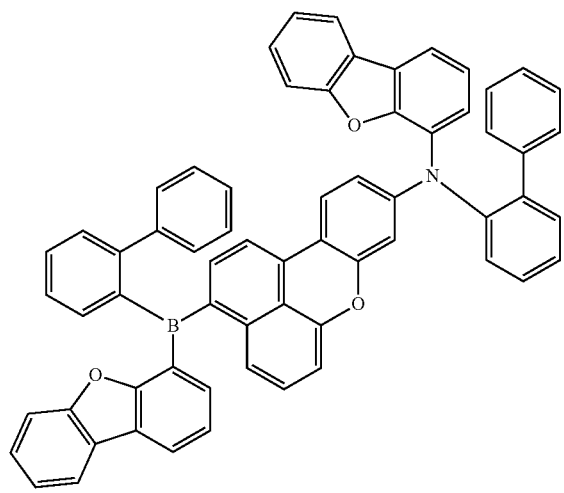
78
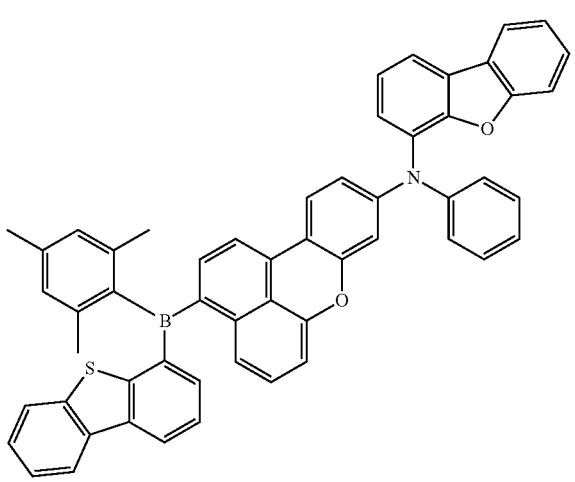
79
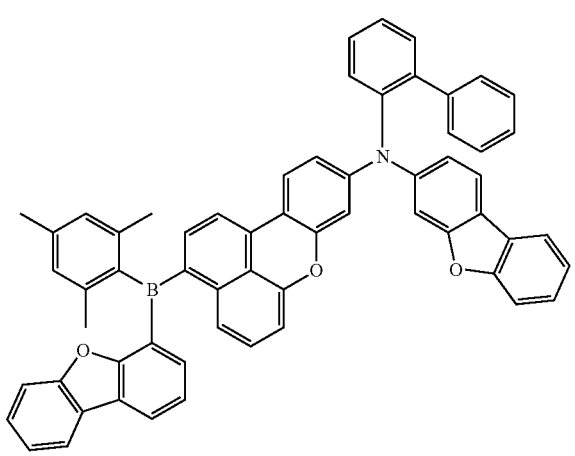
80
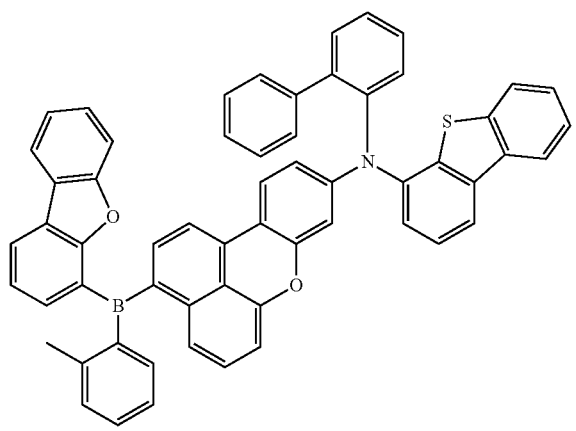
81
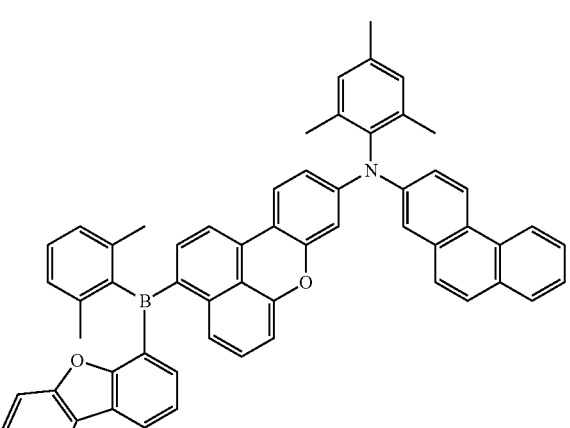
82
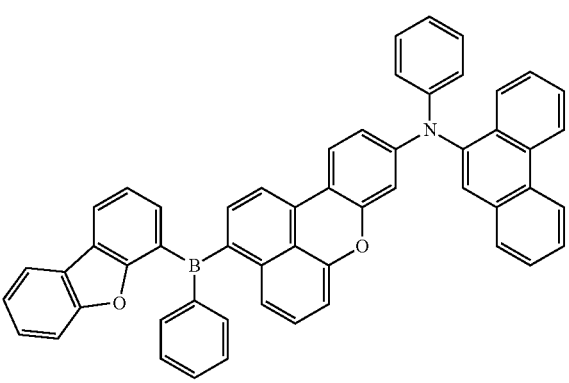

83
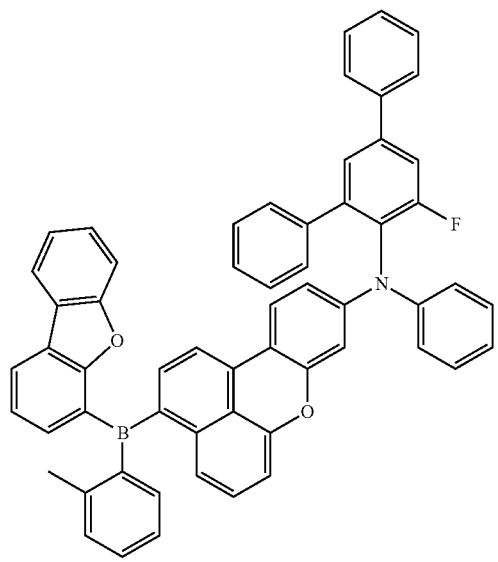
84
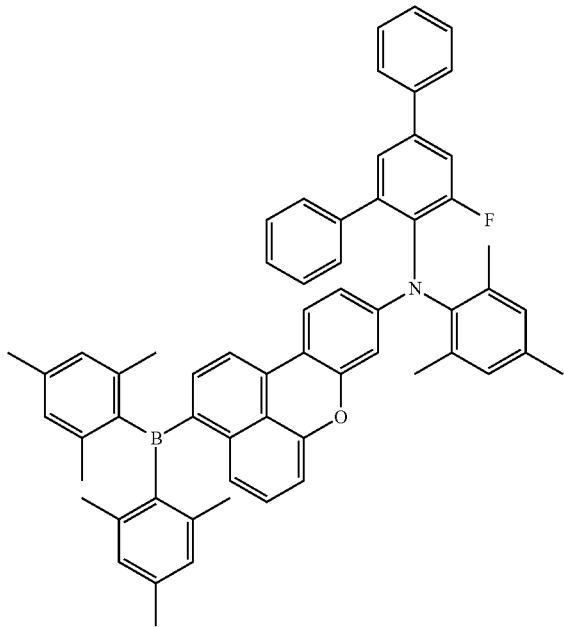
85
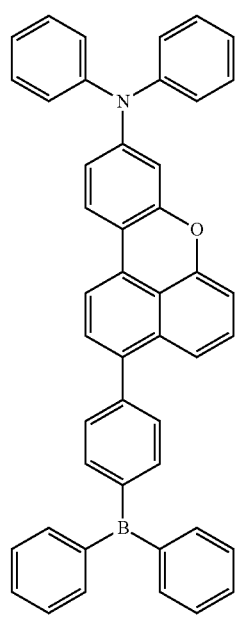
86
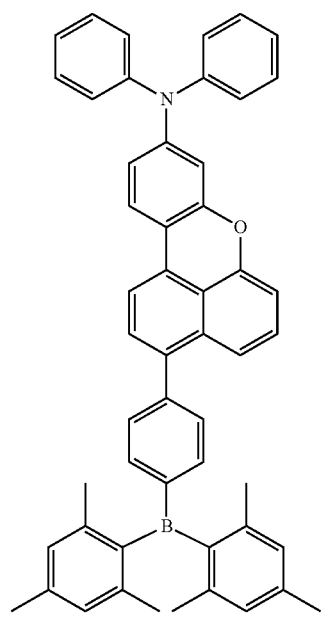

87
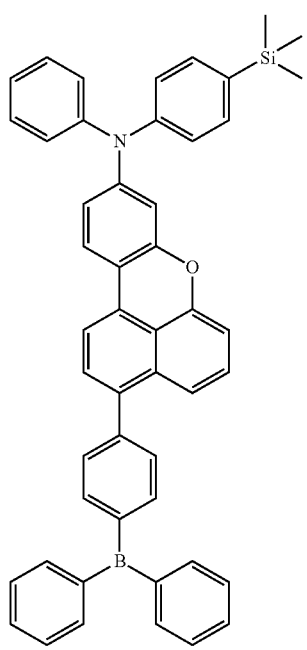
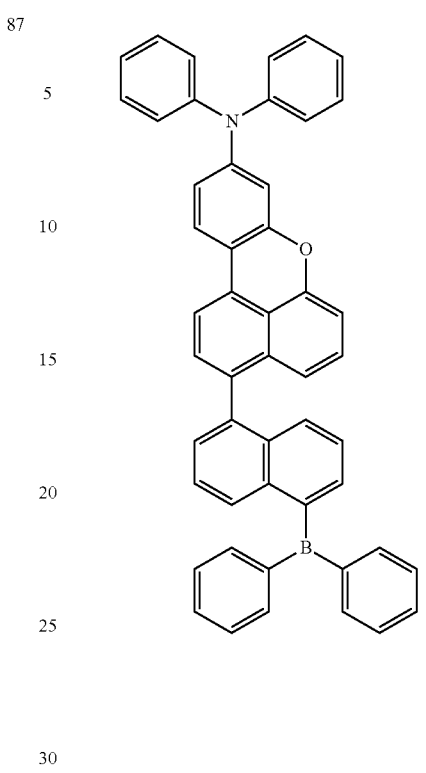
88
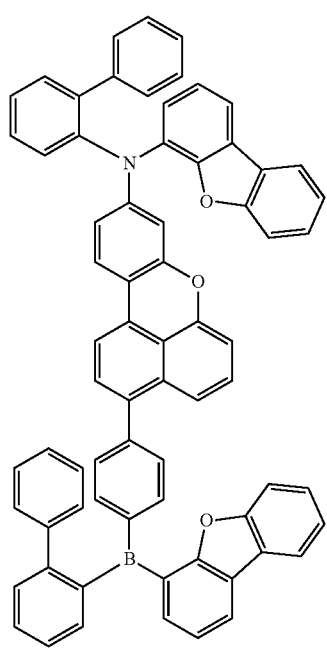
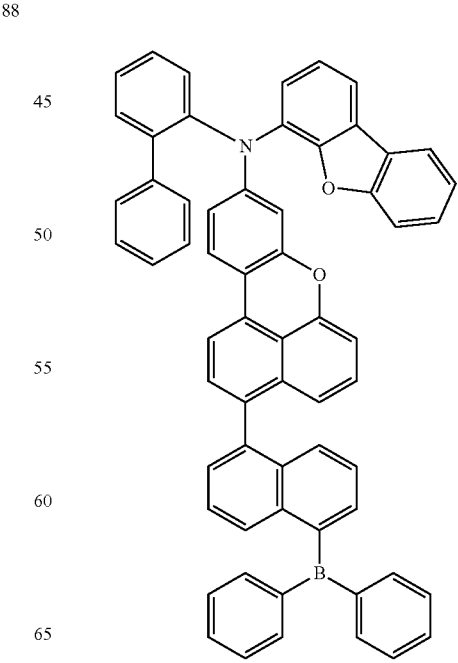

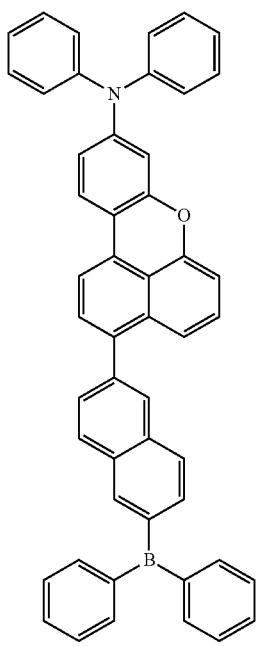
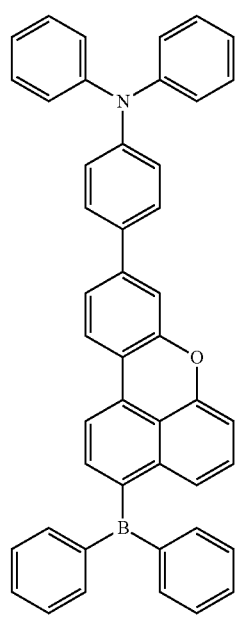

95
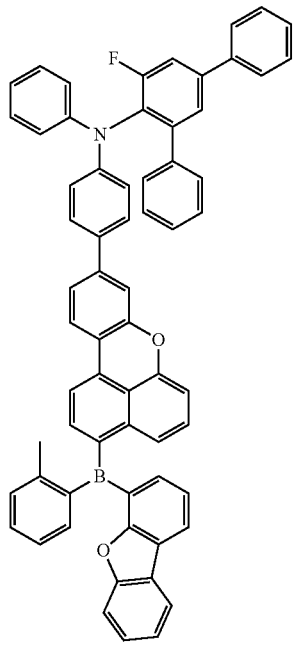
96
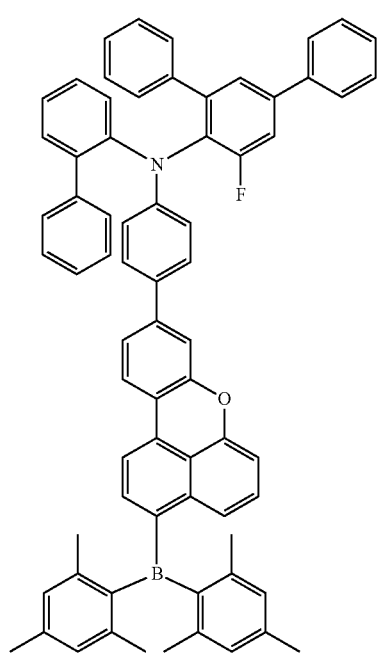
97
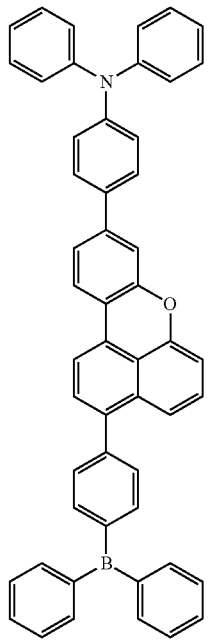
98
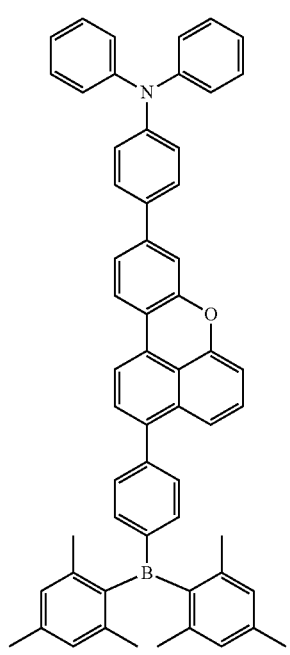

-continued

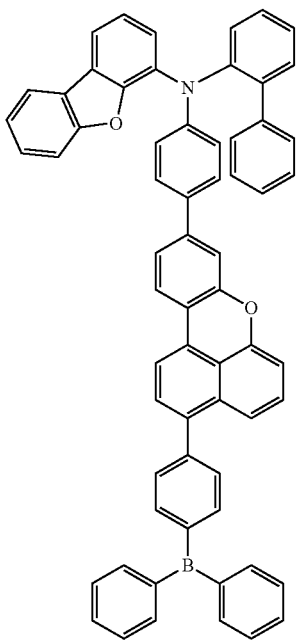
99

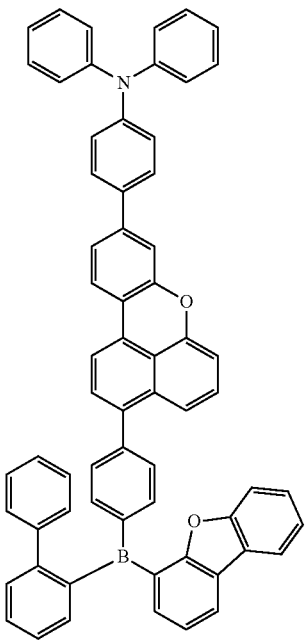
100

The condensed-cyclic compound represented by Formula 1 having an amine group and a boryl group in the molecule thereof may have a high glass transition temperature (Tg) or a high melting point. In this regard, the condensed-cyclic compound may have high heat-resistance against Joule's heat generated in an organic layer or between an organic layer and an electrode and may have high durability in high-temperature environments. An organic light-emitting device manufactured using the condensed-cyclic compound represented by Formula 1 may have high durability when stored or operated.

Also, due to an empty p-orbital in the boron atom, the condensed-cyclic compound represented by Formula 1 including a boryl group in the compound may have a high electron attracting property. The compound may have a high electron injection property and a high electron transporting property. An organic light-emitting device including the condensed-cyclic compound may have excellent light-emitting efficiency.

In addition, the condensed-cyclic compound represented by Formula 1 may have a high electron density due to π-conjugation in the compound and thus may have high light-emitting efficiency.

The condensed-cyclic compound represented by Formula 1 may be synthesized by a suitable organic synthetic method as may be understood to one of skill in the art by referring to examples used herein.

At least one of the condensed-cyclic compounds represented by Formula 1 may be used in between a pair of electrodes in an organic light-emitting device. In some embodiments, the condensed-cyclic compound may be included in a hole transport region, for example, a hole transport layer. In some embodiments, the condensed-cyclic compound may be included in an emission layer. An organic light-emitting device may include a first electrode, a second electrode facing the first electrode, and an organic layer that is disposed between the first electrode and the second electrode and includes an emission layer, wherein the organic layer includes the condensed-cyclic compound represented by Formula 1.

As used herein, the expression the "(organic layer) includes at least one condensed-cyclic compound" may be construed as meaning the "(organic layer) may include one condensed-cyclic compound represented by Formula 1 or two different condensed-cyclic compounds represented by Formula 1".

For example, the organic layer may include only Compound 1 as the condensed-cyclic compound. In this regard, Compound 1 may be included in the emission layer of an organic light-emitting device. In some embodiments, the organic layer may include Compound 1 and Compound 2 as the condensed-cyclic compounds. Here, Compound 1 and Compound 2 may be included in the same layer (e.g., both Compound 1 and Compound 2 may be included in an emission layer) or in different layers (e.g., Compound 1 may be included in the hole transport layer and Compound 2 in the emission layer).

The organic layer may include i) a hole transport region that is disposed between the first electrode (an anode) and the emission layer and includes at least one of a hole injection layer, a hole transport layer, a buffer layer, and an electron blocking layer, and ii) an electron transport region that is disposed between the emission layer and the second electrode (a cathode) and includes at least one of a hole blocking layer, an electron transport layer, and an electron injection layer. At least one of the hole transport region and the emission layer may include the condensed-cyclic compound represented by Formula 1. For example, the hole transport region may include a hole transport layer that includes at least one of the condensed-cyclic compounds represented by Formula 1.

As used herein, the term the "organic layer" refers to a single layer and/or a plurality of layers disposed between the first electrode and the second electrode in an organic light-emitting device. The organic layer may include other materials besides an organic material FIG. 1 illustrates a schematic view of an organic light-emitting device 10 according to an embodiment. The organic light-emitting device 10 includes a first electrode 110, an organic layer 150, and a second electrode 190.

Hereinafter, a structure and a method of manufacturing the organic light-emitting device according to an embodiment will be described with reference to FIG. 1.

Referring to FIG. 1, a substrate may be additionally disposed under the first electrode 110 or on the second electrode 190. The substrate may be a substrate with excellent mechanical strength, thermal stability, transparency, surface smoothness, ease of handling, and water resistance, such as a glass substrate or transparent plastic substrate.

The first electrode 110 may be formed by depositing or sputtering a material for forming the first electrode on the substrate. When the first electrode 110 is an anode, the material for the first electrode may be selected from materials with a high work function to allow holes to be easily injected. The first electrode 110 may be a reflective electrode, a semi-transmissive electrode, or a transmissive electrode. The material for the first electrode may be a transparent and highly conductive material. Examples of such a material include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one selected from magnesium (Mg), aluminum (Al), aluminum-lithium (Al—Li), calcium (Ca), magnesium-indium (Mg—In), and magnesium-silver (Mg—Ag) may be used.

The first electrode 110 may have a single-layer structure, or a multi-layer structure including a plurality of layers. For example, the first electrode 110 may have a triple-layer structure of ITO/Ag/ITO.

The organic layer 150 may be disposed on the first electrode 110. The organic layer 150 may include an emission layer.

The organic layer 150 may further include a hole transport region disposed between the first electrode and the emission layer, and an electron transport region disposed between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by a suitable method, such as vacuum-deposition, spin coating, casting, Langmuir-Blodgett (LB) method, ink-jet printing, laser-printing, or laser-induced thermal imaging (LITI).

When a hole injection layer is formed by vacuum-deposition, the vacuum-deposition may be performed at a deposition temperature in a range of about 100° C. to about 500° C., a vacuum degree of about $10^{-8}$ torr to about $10^{-3}$ torr, and a deposition rate in a range of about 0.01 Å/sec to about 100 Å/sec in consideration of a compound for a hole injection layer to be deposited, and the structure of a hole injection layer to be formed.

When a hole injection layer is formed by spin coating, the spin coating may be performed at a coating rate of about 2,000 rpm to about 5,000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by a suitable method, such as vacuum-deposition, spin coating, casting, LB method, ink-jet printing, laser-printing, or LITI. When the hole transport layer is formed by vacuum-deposition or spin coating, conditions for vacuum-deposition and coating may be similar to to the above-described vacuum-deposition and coating conditions for forming the hole injection layer.

The hole transport region may include at least one selected from m-MTDATA, TDATA, 2-TNATA, NPB, β-NPB, TPD, a spiro-TPD, a spiro-NPB, α-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

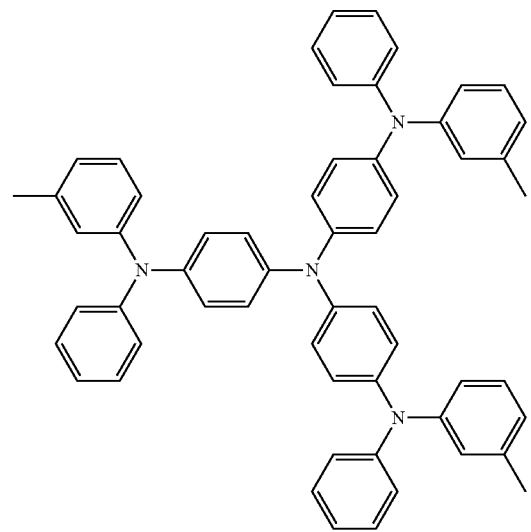

m-MTDATA

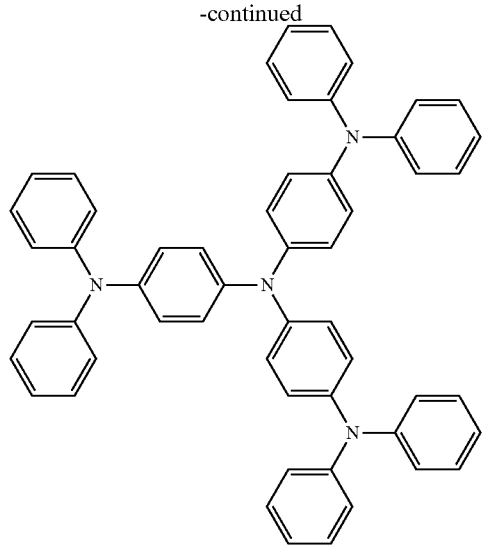
TDATA
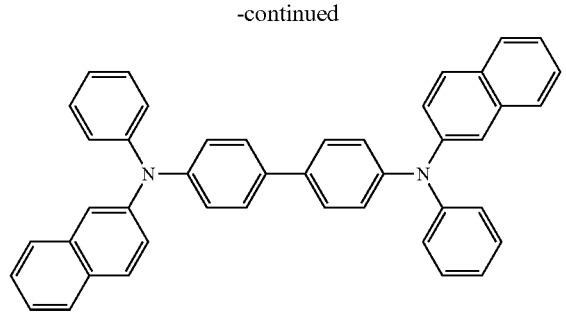
β-NPB
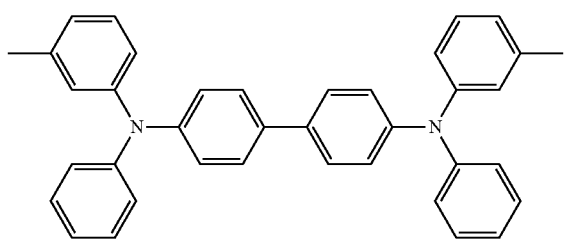
TPD
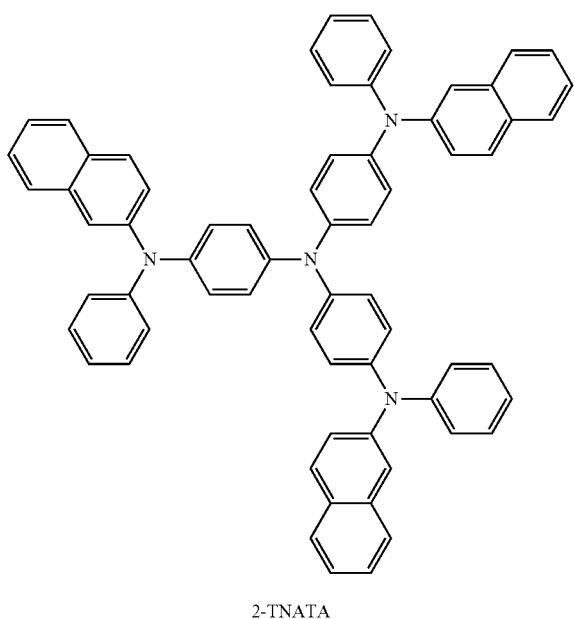
2-TNATA
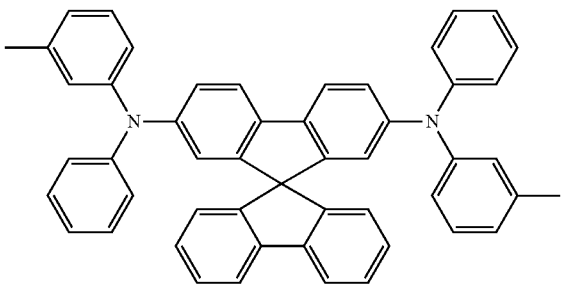
Spiro-TPD
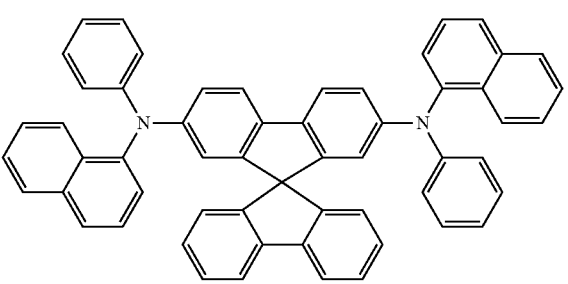
Spiro-NPB
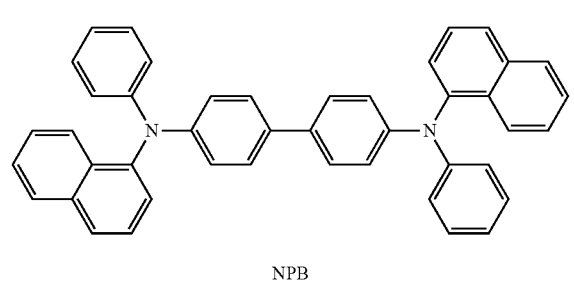
NPB
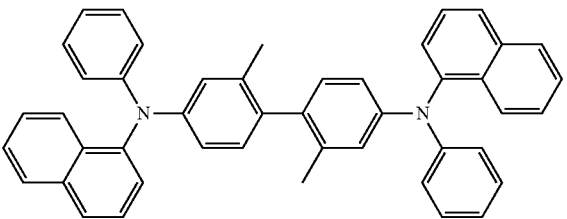
methylated NPB -continued

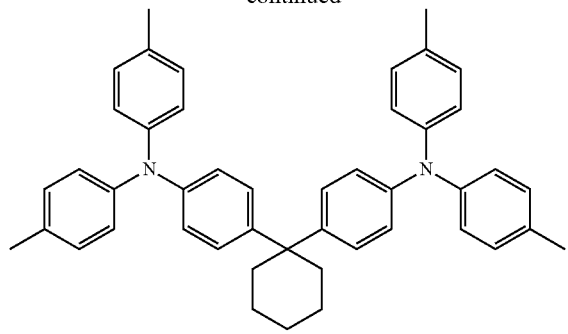

TAPC

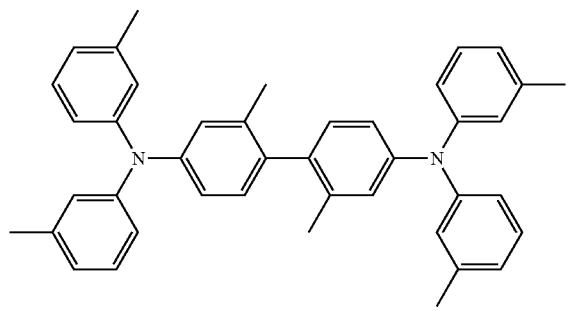

HMTPD

<Formula 201>

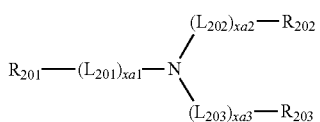

<Formula 202>

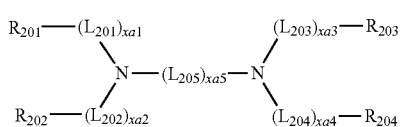

In Formulae 201 and 202, $L_{201}$ to $L_{205}$ may be the same as defined in connection with $L_1$ provided herein;

xa1 to xa4 may be each independently selected from 0, 1, 2, and 3; and xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may be each independently selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently selected from 0, 1, and 2;

xa5 may be selected from 1, 2, and 3;

$R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spino-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A:

<Formula 201A>

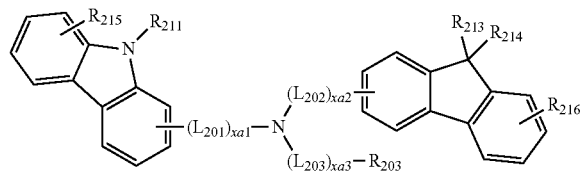

In some embodiments, the compound represented by Formula 201 may be represented by Formula 201A-1:

<Formula 201A-1>

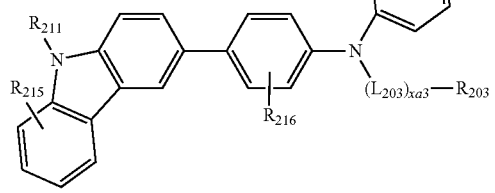

In some embodiments, the compound represented by Formula 202 may be represented by Formula 202A:

<Formula 202A>

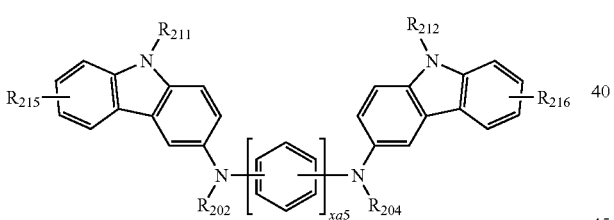

In Formulae 201A, 201A-1, and 202A, descriptions of $L_{201}$ to $L_{203}$, xa1 to xa3, xa5, and $R_{202}$ to $R_{204}$ may be understood by referring to the descriptions provided herein, $R_{211}$ is the same as defined in connection with $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound represented by Formula 201 and the compound represented by Formula 202 may include Compounds HT1 to HT20.

HT1

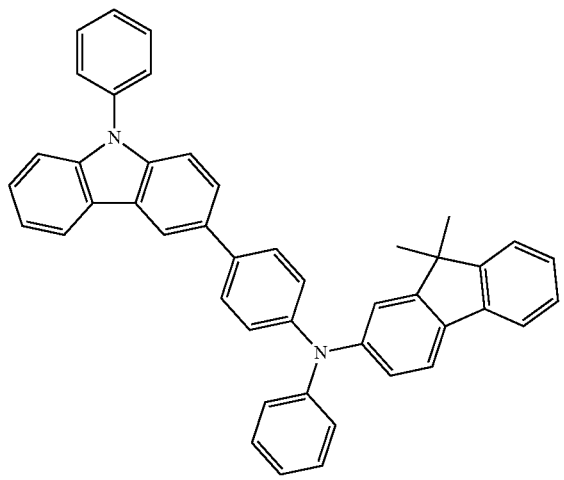

HT2

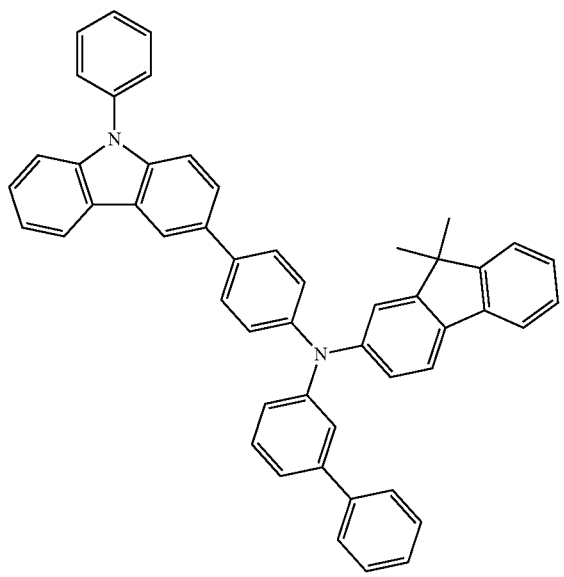

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, or, for example, about 100 Å to about 1,000 Å, and the thickness of the hole transport layer may be in a range of about 50 Å to about 2,000 Å, or, for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material hole transport region.

The charge-generating material may be, for example, a p-dopant. The p-dopant may be one selected from a quinone derivative, a metal oxide, and a cyano group-containing compound. For example, non-limiting examples of the p-dopant include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

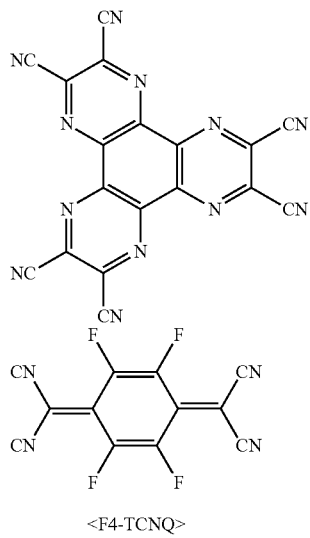

<Compound HT-D1>

<F4-TCNQ>

The hole transport region may further include, in addition to the hole injection layer and the hole transport layer, at least one selected from a buffer layer and an electron blocking layer. The buffer layer may compensate for an optical resonance distance according to a wavelength of light emitted from the emission layer. Accordingly, light-emission efficiency of a formed organic light-emitting device may be improved. As a material included in the buffer layer, materials that are included in the hole transport region may be used. The electron blocking layer may help prevent the injection of electrons from the electron transport region.

An emission layer may be formed on the first electrode 110 or the hole transport region by a suitable method, such as vacuum-deposition, spin coating, casting, LB method, ink-jet printing, laser-printing, or LITI. When the emission layer is formed by vacuum-deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some implementations, the emission layer may have a stacked structure of a red emission layer, a green emission layer, and a blue emission layer, or may include a red-light emission material, a green-light emission material, and a blue-light emission material, which may be mixed with each other in a single layer, to emit white light.

The emission layer may include the condensed-cyclic compound represented by Formula 1.

The emission layer may include a host and a dopant. The dopant may include the condensed-cyclic compound represented by Formula 1.

The host may include at least one selected from TPBi, TBADN, AND (also known as "DNA"), CBP, CDBP, and TCP:

TPBi

TBADN

ADN

CBP

CDBP

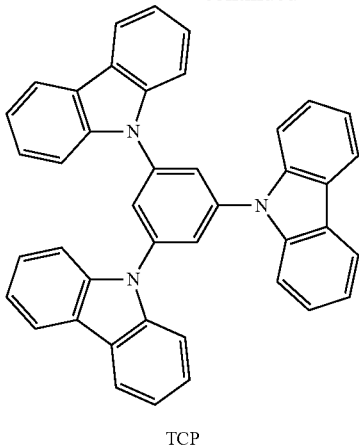

TCP

In some implementations, the host may further include a compound represented by Formula 301:

$$Ar_{301}\text{-}[(L_{301})_{xb1}\text{-}R_{301}]_{xb2}$$ <Formula 301>

In Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where, $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{301}$ may be the same as defined in connection with $L_1$;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4;

In some embodiments, in Formula 301, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

In some embodiment, the host may include a compound represented by Formula 301A:

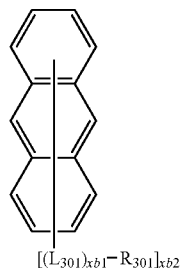

<Formula 301A>

$[(L_{301})_{xb1}-R_{301}]_{xb2}$

The descriptions for Formula 301A may be understood by referring to the descriptions provided herein.

The compound represented by Formula 301 may include at least one compound selected from Compounds H1 to H42 below:

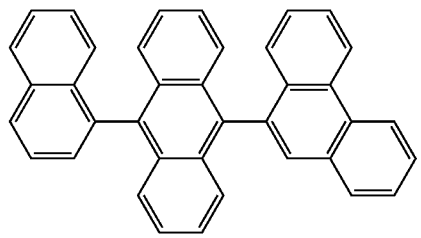

H3

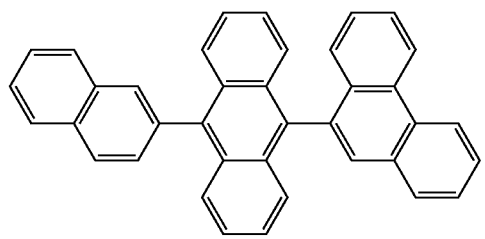

H4

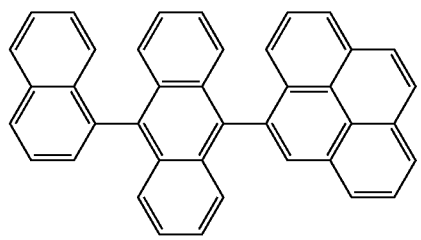

H5

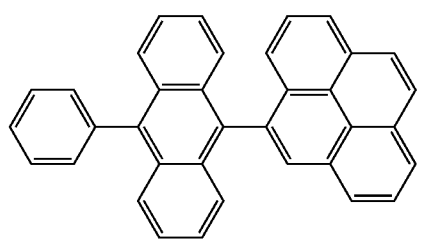

H6

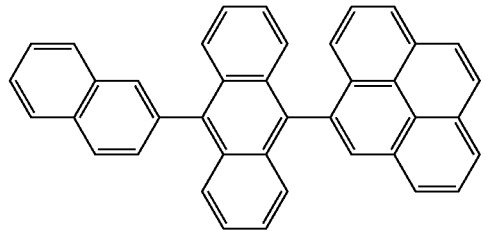

H7

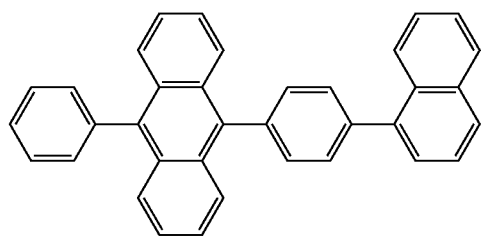

H8

H9
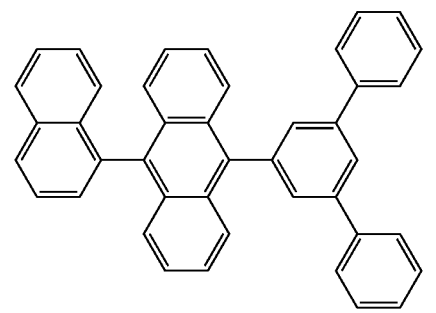
H10
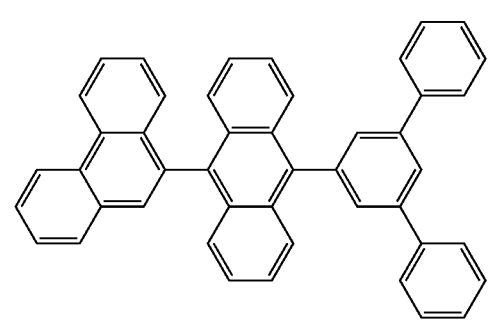
H11
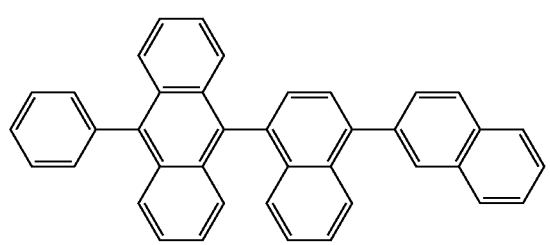
H12
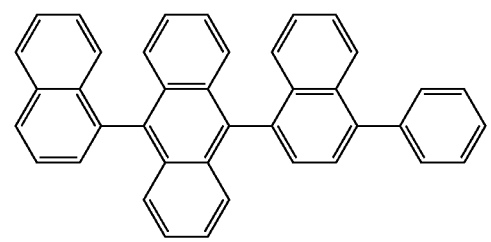
H13
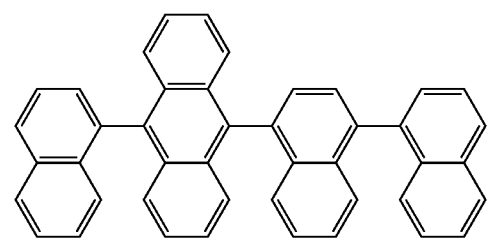
H14
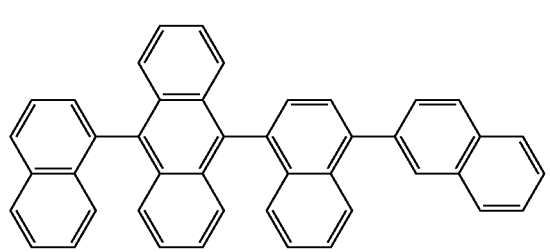
H15
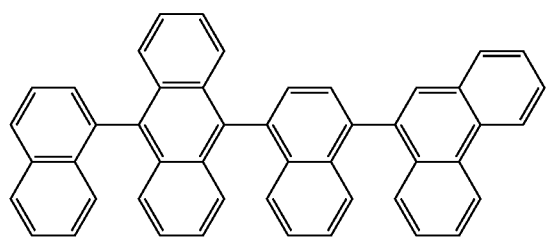
H16
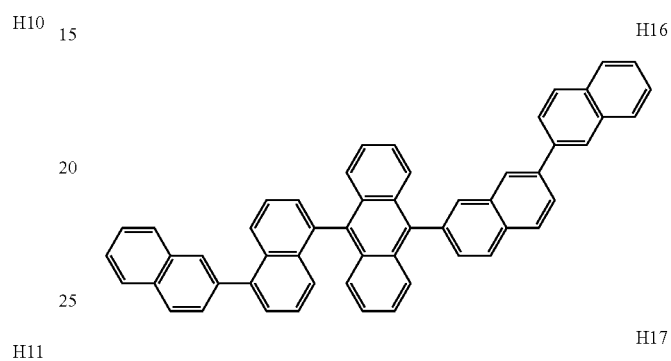
H17
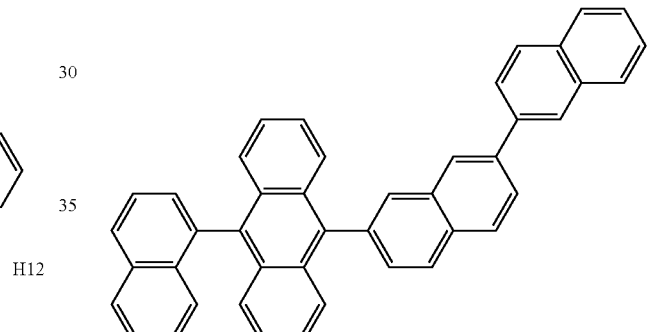
H18
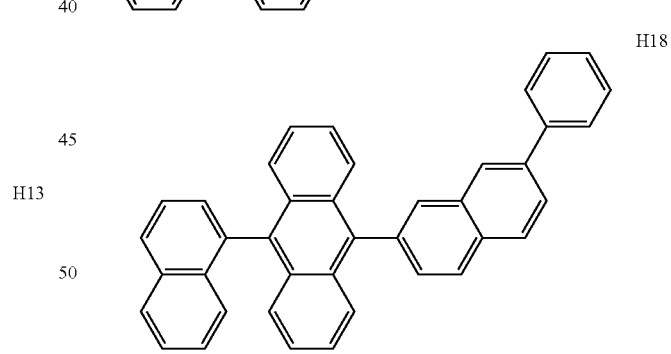
H19
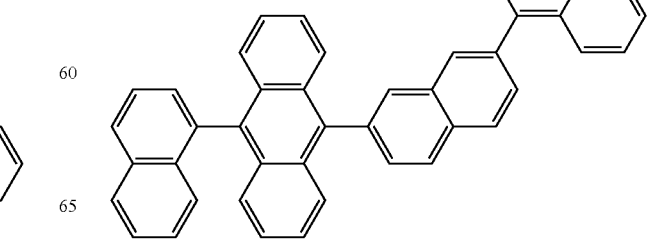

| | |
|---|---|
| H20 | H25 |
| H21 | H26 |
| H22 | H27 |
| H23 | H28 |
| H24 | H29 |
| | H30 |

H31
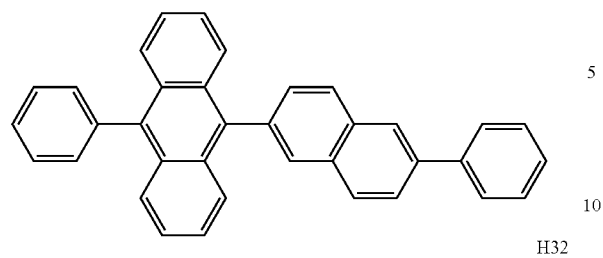
H32
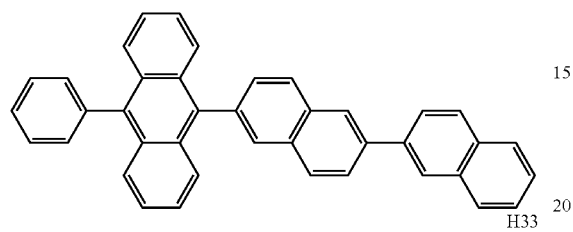
H33
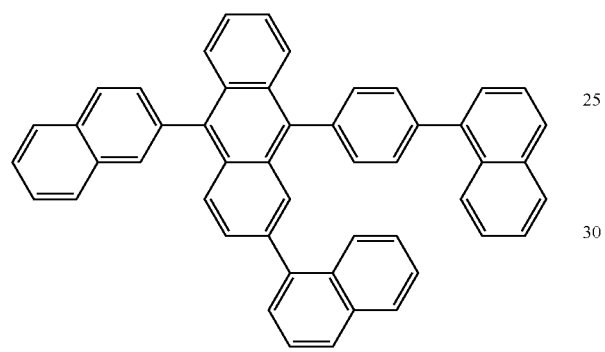
H34
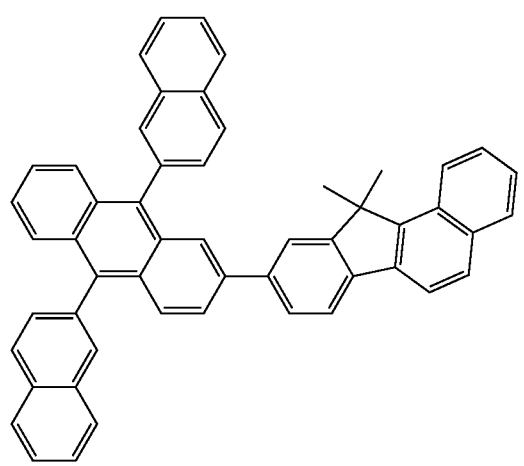
H35
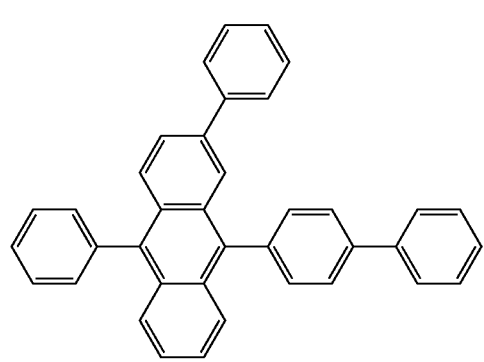
H36
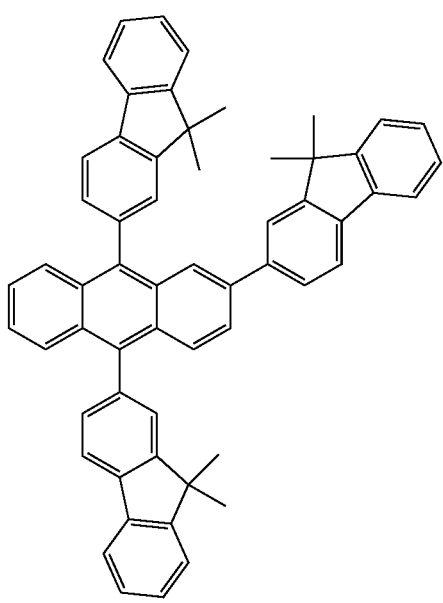
H37
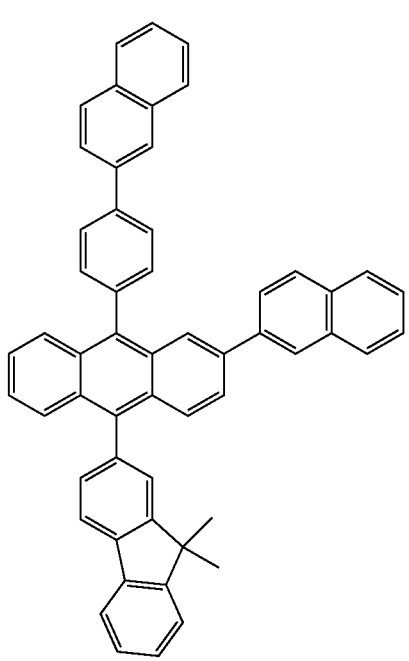
H38
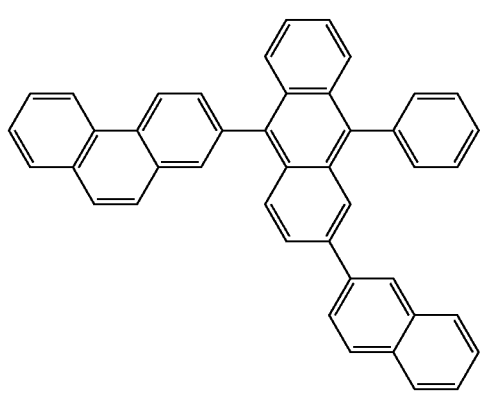

H39
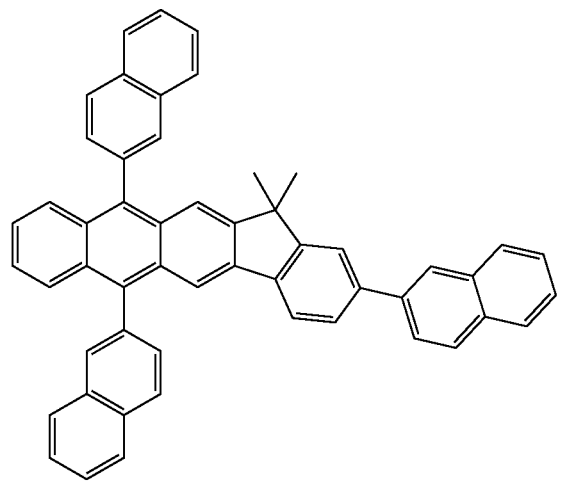
H40
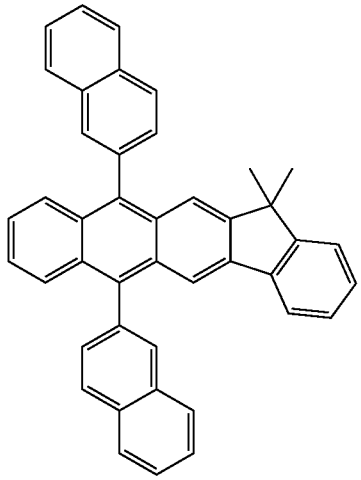
H41
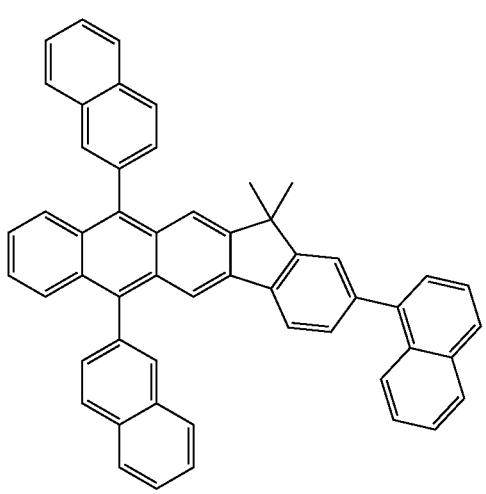
H42
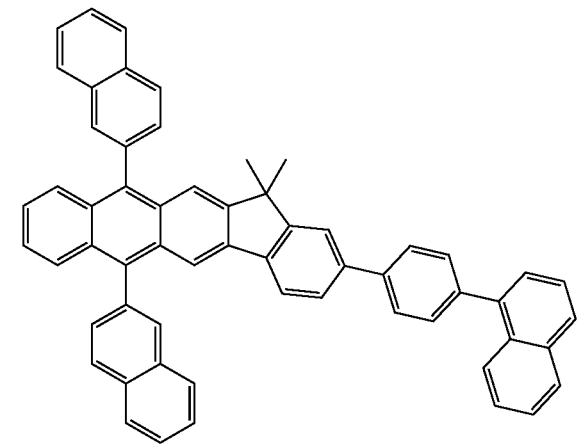
In some embodiments, the host may include at least one selected from Compounds H43 to H49 below:
H43
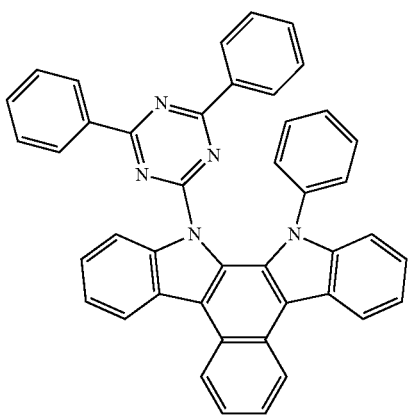
H44
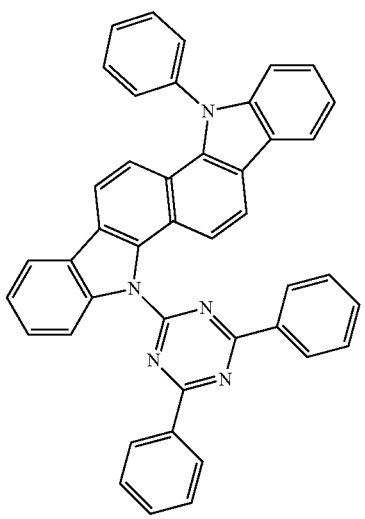

H45

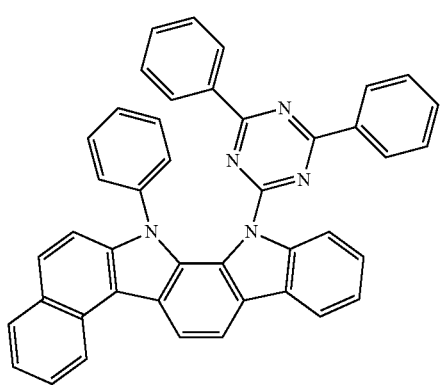

H46

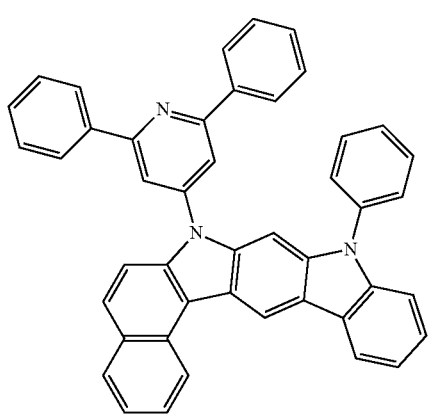

H47

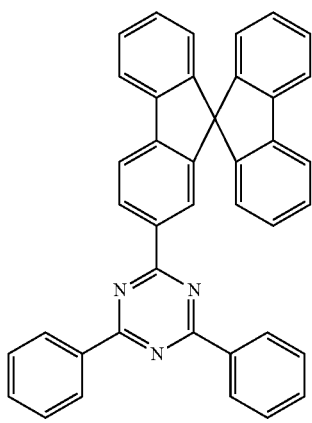

H48

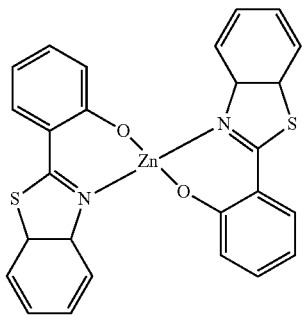

H49

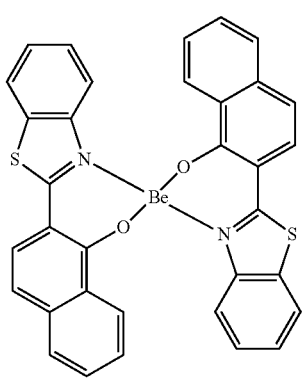

The dopant may include at least one selected from a fluorescent dopant and a phosphorescent dopant. When the dopant includes a fluorescent dopant, the fluorescent dopant may include the condensed-cyclic compound represented by Formula 1.

The fluorescent dopant may include at least one selected from DPAVBi, BDAVBi, TBPe, DCM, DCJTB, Coumarin 6, and C545T, in addition to the condensed-cyclic compound represented by Formula 1.

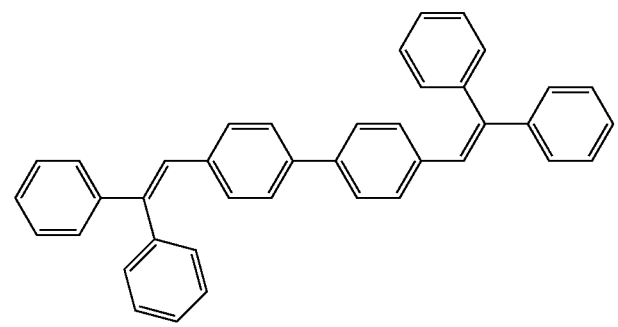

DPVBi

-continued
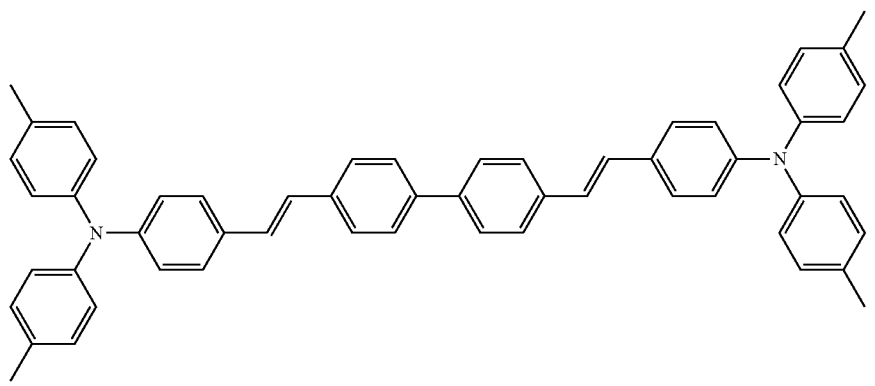
DPAVBi
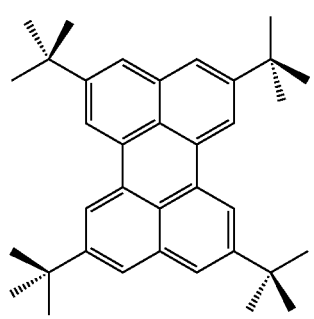
TBPe
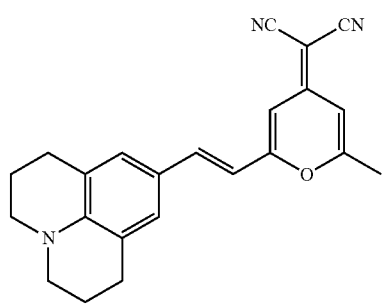
DCM
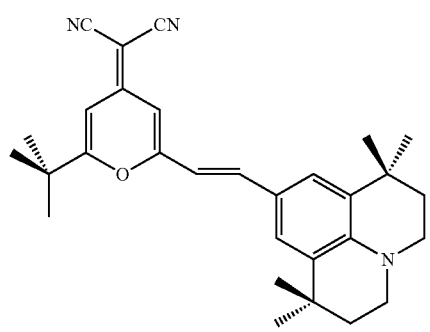
DCJTB
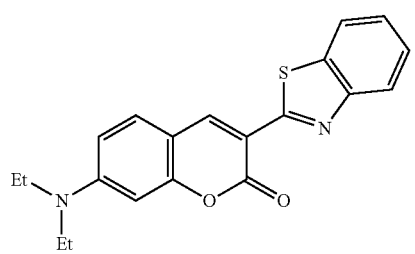
Coumarin 6
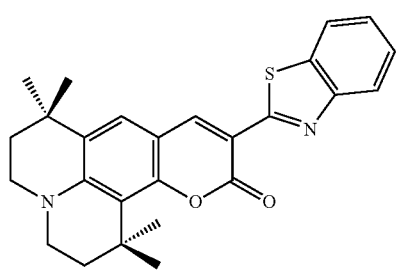
C545T In the emission layer, an amount of the dopant may be in a range of about 0.01 part to about 15 parts by weight based on 100 parts by weight of the host.

A thickness of the emission layer may be in a range of about 100 Å to about 1,000 Å, or, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer, as examples.

For example, the electron transport region may have a structure of electron transport layer/electron injection layer or a structure of hole blocking layer/electron transport layer/electron injection layer, wherein layers of each structure are sequentially stacked from the emission layer in the stated order.

In some embodiments, the organic layer 150 of the organic light-emitting device may include an electron transport region disposed between the emission layer and the second electrode 190.

When the electron transport region includes a hole blocking layer, the hole blocking layer may be formed on the emission layer by a suitable method, such as vacuum-deposition, spin coating, casting, LB method, ink-jet printing, laser-printing, or LITI. When the hole blocking layer is formed by vacuum-deposition or spin coating, deposition and coating conditions for the hole blocking layer may be determined by referring to the deposition and coating conditions for the hole injection layer.

The hole blocking layer may include, for example, at least one selected from BCP and Bphen.

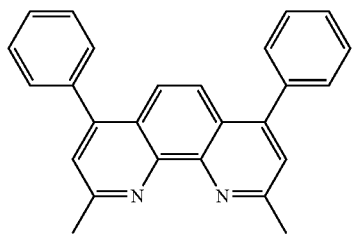

BCP

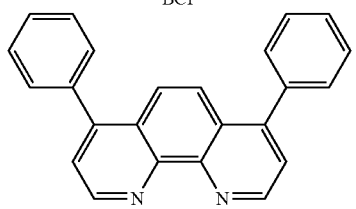

Bphen

A thickness of the hole blocking layer may be in a range of about 20 Å to about 1,000 Å, or, for example, about 30 Å to about 300 Å. When the thickness of the hole blocking layer is within this range, excellent hole blocking characteristics may be obtained without a substantial increase in driving voltage.

The electron transport region may include an electron transport layer. The electron transport layer may be formed on the emission layer or the hole blocking layer by a suitable method, such as vacuum deposition, spin coating, casting, LB method, ink-jet printing, laser-printing, or LITI. When the electron transport layer is formed by using vacuum deposition or spin coating, vacuum deposition and coating conditions for the electron transport layer may be determined by referring to the vacuum deposition and coating conditions for the hole injection layer.

In some embodiments, the electron transport layer may include at least one selected from a compound represented by Formula 601 and a compound represented by Formula 602:

$$Ar_{601}\text{-}[(L_{601})_{xe1}\text{-}E_{601}]_{xe2} \qquad \text{<Formula 601>}$$

wherein, in Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $C_1$-$C_{60}$ alkyl group, $C_2$-$C_{60}$ alkenyl group, $C_2$-$C_{60}$ alkynyl group, $C_1$-$C_{60}$ alkoxy group, $C_3$-$C_{10}$ cycloalkyl group, $C_1$-$C_{10}$ heterocycloalkyl group, $C_3$-$C_{10}$ cycloalkenyl group, $C_1$-$C_{10}$ heterocycloalkenyl group, $C_6$-$C_{60}$ aryl group, $C_6$-$C_{60}$ aryloxy group, $C_6$-$C_{60}$ arylthio group, $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ are each independently selected from a hydrogen, a $C_1$-$C_{60}$ alkyl group, a $C_2$-$C_{60}$ alkenyl group, $C_6$-$C_{60}$ aryl group, and a $C_2$-$C_{60}$ heteroaryl group);

$L_{601}$ may be the same as defined in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and
xe2 may be selected from 1, 2, 3, and 4.

<Formula 602>

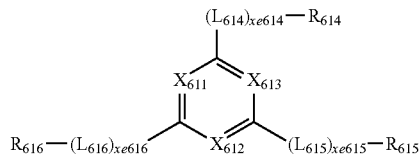

wherein, in Formula 601, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one selected from $X_{611}$ to $X_{613}$ may be N:

$L_{611}$ to $L_{616}$ may be each the same as defined in connection with $L_1$ provided herein;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and triazinyl; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may be each independently selected from 0, 1, 2, and 3.

The compound represented by Formula 601 and the compound represented by Formula 602 may be each independently selected from Compounds ET1 to ET15 illustrated below:

ET1

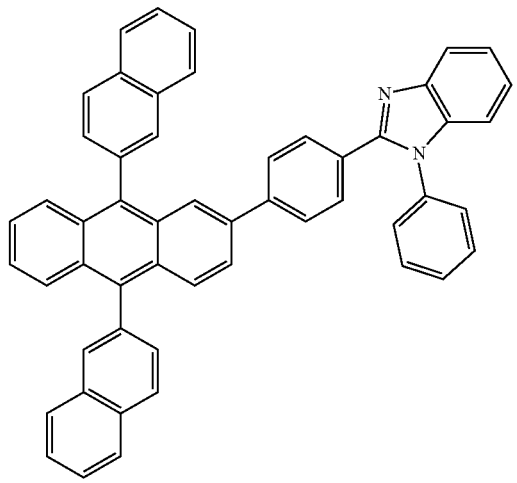

-continued
ET2
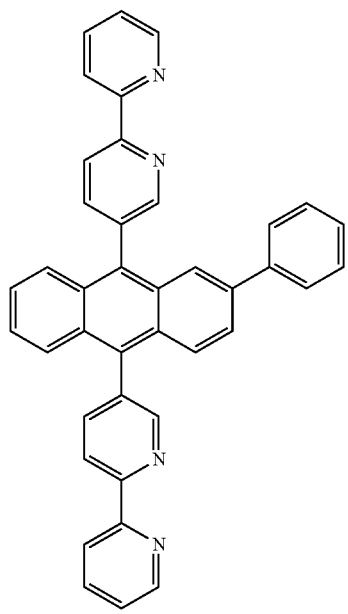
ET3
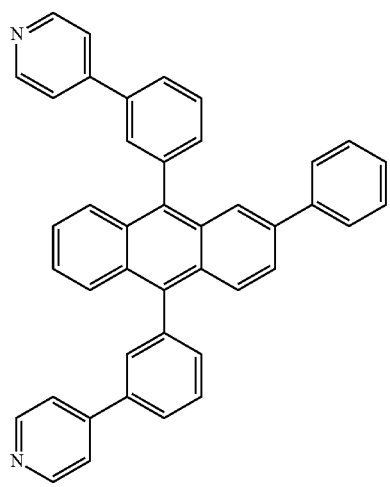
ET4
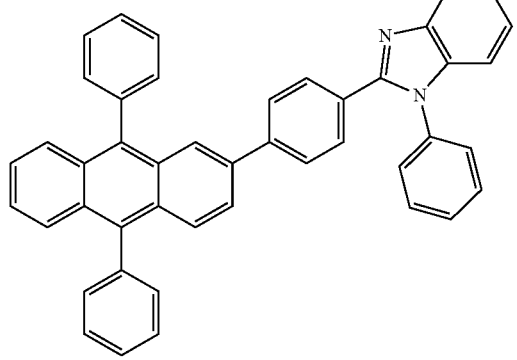
-continued
ET5
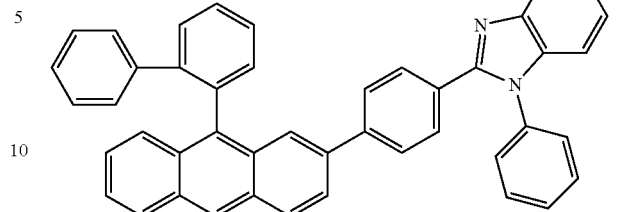
ET6
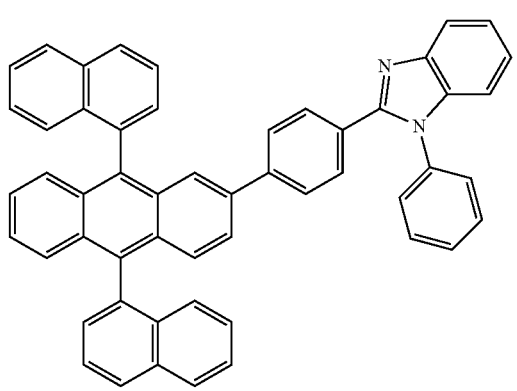
ET7
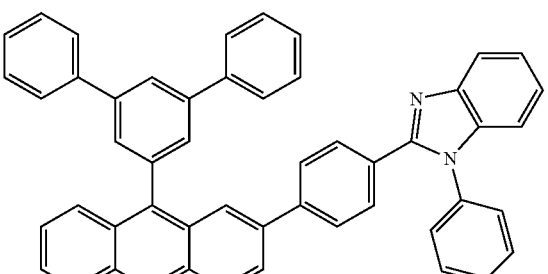
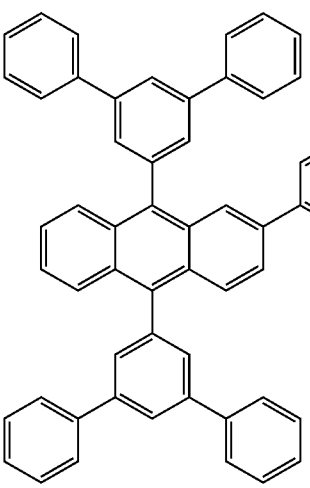

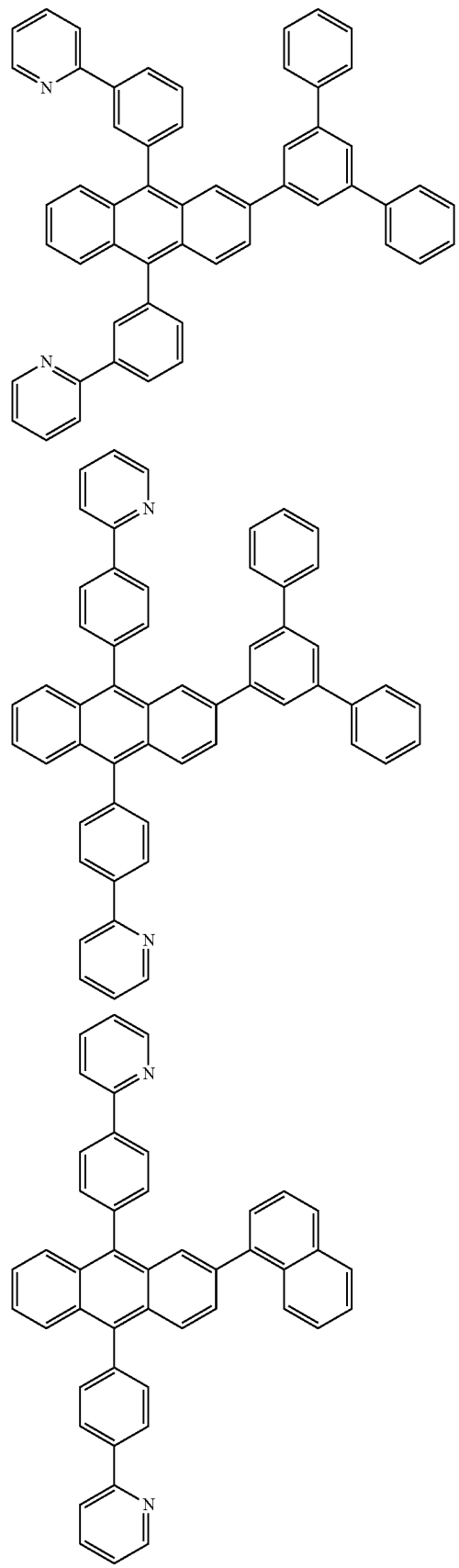
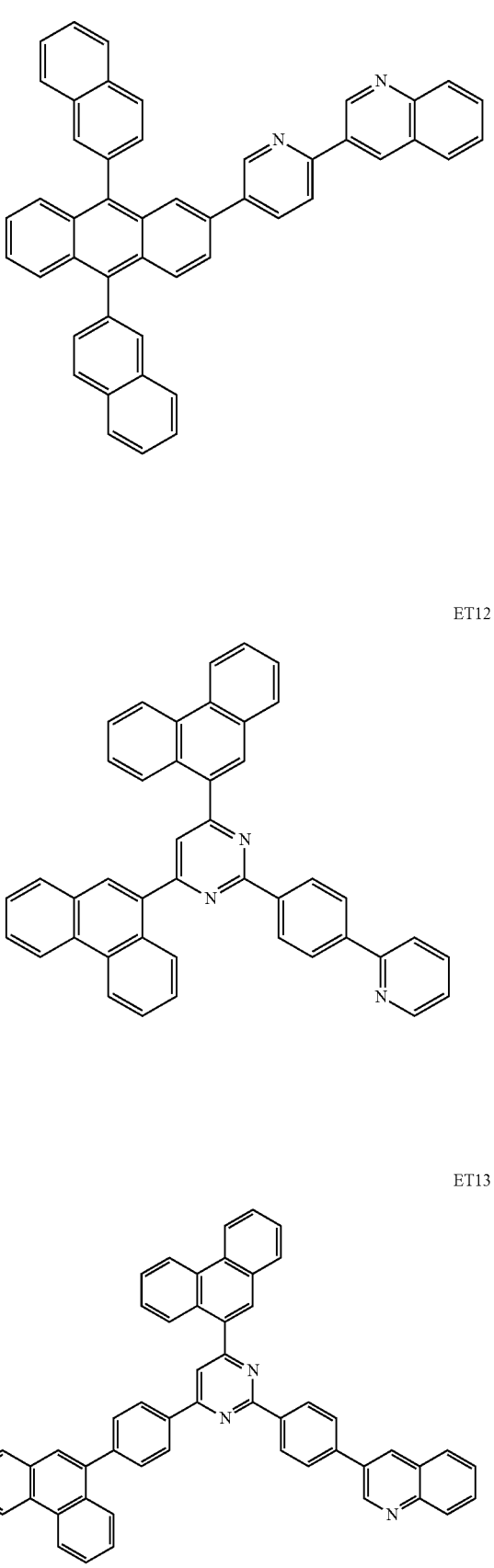

ET14

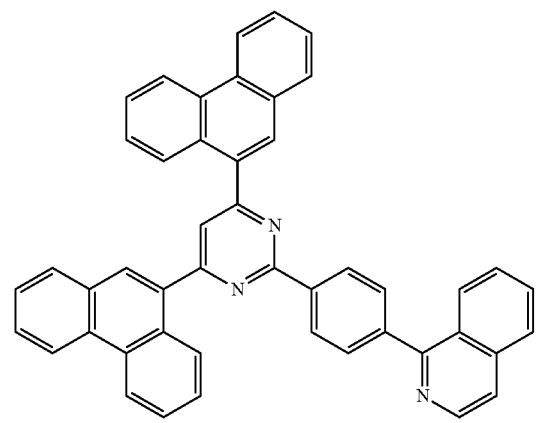

ET15

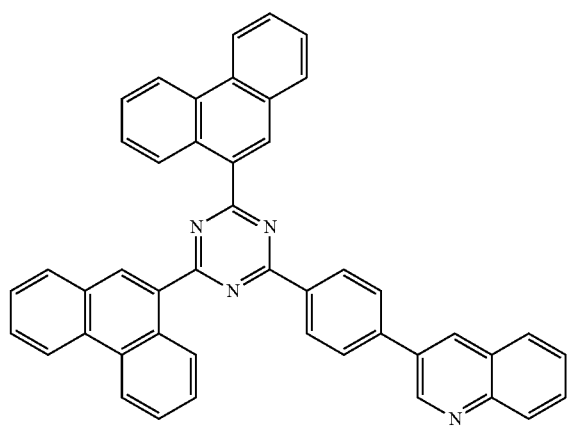

In some embodiments, the electron transport layer may include at least one selected from BCP, Bphen, Alq₃, BAlq, TAZ, and NTAZ.

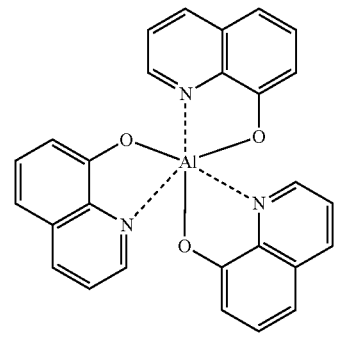

Alq₃

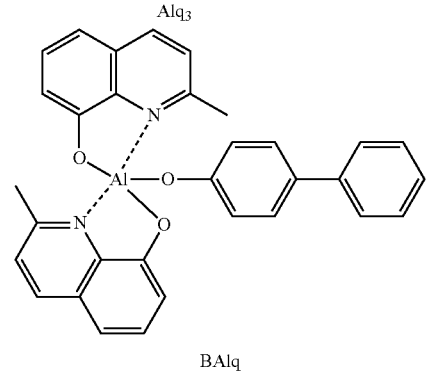

BAlq

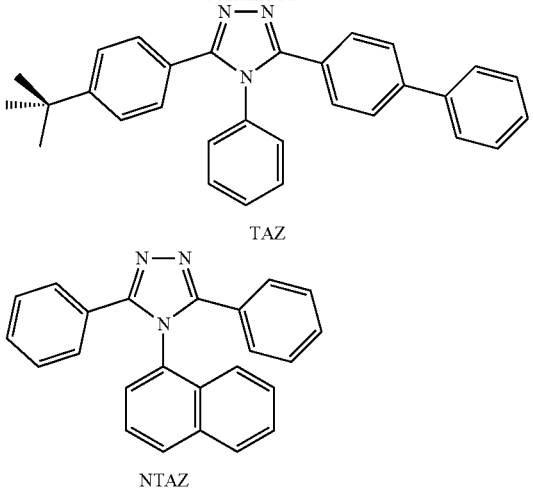

TAZ

NTAZ

A thickness of the electron transport layer may be in a range of about 100 Å to about 1000 Å, or, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET-D1

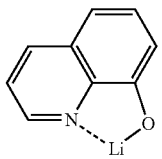

ET-D2

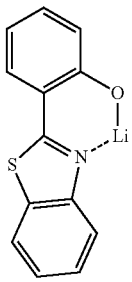

The electron transport region may include an electron injection layer that facilitates electron injection from the second electrode 190.

The electron injection layer may be formed on the electron transport layer by a suitable method, such as vacuum-deposition, spin coating, casting, LB method, ink-jet printing, laser-printing, or LITI. When the electron injection layer is formed by vacuum-deposition or spin coating, vacuum-deposition and coating conditions for the electron injection layer may be determined by referring to the vacuum-deposition and coating conditions for the hole injection layer.

The electron injection layer may include at least one selected from, LiF, NaCl, CsF, Li$_2$O, BaO, and LiQ.

A thickness of the electron injection layer may be in a range of about 1 Å to about 100 Å, or, for example, about 3 Å to about 90 Å. When the thickness of the electron injection layer is within this range, excellent electron injection characteristics may be obtained without a substantial increase in driving voltage.

The second electrode 190 is disposed on the organic layer 150. The second electrode 190 may be a cathode that is an electron injection electrode, and in this regard, a material for forming the second electrode 190 may be a material having a low work function. Such a material may be metal, alloy, an electrically conductive compound, or a mixture thereof. Detailed examples of the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO or IZO. The second electrode 190 may be a semi-transmissive electrode or a transmissive electrode.

The organic light-emitting device has been described with reference to FIG. 1. It is to be understood that the organic light-emitting device may have other suitable structures.

The term "$C_1$-$C_{60}$ alkyl group" used herein refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" used herein refers to a divalent group having the same structure as a $C_1$-$C_{60}$ alkyl group.

The term "$C_1$-$C_{60}$ alkoxy group" used herein refers to a monovalent group represented by -OA$_{101}$ (wherein A$_{101}$ is the $C_1$-$C_{60}$ alkyl group). Examples thereof include a methoxy group, an ethoxy group and an isopropyloxy group.

The term "$C_2$-$C_{60}$ alkenyl group" used herein refers to a hydrocarbon group formed by substituting at least one carbon double bond in the middle or at the terminal of the $C_2$-$C_{60}$ alkyl group. Examples thereof include an ethenyl group, a propenyl group, and a butenyl group. The term "$C_2$-$C_{60}$ alkenylene group" used herein refers to a divalent group having the same structure as a $C_2$-$C_{60}$ alkenyl group.

The term "$C_2$-$C_{60}$ alkynyl group" used herein refers to a hydrocarbon group formed by substituting at least one carbon triple bond in the middle or at the terminal of the $C_2$-$C_{60}$ alkyl group. Examples thereof include an ethynyl group and a propynyl group. The term "$C_2$-$C_{60}$ alkynylene group" used herein refers to a divalent group having the same structure as a $C_2$-$C_{60}$ alkynyl group.

The term "$C_3$-$C_{10}$ cycloalkyl group" used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" used herein refers to a divalent group having the same structure as a $C_3$-$C_{10}$ cycloalkyl group.

The term "$C_1$-$C_{10}$ heterocycloalkyl group" used herein refers to a monovalent monocyclic group including at least one hetero atom selected from N, O, Si, P, and S as a ring-forming atom and 1 to 10 carbon atoms. Examples thereof include a tetrahydrofuranyl group and a tetrahydrothiophenyl group. The term "$C_1$-$C_{10}$ heterocycloalkylene group" used herein refers to a divalent group having the same structure as a $C_1$-$C_{10}$ heterocycloalkyl group.

The term "$C_3$-$C_{10}$ cycloalkenyl group" used herein refers to a monovalent monocyclic group that has 3 to 10 carbon atoms and at least one double bond in its ring, and which is not aromatic. Examples thereof include a cyclopentenyl group, a cyclohexenyl group, and a cycloheptenyl group. The term "$C_3$-$C_{10}$ cycloalkenylene group" used herein refers to a divalent group having the same structure as a $C_3$-$C_{10}$ cycloalkenyl group.

The term "$C_1$-$C_{10}$ heterocycloalkenyl group" used herein refers to a monovalent monocyclic group including at least one hetero atom selected from N, O, Si, P, and S as a ring-forming atom, 1 to 10 carbon atoms, and at least one double bond in its ring. Examples of the $C_1$-$C_{10}$ heterocycloalkenyl group include a 2,3-hydrofuranyl group and a 2,3-hydrothiophenyl group. The term "$C_1$-$C_{10}$ heterocycloalkenylene group" used herein refers to a divalent group having the same structure as a $C_1$-$C_{10}$ heterocycloalkenyl group.

The term "$C_6$-$C_{60}$ aryl group" used herein refers to a monovalent group including a carbocyclic aromatic system having 6 to 60 carbon atoms. The term "$C_6$-$C_{60}$ arylene group" used herein refers to a divalent group including a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group or the $C_6$-$C_{60}$ arylene group include a plurality of rings, the rings may be fused to each other.

The term "$C_1$-$C_{60}$ heteroaryl group" used herein refers to a monovalent group having a carbocyclic aromatic system including at least one hetero atom selected from N, O, Si, P, and S as a ring-forming atom and 1 to 60 carbon atoms. The term "$C_1$-$C_{60}$ heteroarylene group" used herein refers to a divalent group having a carbocyclic aromatic system including at least one hetero atom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group or the $C_1$-$C_{60}$ heteroarylene group include a plurality of rings, the rings may be fused to each other.

The term "$C_6$-$C_{60}$ aryloxy group" used herein indicates -OA$_{102}$ (wherein A$_{102}$ is the $C_6$-$C_{60}$ aryl group), and a $C_6$-$C_{60}$ arylthio group used herein indicates -SA$_{103}$ (wherein A$_{103}$ is the $C_6$-$C_{60}$ aryl group).

The term "monovalent non-aromatic condensed polycyclic group" used herein refers to a monovalent group that has two or more rings condensed to each other, only carbon atoms (for example, the number of carbon atoms may be in a range of 8 to 60) as ring forming atoms, wherein the molecular structure as a whole is non-aromatic in the entire molecular structure. An example of the monovalent non-aromatic condensed polycyclic group is a fluorenyl group. The term "divalent non-aromatic condensed polycyclic group" used herein refers to a divalent group having the same structure as the monovalent non-aromatic condensed polycyclic group.

The term "monovalent non-aromatic condensed heteropolycyclic group" used herein refers to a monovalent group that has a plurality of rings condensed to each other and a hetero atom selected from N, O, P, Si, and S, other than carbon atoms (for example, the number of carbon atoms may be in a range of 2 to 60), as a ring-forming atom, wherein the molecular structure as a whole is non-aromatic in the entire molecular structure. The monovalent non-aromatic condensed heteropolycyclic group may be a carbazolyl group, for example. The term "divalent non-aromatic condensed hetero-polycyclic group" used herein refers to a divalent group having the same structure as the monovalent non-aromatic condensed hetero-polycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$ and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

"Ph" used herein refers to a phenyl group, "Me" refers to a methyl group. "Et" refers to an ethyl group, and "ter-Bu" or "Bu" refers to a tert-butyl group.

Hereinafter, an organic light-emitting device according to an embodiment will be described in detail with reference to Synthesis Examples and Examples. The term "B was used instead of A" used in describing Synthesis Examples denotes that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1

Synthesis of Compound 4

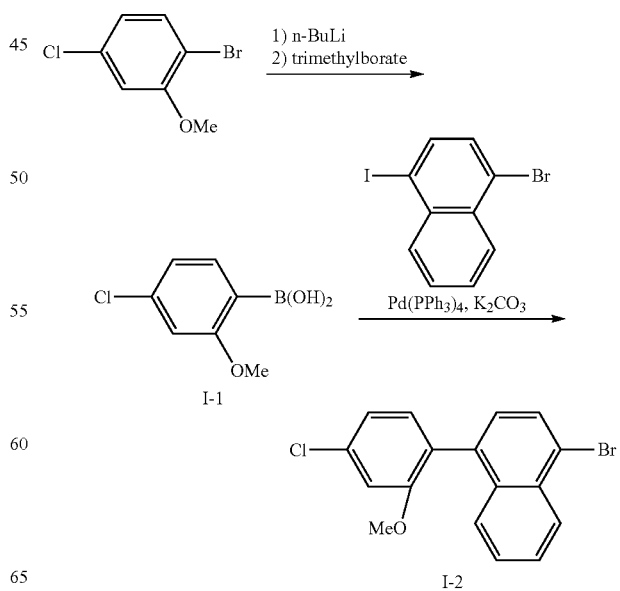

Synthesis of Intermediate I-1

22.1 g (100 mmol) of 2-bromo-5-chloroanisole was dissolved in 500 ml of THF, and stirred in a $N_2$ atmosphere at −78° C. for 10 minutes. Then, 44 mL of 2.5 M n-BuLi was slowly added thereto by using a dropping funnel, and the mixture was additionally stirred for 30 minutes. 10.4 g (110 mmol) of trimethyl borate was slowly and dropwisely added thereto by using a dropping funnel, and the mixture was additionally stirred for 3 hours at room temperature. Next, an organic layer was extracted therefrom once by using 300 ml of 1 M HCl and three times by using water and diethylether. The organic layer was dried using magnesium sulfate, and a solvent was removed thereform by evaporation. The residue was separated and purified through a silica gel chromatography to obtain 13.61 g of Intermediate I-1 (73 mmol, yield: 73%). The compound thus obtained was confirmed by using MS/FAB.

$C_7H_8BClO_3$ Cal. 186.40, Found. 186.47.

Synthesis of Intermediate I-2

13.61 g (73 mmol) of Intermediate I-1, 36.6 g (110 mmol) of 1-bromo-4-iodonaphthalene, 8.67 g (7.5 mmol) of $Pd(PPh_3)_4$, and 31.1 g (225 mmol) of $K_2CO_3$ were added to 1 L of $THF/H_2O$ (at a volume ratio of 9:1)solution, and stirred at 80° C. for 12 hours. The reaction mixture was cooled to room temperature, and an organic layer was extracted therefrom three times by using 500 mL of water and 500 mL of diethylether. The organic layer was dried using magnesium sulfate, and a solvent was removed thereform by evaporation. The residue was separated and purified through a silica gel chromatography to obtain 17.73 g of Intermediate I-2 (51 mmol, yield: 70%). The compound thus obtained was confirmed by using MS/FAB.

$C_7H_8BClO_3$ Cal. 347.64, Found. 347.71.

Synthesis of Compound 4

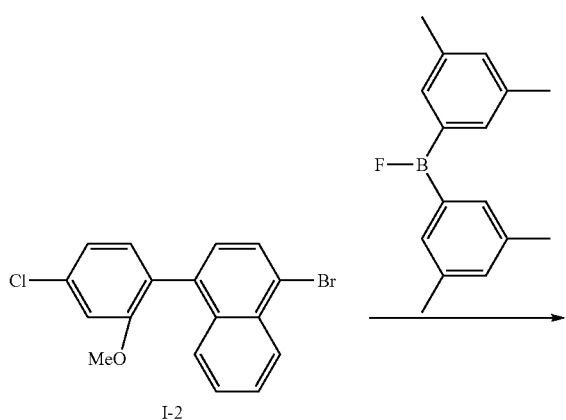

I-2

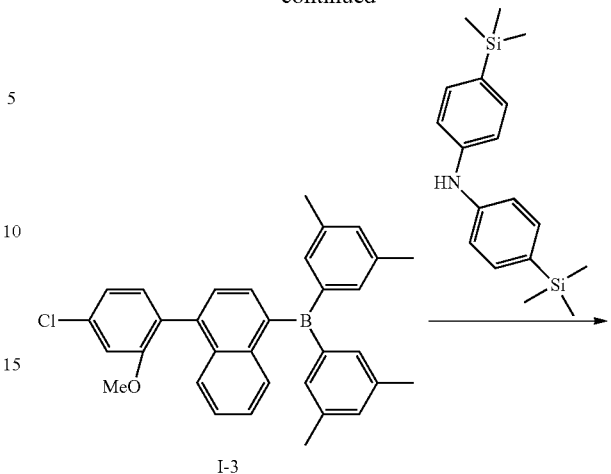

I-3

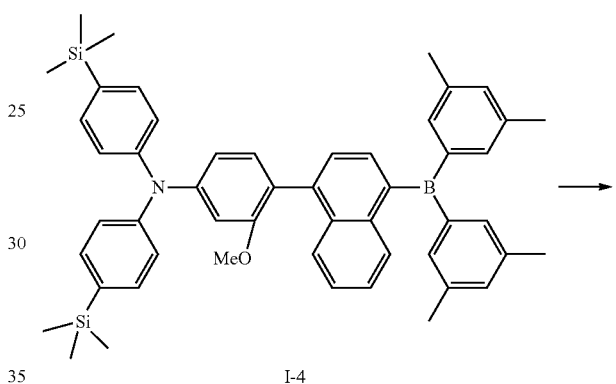

I-4

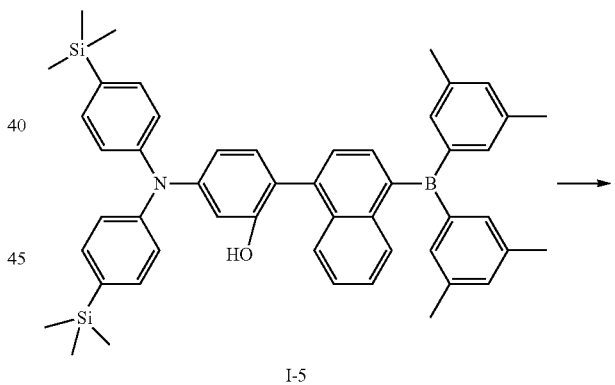

I-5

4

Synthesis of Intermediate I-3

3.47 g (10 mmol) of Intermediate I-2 was dissolved in 500 mL of THF, and 4 mL of n-BuLi (2.5 M in hexane) was added thereto and stirred at −78° C. Then, a solution prepared by dissolving 2.40 g (10 mmol) of bis(3,5-dimethylphenyl)fluoroborane in 10 mL of THF was slowly and dropwisely added to the reaction mixture, stirred for 3 hours, and cooled to room temperature. Water was added to the reaction mixture, and an organic layer was extracted three times by using 30 mL of ethylacetate. The organic layer was dried using magnesium sulfate, and a solvent was removed therefrom by evaporation. The residue was separated and purified through a silica gel chromatography to obtain 3.72 g of Intermediate I-3 (yield: 76%). The compound thus obtained was confirmed by using MS/FAB.

$C_{33}H_{30}BClO$ Cal. 488.86, Found. 488.75.

Synthesis of Intermediate I-4

2.45 g (5 mmol) of Intermediate I-3, 1.57 g (5 mmol) of bis(4-(trimethylsilyl)phenyl)amine, 0.09 g (0.1 mmol) of $Pd_2(dba)_3$, 0.01 g (0.1 mmol) of $PtBu_3$, and 0.72 g (7.5 mmol) of NaOtBu were dissolved in 8 mL of toluene and reflux-stirred at 85° C. for 4 hours. The reaction mixture was cooled to room temperature, and an organic layer was extracted therefrom three times by using 50 mL of water and 50 mL of diethylether. The organic layer was dried using magnesium sulfate, and a solvent was removed therefrom by evaporation. The residue was separated and purified through a silica gel chromatography to obtain 3.06 g of Intermediate I-4 (yield: 80%). The compound thus obtained was confirmed by using MS/FAB.

$C_{51}H_{55}BNOSi_2$ Cal. 765.99, Found. 765.87.

Synthesis of Intermediate I-5

3.83 g (5 mmol) of Intermediate I-4 was dissolved in 50 mL of methylenechloride (MC), and 0.7 mL (7.5 mmol) of $BBr_3$ was slowly and dropwisely added thereto at −78° C. The reaction mixture was heated to room temperature and was stirred for 24 hours at room temperature. When the reaction was completed, 15 mL of MeOH and 30 mL of $H_2O$ were added thererto, and an organic layer was extracted therefrom three times by using 30 mL of MC. The organic layer was dried using magnesium sulfate, and a solvent was removed therefrom by evaporation. The residue was separated and purified through a silica gel chromatography to obtain 3.38 g of Intermediate I-5 (yield: 80%). The compound thus obtained was confirmed by using MS/FAB.

$C_{50}H_{54}BNOSi_2$ Cal. 751.97, Found. 751.87.

Synthesis of Compound 14

3.76 g (5 mmol) of Intermediate I-5 and 3.58 g (25 mmol) of $Cu_2O$ (copper(I) oxide) were dissolved in 50 mL of nitrobenzene, and the mixture was reflux-stirred at 180° C. for 12 hours. Then, after evaporating of a solvent therefrom, an organic layer was extracted three times by using 30 mL of $H_2O$ and 30 mL of MC, the organic layer was dried using magnesium sulfate, and a solvent was removed therefrom by evaporation. The residue was separated and purified through a silica gel chromatography to obtain 3.18 g of Compound 4 (yield: 85%). The compound thus obtained was confirmed by using MS/FAB and 1H NMR.

$C_{50}H_{52}BNOSi_2$ Cal. 749.95, Found. 749.87.

Synthesis Example 2

Synthesis of Compound 11

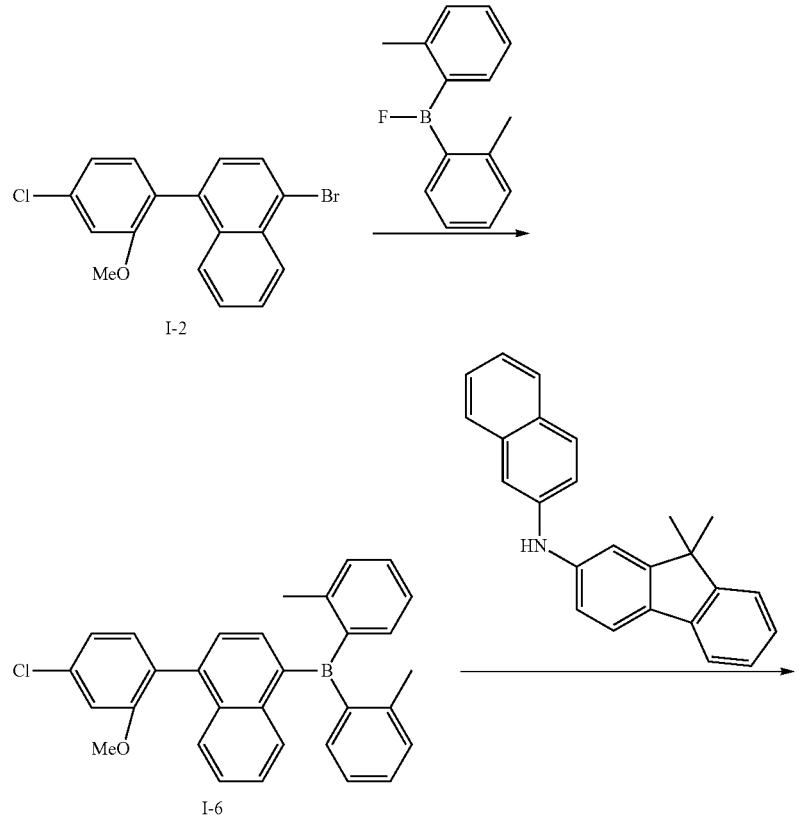

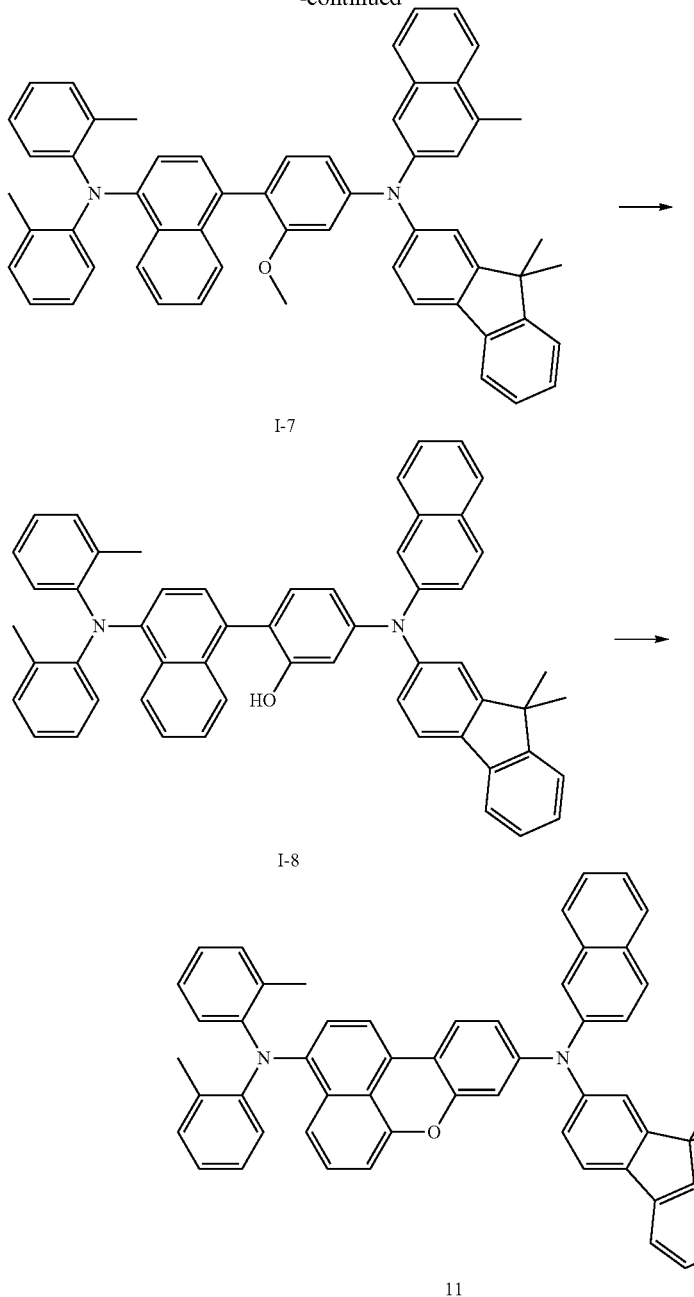

Synthesis of Intermediate I-6

3.32 g (yield: 72%) of Intermediate I-6 was prepared in the same manner as in the synthesis of Intermediate I-3, except that fluorodi-ortho-tolylborane was used instead of bis(3,5-dimethylphenyl)fluoroborane. The compound thus obtained was confirmed by using MS/FAB.

$C_{31}B_{26}BClO$ Cal. 460.81, Found. 460.98.

Synthesis of Intermediate I-7

12 g (yield: 82%) of Intermediate I-7 was prepared in the same manner as in the synthesis of Intermediate I-4, except that Intermediate I-6 was used instead of Intermediate I-3 and 9,9-dimethyl-N-(naphthalen-2-yl)-9H-fluoren-2-amine instead of bis(4-(trimethylsilyl)phenyl)amine. The compound thus obtained was confirmed by using MS/FAB.

$C_{56}H_{46}BNO$ Cal. 759.80, Found. 759.75.

Synthesis of Intermediate I-8

3.47 g (yield: 93%) of Intermediate I-8 was prepared in the same manner as in the synthesis of Intermediate I-5, except that Intermediate I-7 was used instead of Intermediate I-4. The compound thus obtained was confirmed by using MS/FAB.

$C_{55}H_{44}BNO$ Cal. 745.77, Found. 745.75

Synthesis of Compound 11

3.16 g (yield: 85%) of Compound 11 was prepared in the same manner as in the synthesis of Compound 4, except that Intermediate I-8 was used instead of Intermediate I-5. The compound thus obtained was confirmed by using MS/FAB and 1H NMR.

$C_{55}H_{42}BNO$ Cal. 743.76, Found. 743.57.

Synthesis Example 3

Synthesis of Compound 22

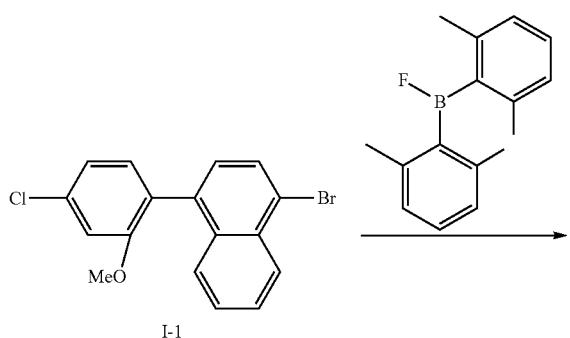

I-1

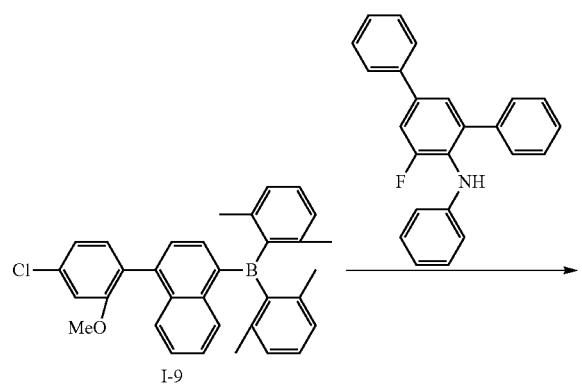

I-9

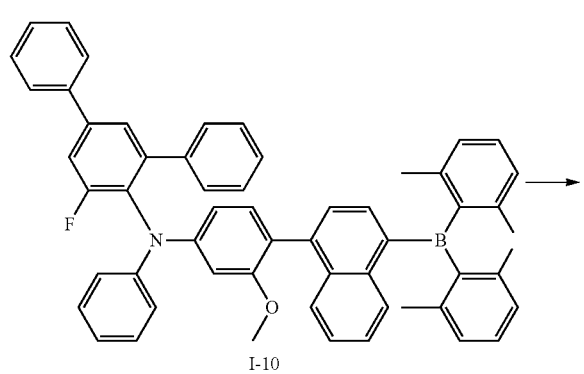

I-10

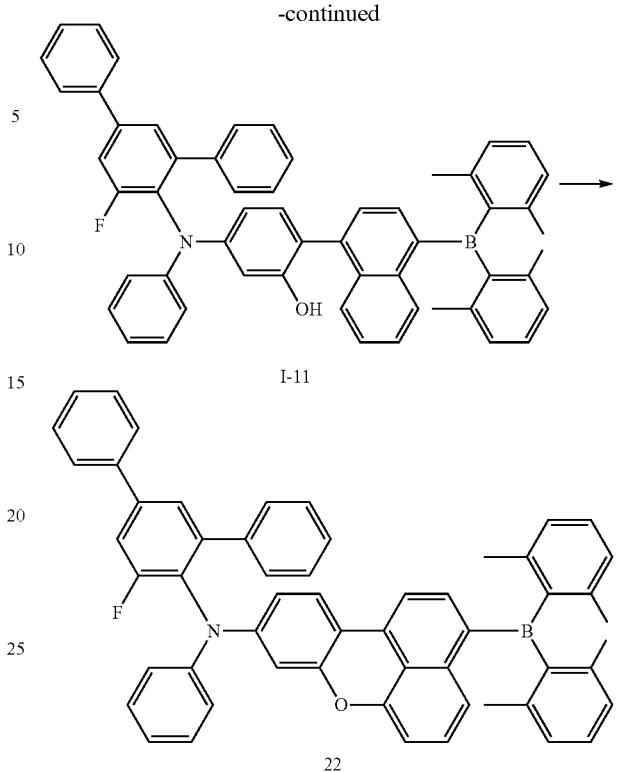

I-11

22

Synthesis of Intermediate I-9

3.81 g (yield: 78%) of Intermediate I-9 was prepared in the same manner as in the synthesis of Intermediate I-3, except that bis(2,6-dimethylphenyl)fluoroborane was used instead of bis(3,5-dimethylphenyl)fluoroborane. The compound thus obtained was confirmed by using MS/FAB.

$C_{31}H_{26}BClO$ Cal. 488.86, Found. 488.85.

Synthesis of Intermediate I-10

3.13 g (yield: 79%) of Intermediate I-10 was prepared in the same manner as in the synthesis of Intermediate I-4, except that Intermediate I-9 was used instead of Intermediate I-3 and 5'-fluoro-N-phenyl-[1,1':3',1''-terphenyl]-4'-amine instead of bis(4-(trimethylsilyl) phenyl)amine. The compound thus obtained was confirmed by using MS/FAB.

$C_{57}H_{47}BFNO$ Cal. 791.82 Found. 791.89.

Synthesis of Intermediate I-11

3.5 g (yield: 90%) of Intermediate I-11 was prepared in the same manner as in the synthesis of Intermediate I-5, except that Intermediate I-10 was used instead of Intermediate I-4. The compound thus obtained was confirmed by using MS/FAB.

$C_{56}H_{45}BFNO$ Cal. 777.79, Found. 777.35.

Synthesis of Compound 22

3.37 g (yield: 87%) of Compound 22 was prepared in the same manner as in the synthesis of Compound 4, except that Intermediate I-11 was used instead of Intermediate I-5. The compound thus obtained was confirmed by using MS/FAB and 1H NMR.

$C_{56}H_{43}BFNO$ Cal. 775.77, Found. 775.47'.

Synthesis Example 4
Synthesis of Compound 34
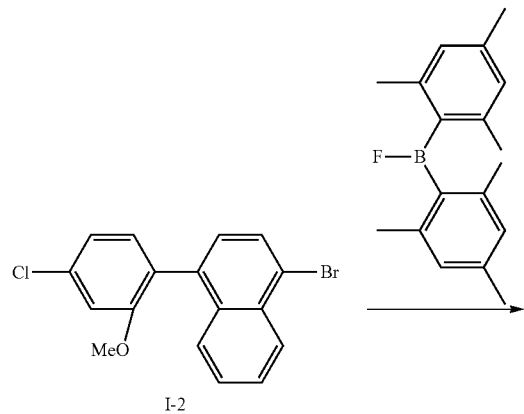
I-2
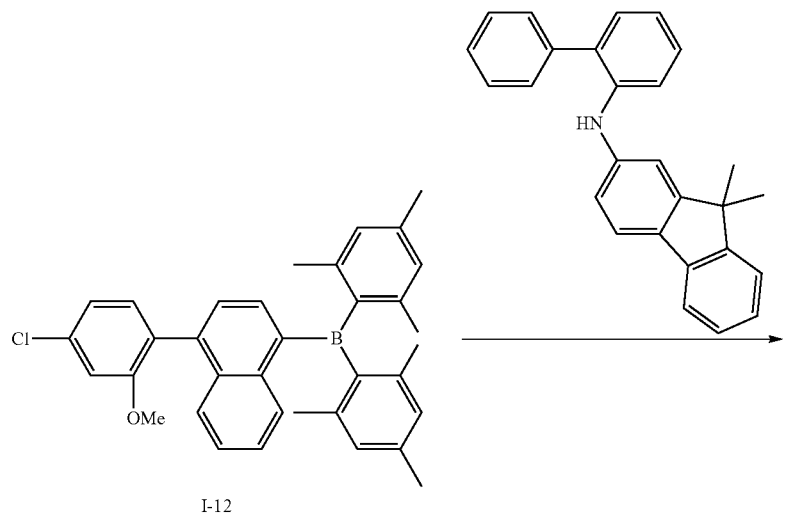
I-12
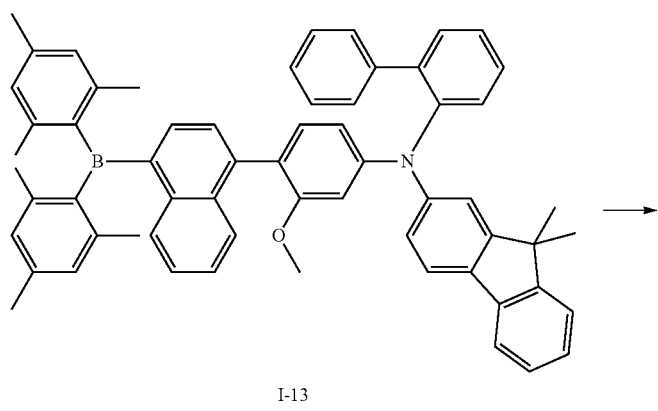
I-13

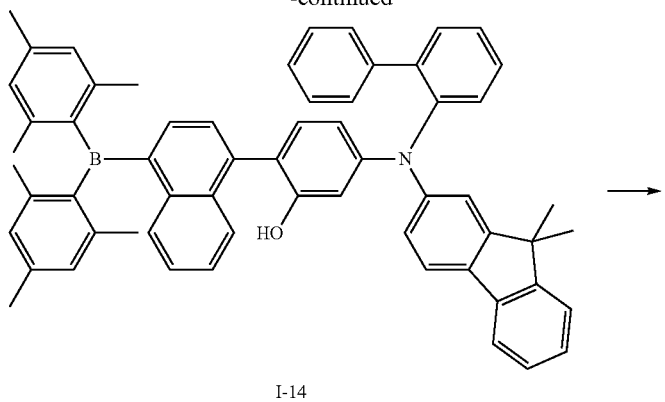

I-14

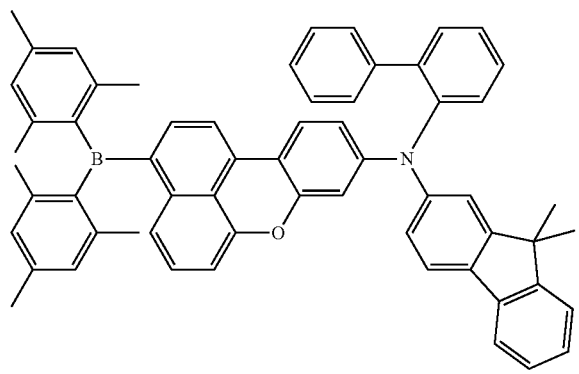

34

Synthesis of Intermediate I-12

3.88 g (yield: 75%) of Intermediate I-12 was prepared in the same manner as in the synthesis of Intermediate I-3, except that fluorodimethylborane was used instead of bis(3,5-dimethylphenyl)fluoroborane.

$C_{35}H_{34}BClO$ Cal. 516.92, Found. 516.98.

Synthesis of Intermediate I-13

2.99 g (yield: 71%) of Intermediate I-13 was prepared in the same manner as in the synthesis of Intermediate I-4, except that Intermediate I-12 was used instead of Intermediate I-13 and N-([1,1'-biphenyl]-2-yl)-9,9-dimethyl-9H-fluoren-2-amine instead of bis(4-(trimethylsilyl)phenyl)amine. The compound thus obtained was confirmed by using MS/FAB.

$C_{62}H_{56}BNO$ Cal. 841.95 Found. 841.98.

Synthesis of Intermediate I-14

3.52 g (yield: 85%) of Intermediate I-14 was prepared in the same manner as in the synthesis of Intermediate I-5, except that Intermediate I-13 was used instead of Intermediate I-4. The compound thus obtained was confirmed by using MS/FAB.

$C_{61}H_{54}BNO$ Cal. 827.92, Found. 827.98.

Synthesis of Compound 34

3.34 g (yield: 81%) of Compound 34 was prepared in the same manner as in the synthesis of Compound 4, except that Intermediate I-11 was used instead of Intermediate I-5. The compound thus obtained was confirmed by using MS/FAB and 1H NMR.

$C_{61}H_{52}BNO$ Cal. 825.90, Found. 825.92.

Synthesis Example 5

Synthesis of Compound 37

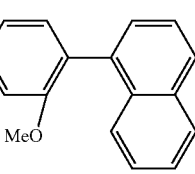

I-2

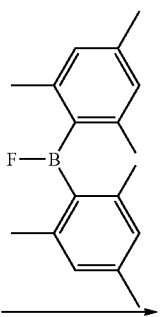

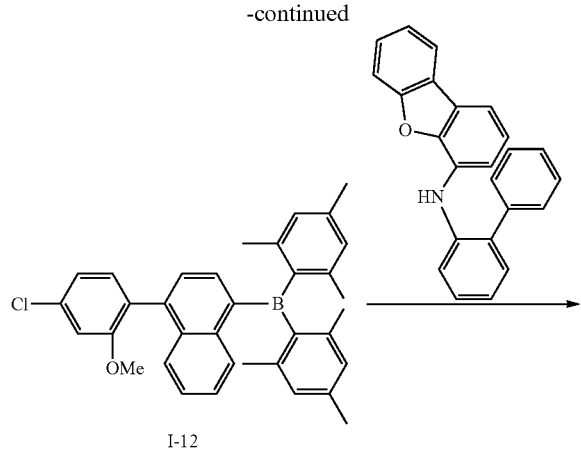

I-12

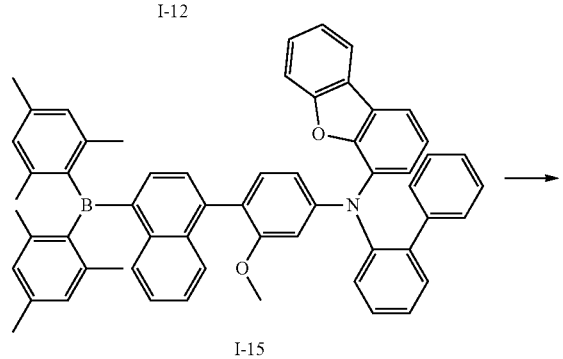

I-15

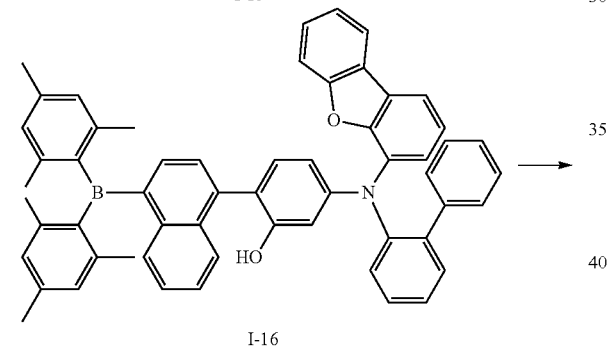

I-16

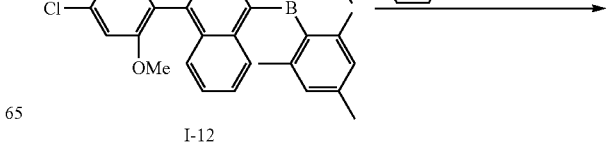

37

Synthesis of Intermediate I-15

2.98 g (yield: 73%) of Intermediate I-15 was prepared in the same manner as in the synthesis of Intermediate I-4, except that Intermediate I-12 was used instead of Intermediate I-3 and N-([1,1'-biphenyl]-2-yl)dibenzo[b,d]furan-4-amine instead of bis(4-(trimethylsilyl)phenyl)amine. The compound thus obtained was confirmed by using MS/FAB.

$C_{59}H_{50}BNO_2$ Cal. 815.86 Found. 815.97.

Synthesis of Intermediate I-16

3.57 g (yield: 89%) of Intermediate I-16 was prepared in the same manner as in the synthesis of Intermediate I-5, except that Intermediate I-15 was used instead of Intermediate I-4. The compound thus obtained was confirmed by using MS/FAB.

$C_{58}H_{48}BNO_2$ Cal. 801.84 Found. 801.80.

Synthesis of Compound 37

3.28 g (yield: 82%) of Compound 37 was prepared in the same manner as in the synthesis of Compound 4, except that Intermediate I-16 was used instead of Intermediate I-5. The compound thus obtained was confirmed by using MS/FAB and 1H NMR.

$C_{58}H_{46}BNO_2$ Cal. 799.82, Found. 799.82.

Synthesis Example 6

Synthesis of Compound 44

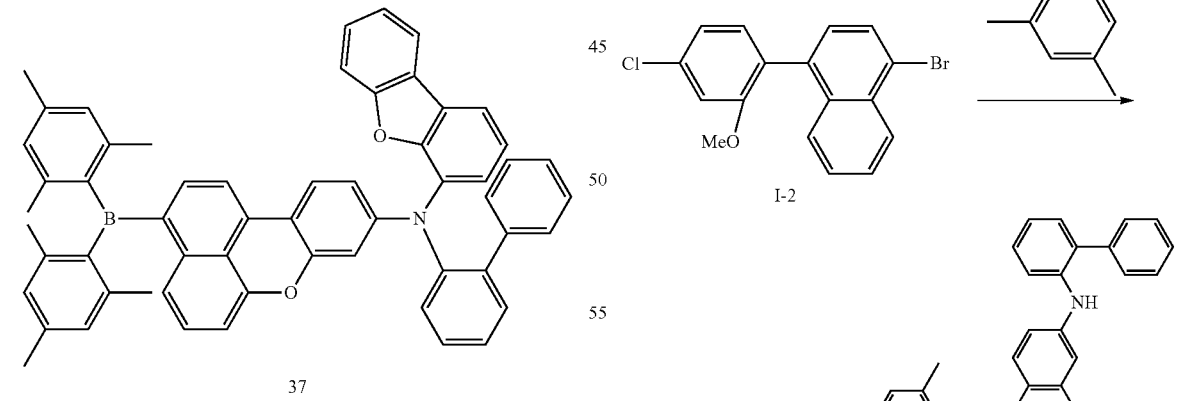

I-2

I-12

-continued

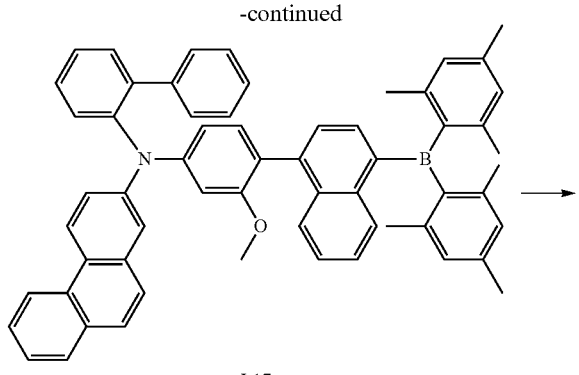

I-17

I-18

44

Synthesis of Intermediate I-17

3.22 g (yield: 78%) of Intermediate I-17 was prepared in the same manner as in the synthesis of Intermediate I-4, except that Intermediate I-12 was used instead of Intermediate I-3 and N-([1,1'-biphenyl]-2-yl)phenanthren-2-amine instead of bis(4-(trimethylsilyl)phenyl)amine. The compound thus obtained was confirmed by using MS/FAB.

$C_{61}H_{52}BNO$ Cal. 825.90 Found. 825.95.

Synthesis of Intermediate I-18

3.69 g (yield: 91%) of Intermediate I-18 was prepared in the same manner as in the synthesis of Intermediate I-4, except that Intermediate I-17 was used instead of Intermediate I-4. The compound thus obtained was confirmed by using MS/FAB.

$C_{60}H_{50}BNO$ Cal. 811.88 Found. 811.92.

Synthesis of Compound 44

3.52 g (yield: 87%) of Compound 44 was prepared in the same manner as in the synthesis of Compound 4, except that Intermediate I-18 was used instead of Intermediate I-5. The compound thus obtained was confirmed by using MS/FAB and 1H NMR.

$C_{60}H_{48}BNO$ Cal. 809.86, Found. 809.92.

Synthesis Example 7

Synthesis of Compound 55

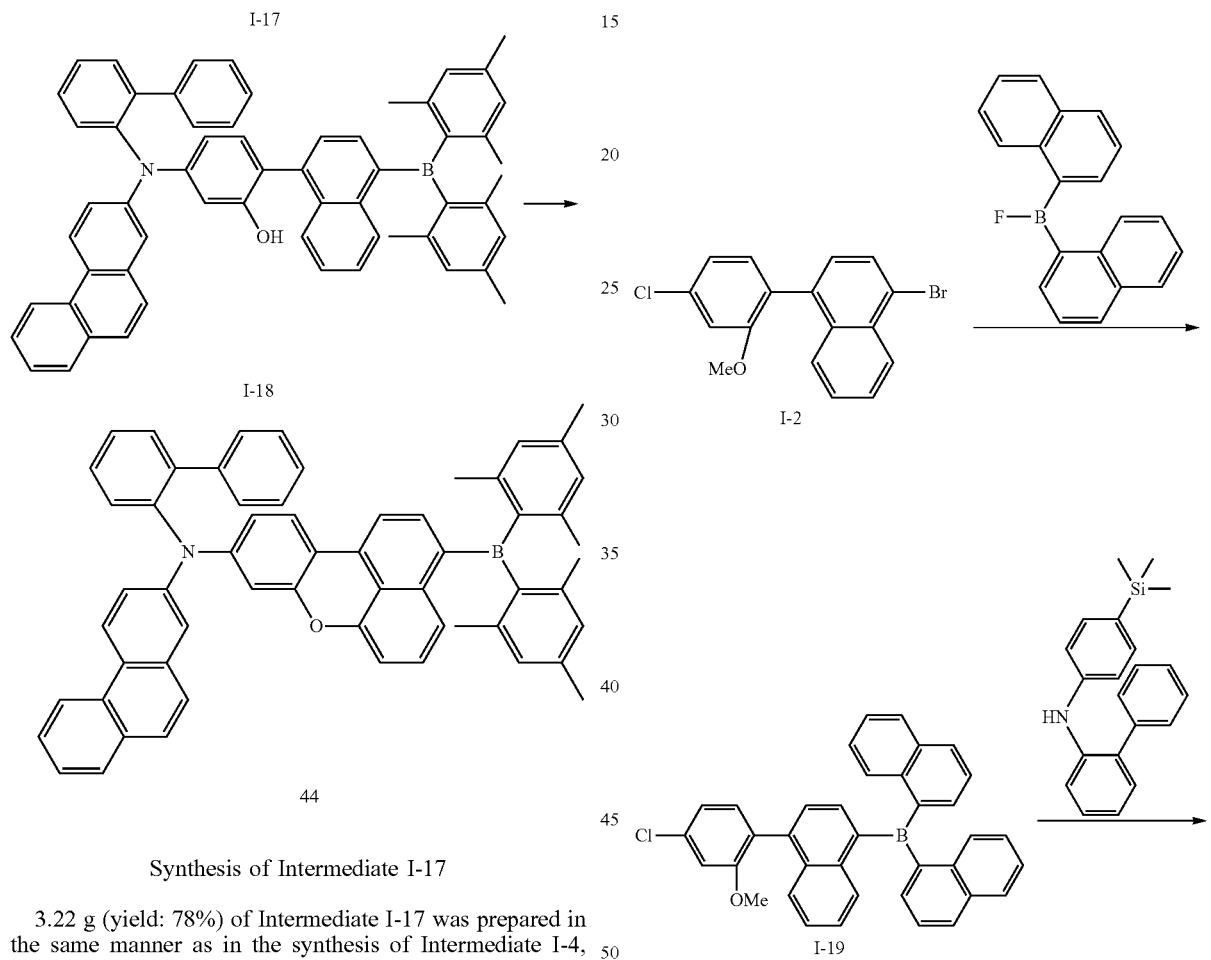

I-2

I-19

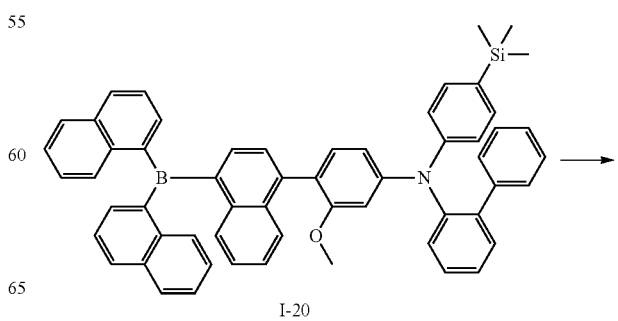

I-20

-continued

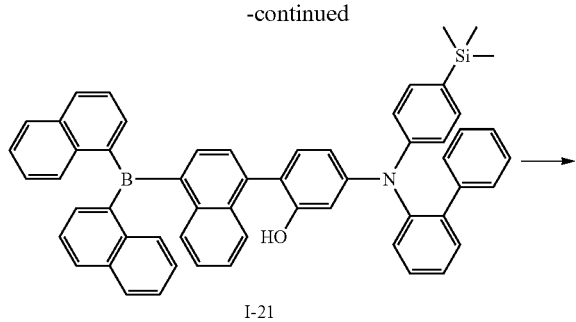

I-21

Synthesis of Intermediate I-20

3.26 g (yield: 80%) of Intermediate I-20 was prepared in the same manner as in the synthesis of Intermediate I-4, except that Intermediate I-17 was used instead of Intermediate I-4 and N-(4-(trimethylsilyl)phenyl)-[1,1'-biphenyl]-2-amine instead of bis(4-(trimethylsilyl)phenyl)amine. The compound thus obtained was confirmed by using MS/FAB.

$C_{58}H_{48}BNOSi$ Cal. 813.92 Found. 813.91.

Synthesis of Intermediate I-21

3.48 g (yield: 87%) of Intermediate I-21 was prepared in the same manner as in the synthesis of Intermediate I-5, except that Intermediate I-20 was used instead of Intermediate I-4. The compound thus obtained was confirmed by using MS/FAB.

$C_{57}H_{48}BNOSi$ Cal. 799.90, Found. 799.92.

Synthesis of Compound 55

3.27 g (yield: 82%) of Compound 55 was prepared in the same manner as in the synthesis of Compound 4, except that Intermediate I-21 was used instead of Intermediate I-5. The compound thus obtained was confirmed by using MS/FAB and 1H NMR.

$C_{57}H_{44}BNOSi$ Cal. 797.88, Found. 797.92.

Synthesis Example 8

Synthesis of Compound 73

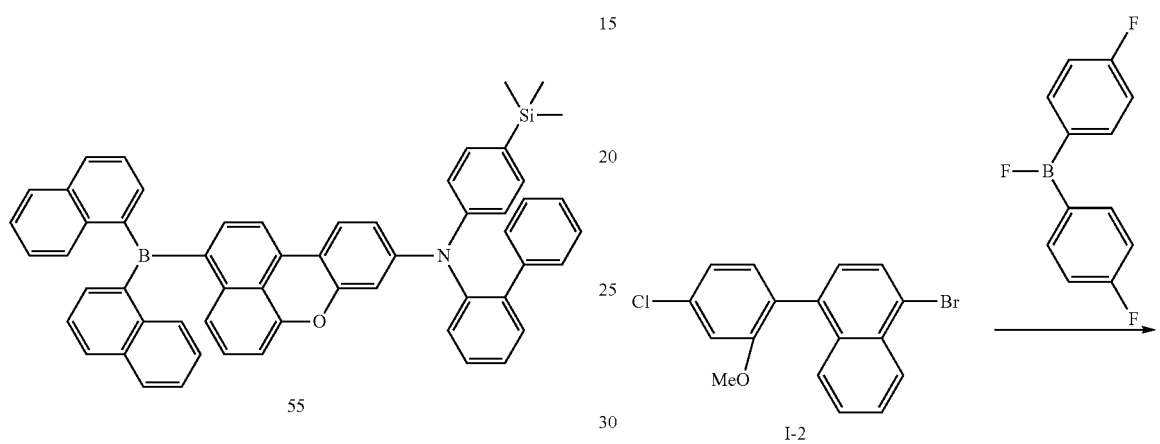

I-2

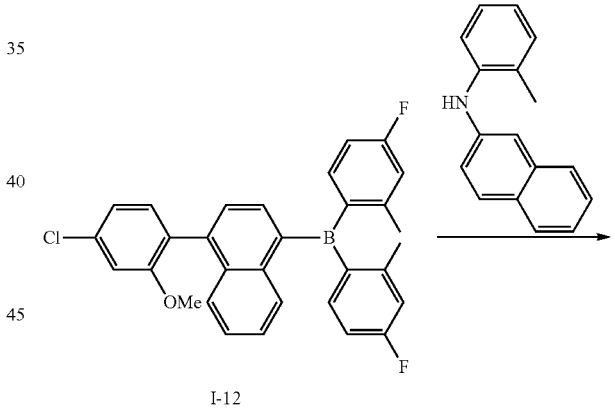

I-12

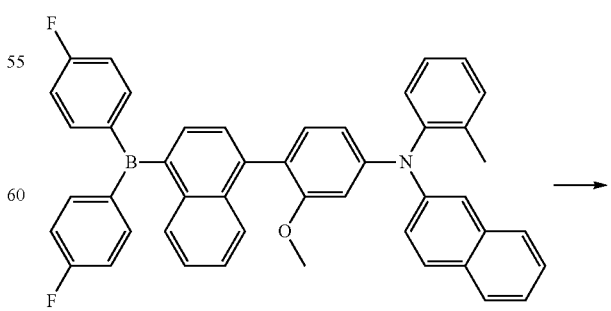

I-23

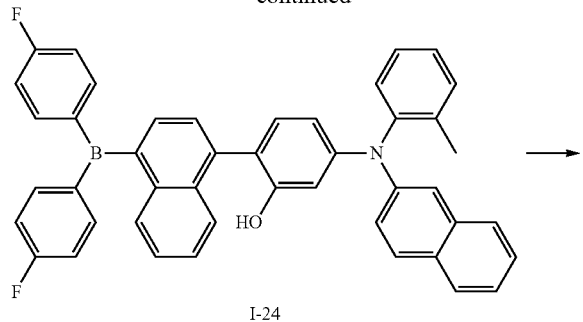

I-24

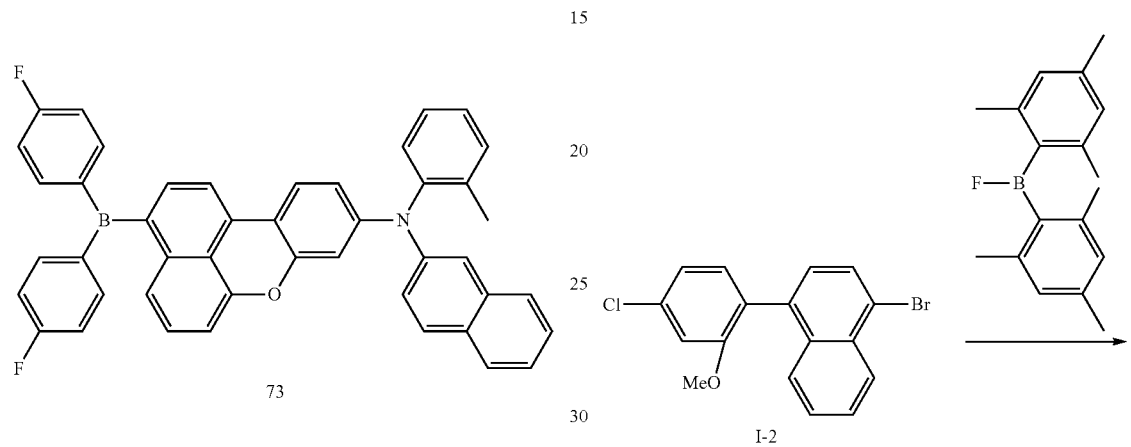

73

Synthesis of Intermediate I-22

3.37 g (yield: 72%) of Intermediate I-22 was prepared in the same manner as in the synthesis of Intermediate I-3, except that fluorobis(4-fluorophenyl)borane was used instead of bis(3,5-dimethylphenyl)fluoroborane. The compound thus obtained was confirmed by using MS/FAB.

$C_{29}H_2OBClF_2O$ Cal. 468.73 Found. 468.82.

Synthesis of Intermediate I-23

2.69 g (yield: 81%) of Intermediate I-23 was prepared in the same manner as in the synthesis of Intermediate I-4, except that Intermediate I-22 was used instead of Intermediate I-3 and N-(o-tolyl)naphthalen-2-amine and bis(4-(trimethylsilyl)phenyl)amine. The compound thus obtained was confirmed by using MS/FAB.

$C_{46}H_{34}BF_2NO$ Cal. 665.59 Found. 665.72

Synthesis of Intermediate I-24

2.70 g (yield: 83%) of Intermediate I-24 was prepared in the same manner as in the synthesis of Intermediate I-5, except that Intermediate I-23 was used instead of Intermediate I-4. The compound thus obtained was confirmed by using MS/FAB.

$C_{45}H_{32}BF_2NO$ Cal. 651.56, Found. 651.58.

Synthesis of Compound 73

2.82 g (yield: 87%) of Compound 73 was prepared in the same manner as in the synthesis of Compound 4, except that Intermediate I-24 was used instead of Intermediate I-5. The compound thus obtained was confirmed by using MS/FAB and 1H NMR.

$C_{45}H_{30}BF_2NO$ Cal. 649.55, Found. 649.75.

Synthesis Example 9

Synthesis of Compound 84

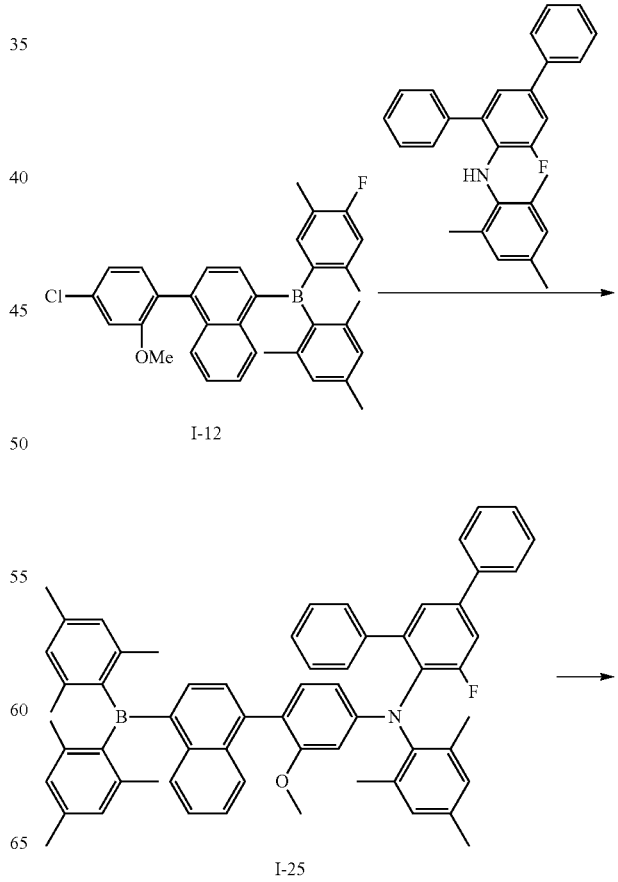

-continued

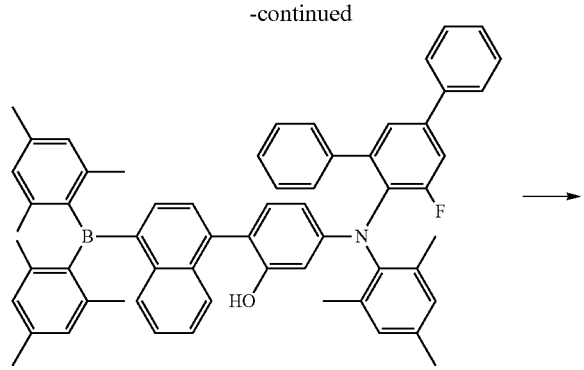

I-26

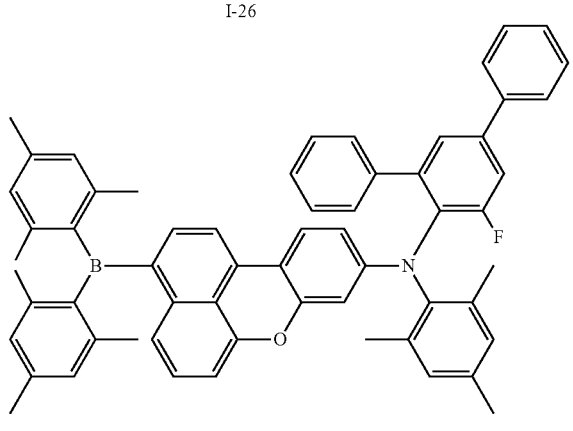

84

Synthesis of Intermediate I-25

3.53 g (yield: 82%) of Intermediate I-25 was prepared in the same manner as in the synthesis of Intermediate I-4, except that Intermediate I-12 was used instead of Intermediate I-3 and 5'-fluoro-N-mesityl-[1,1':3',1''-terphenyl]-4'-amine instead of bis(4-(trimethylsilyl) phenyl)amine. The compound thus obtained was confirmed by using MS/FAB.

$C_{62}H_{57}BFNO$ Cal. 861.95 Found. 861.98.

Synthesis of Intermediate I-26

3.77 g (yield: 89%) of Intermediate I-26 was prepared in the same manner as in the synthesis of Intermediate I-5, except that Intermediate I-25 was used instead of Intermediate I-4. The compound thus obtained was confirmed by using MS/FAB.

$C_{61}H_{55}BFNO$ Cal. 847.44 Found. 847.58.

Synthesis of Compound 84

3.72 g (yield: 88%) of Compound 84 was prepared in the same manner as in the synthesis of Compound 4, except that Intermediate I-26 was used instead of Intermediate I-5. The compound thus obtained was confirmed by using MS/FAB and 1H NMR.

$C_{61}H_{53}BFNO$ Cal. 845.91, Found. 845.91.

Synthesis Example 10

Synthesis of Compound 90

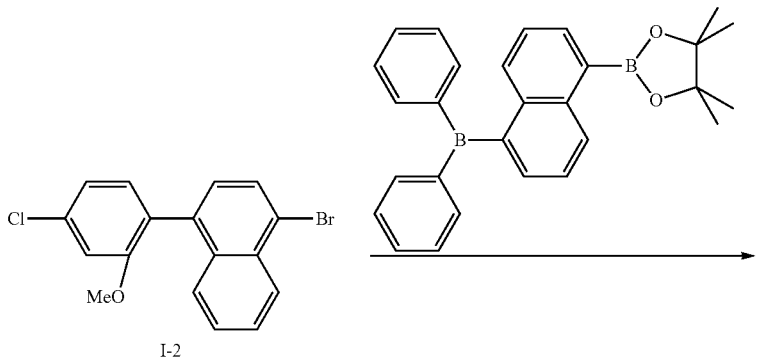

I-2

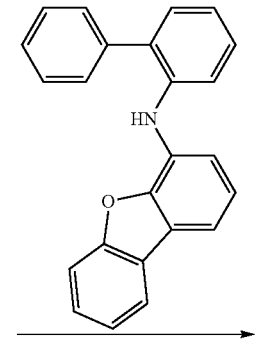

I-27

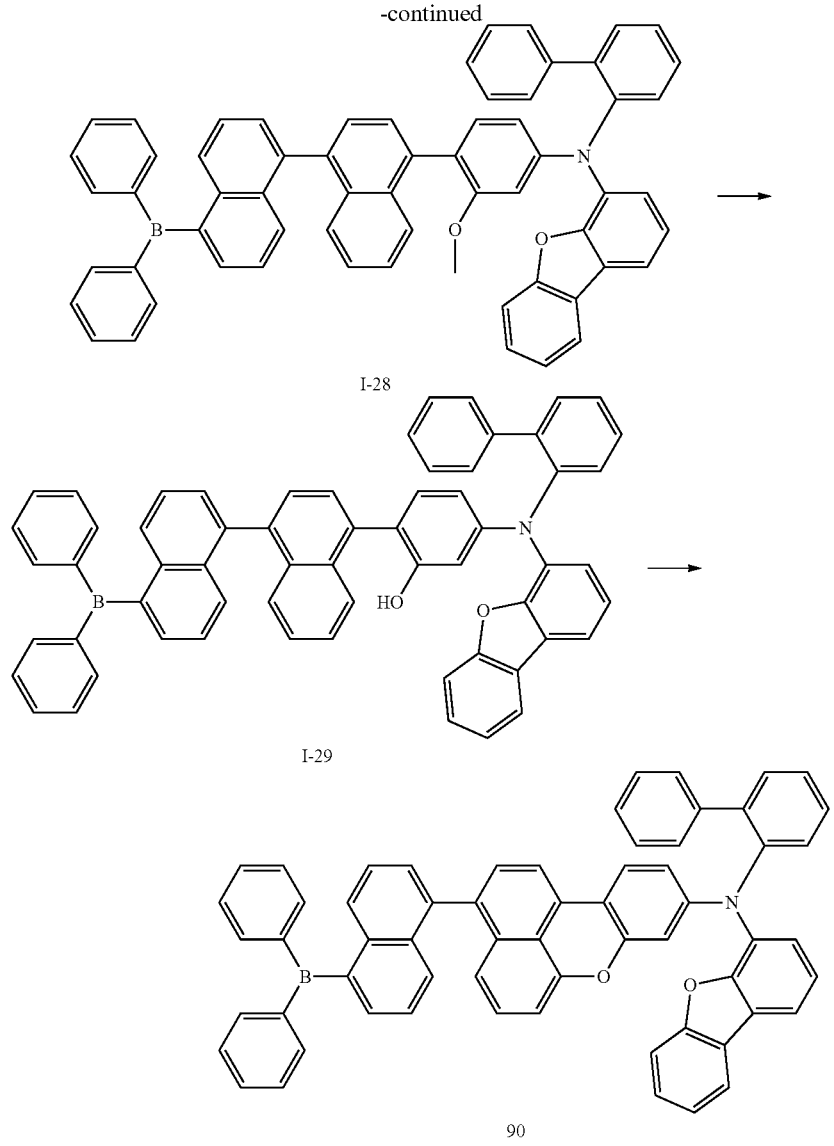

Synthesis of Intermediate I-27

3.48 g (10 mmol) of Intermediate I-2, 4.18 g (10 mmol) of 2-(5-(diphenylboranyl)naphthalen-1-yl)-4,4,5,5-tetramethyl-1,3,2-dioxaborolane, 0.58 g (0.5 mmol) of Pd(PPh$_3$)$_4$, and 2.76 g (20 mmol) of K$_2$CO$_3$ were added to 200 mL of THF/H$_2$O (at a volume ratio of 5:1) solution, and stirred at 80° C. for 12 hours. The reaction mixture was cooled to room temperature, and an organic layer was extracted therefrom three times by using 50 mL of water and 50 mL of diethylether. The organic layer was dried using magnesium sulfate, and a solvent was removed therefrom by evaporation. The residue was separated and purified through a silica gel chromatography to obtain 3.97 g of Intermediate I-27 (yield: 71%). The compound thus obtained was confirmed by using MS/FAB.

C$_{39}$H$_{28}$BClO Cal. 558.91 Found. 558.94.

Synthesis of Intermediate I-28

3.17 g (yield: 74%) of Intermediate I-28 was prepared in the same manner as in the synthesis of Intermediate I-4, except that Intermediate I-27 was used instead of Intermediate I-3 and N-([1,1'-biphenyl]-2-yl)dibenzo[b,d]furan-4-amine instead of bis(4-(trimethylsilyl)phenyl)amine. The compound thus obtained was confirmed by using MS/FAB.

C$_{63}$H$_{44}$BNO$_2$ Cal. 857.86 Found. 857.98.

Synthesis of Intermediate I-29

3.42 g (yield: 81%) of Intermediate I-29 was prepared in the same manner as in the synthesis of Intermediate I-5, except that Intermediate I-28 was used instead of Intermediate I-4. The compound thus obtained was confirmed by using MS/FAB.

C$_{62}$H$_{42}$BNO$_2$ Cal. 843.83 Found. 843.95.

Synthesis of Compound 90

3.54 g (yield: 84%) of Compound 90 was prepared in the same manner as in the synthesis of Compound 4, except that Intermediate I-29 was used instead of Intermediate I-5. The compound thus obtained was confirmed by using MS/FAB and 1H NMR.

C$_{62}$H$_{40}$BNO$_2$ Cal. 841.81, Found. 841.82.

Synthesis Example 11
Synthesis of Compound 96
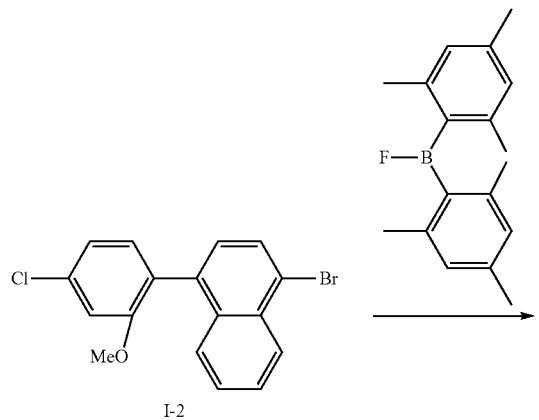
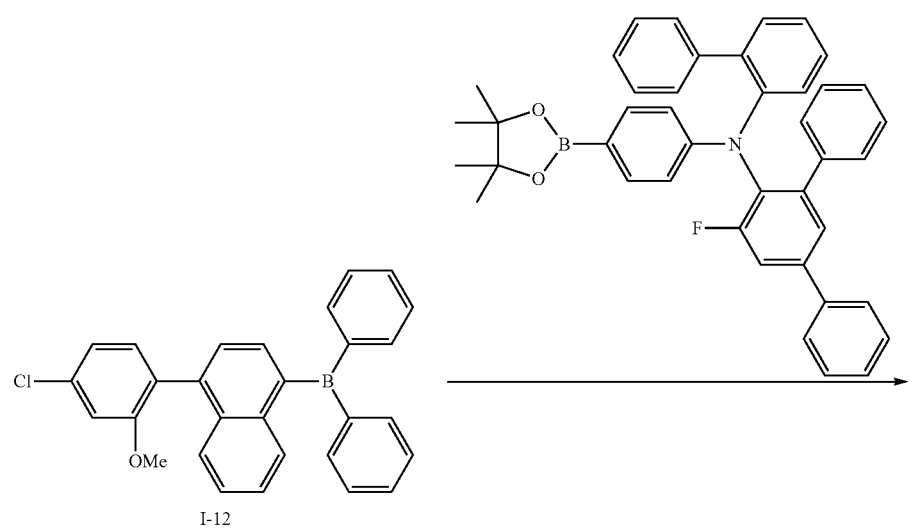
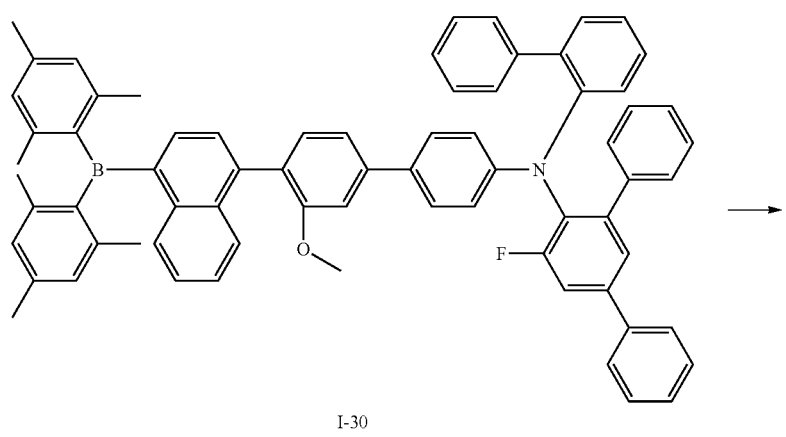

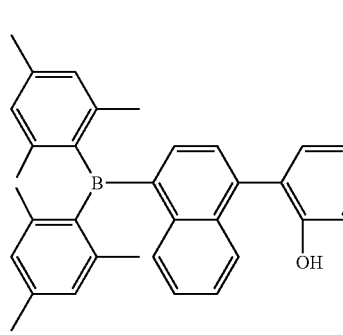

I-31

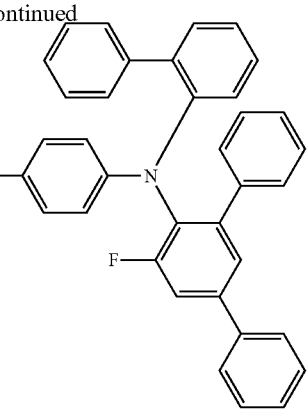

96

Synthesis of Intermediate I-30

6.70 g (yield: 69%) of Intermediate I-30 was prepared in the same manner as in the synthesis of Intermediate I-27, except that Intermediate I-12 was used instead of Intermediate I-2 and N-([1,1'-biphenyl]-2-yl)-5'-fluoro-N-(4-(4,4,5,5-tetramethyl-1,3,2-dioxaborolan-2-yl)phenyl)[1,1':3',1''-terphenyl]-4'-amine instead of 2-(5-(diphenylboranyl)naphthalen-1-yl)-4,4,5,5-tetramethyl-1,3,2-dioxaborolane. The compound thus obtained was confirmed by using MS/FAB.

$C_{71}H_{59}BFNO$ Cal. 972.07 Found. 972.11.

Synthesis of Intermediate I-31

3.59 g (yield: 75%) of Intermediate I-31 was prepared in the same manner as in the synthesis of Intermediate I-5, except that Intermediate I-30 was used instead of Intermediate I-4. The compound thus obtained was confirmed by using MS/FAB.

$C_{70}H_{57}BFNO$ Cal. 958.04 Found. 958.12.

Synthesis of Compound 96

3.54 g (yield: 84%) of Compound 96 was prepared in the same manner as in the synthesis of Compound 4, except that Intermediate I-29 was used instead of Intermediate I-5. The compound thus obtained was confirmed by using MS/FAB and 1H NMR.

$C_{62}H_{40}BNO_2$ Cal. 956.02, Found. 956.12.

Synthesis Example 12

Synthesis of Compound 99

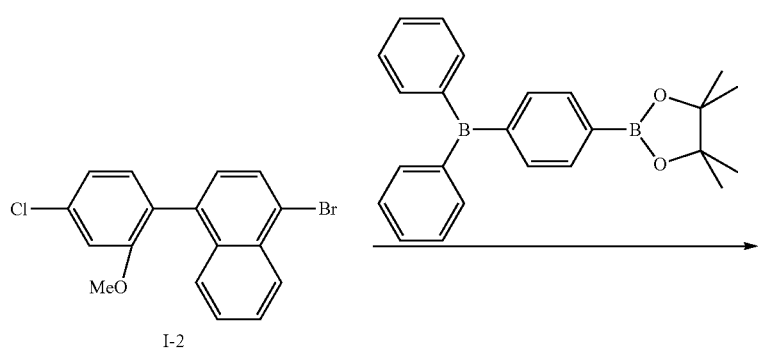

I-2

-continued
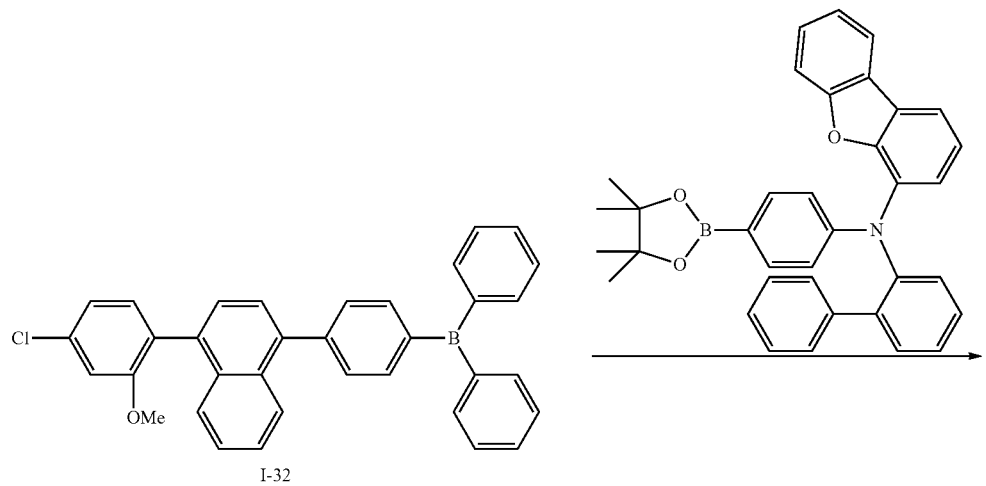
I-32
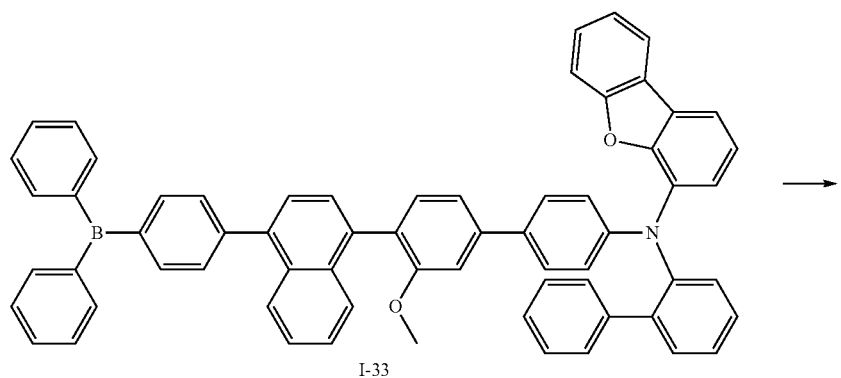
I-33
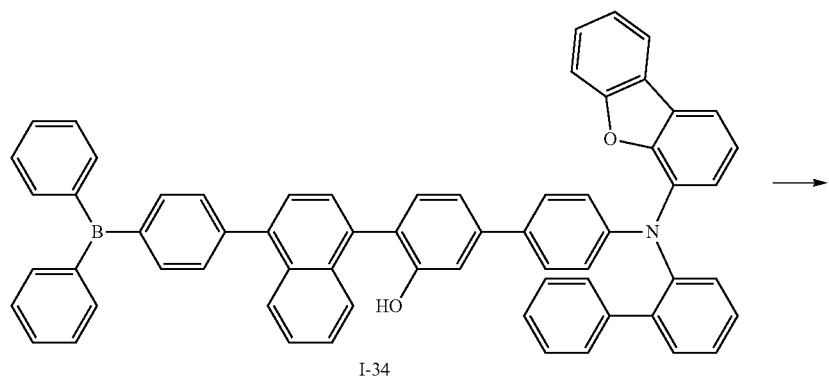
I-34
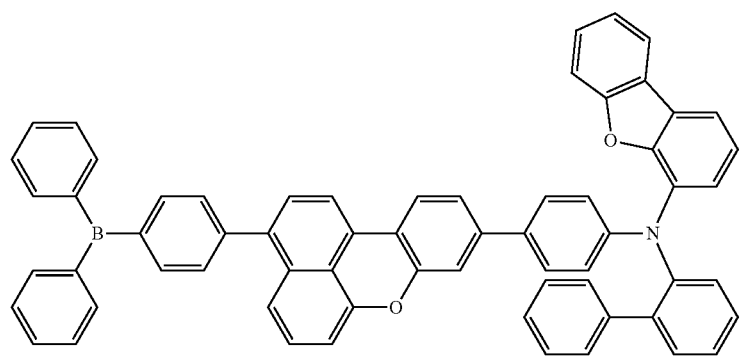
99

Synthesis of Intermediate I-32

3.81 g (yield: 75%) of Intermediate I-32 was prepared in the same manner as in the synthesis of Intermediate I-27, except that 2-(4-(diphenylboranyl)phenyl)-4,4,5,5-tetramethyl-1,3,2-dioxaborolane was used instead of 2-(5-(diphenylboranyl)naphthalen-1-yl)-4,4,5,5-tetramethyl-1,3,2-dioxaborolane. The compound thus obtained was confirmed by using MS/FAB.

$C_{35}H_{26}BClO$ Cal. 508.85 Found. 508.92.

Synthesis of Intermediate I-33

5.74 g (yield: 65%) of Intermediate I-33 was prepared in the same manner as in the synthesis of Intermediate I-27, except that Intermediate I-32 was used instead of Intermediate I-2, N-([1,1'-biphenyl]-2-yl)-N-(4-(4,4,5,5-tetramethyl-1,3,2-dioxaborolan-2-yl)phenyl)dibenzo[b,d]furan-4-amine instead of 2-(5-(diphenylboranyl)naphthalen-1-yl)-4,4,5,5-tetramethyl-1,3,2-dioxaborolane, and 1.16 g (1.0 mmol) of Pd(PPh₃)₄ was used. The compound thus obtained was confirmed by using MS/FAB.

$C_{65}H_{46}BNO_2$ Cal. 883.90 Found. 883.92.

Synthesis of Intermediate I-34

3.13 g (yield: 72%) of Intermediate I-34 was prepared in the same manner as in the synthesis of Intermediate I-5, except that Intermediate I-33 was used instead of Intermediate I-4. The compound thus obtained was confirmed by using MS/FAB.

$C_{64}H_{44}BNO_2$ Cal. 869.87 Found. 869.92.

Synthesis of Compound 99

3.47 g (yield: 80%) of Compound 96 was prepared in the same manner as in the synthesis of Compound 4, except that Intermediate I-34 was used instead of Intermediate I-5. The compound thus obtained was confirmed by using MS/FAB and 1H NMR.

$C_{64}H_{42}BNO_2$ Cal. 867.85, Found. 867.88.

TABLE 1

| Compound | 1H NMR (CDCl₃, 400 MHz) | MS/FAB Found | Calc. |
|---|---|---|---|
| 4 | δ = 8.51 (d, 1H), 7.96 (d, 1H), 7.89 (d, 1H), 7.80 (d, 1H), 7.38-7.19 (m, 6H), 6.82-6.74 (m, 11H), 6.68 (d, 1H), 2.1 (s, 12H), 0.24 (s, 18H) | 749.87 | 749.95 |
| 11 | δ = 8.33 (d, 1H), 8.02 (d, 1H), 7.89-7.87 (m, 2H), 7.80 (d, 1H), 7.76-7.51 (m, 9H), 7.47-7.23 (m, 8H), 7.11-7.09 (m, 2H), 6.95-6.89 (m, 3H), 6.7 (d, 1H), 6.56-6.54 (m, 2H), 2.38 (s, 6H), 1.61 (s, 6H) | 743.57 | 743.76, |
| 22 | δ = 8.40 (d, 1H), 8.08 (d, 1H), 7.88 (d, 1H), 7.70-7.63 (m, 5H), 7.51-7.50 (m, 5H), 7.40-7.39 (m, 2H), 7.33-7.30 (m, 2H), 7.11-7.06 (m, 5H), 6.96-6.92 (m, 4H), 6.62 (d, 1H), 6.52 (d, 1H), 6.39 (d, 1H), 6.24-6.22 (m, 2H), 2.17 (s, 12H) | 775.47 | 775.77 |
| 34 | δ = 8.40 (d, 1H), 8.08 (d, 1H), 7.88-7.76 (m, 3H), 7.57-7.55 (m, 2H), 7.48-7.30 (m, 7H), 7.16-7.11 (m, 3H), 6.99-6.97 (m, 2H), 6.81-6.77 (m, 5H), 6.66 (d, 1H), 6.44-6.38 (m, 3H), 2.2 (s, 12H), 2.18 (s, 6H), 1.61 (s, 6H) | 825.92 | 825.90, |
| 37 | δ = 8.40 (d, 1H), 8.08 (d, 1H), 7.88-7.76 (m, 3H), 7.69-7.65 (m, 2H), 7.57-7.30 (m, 9H), 7.14-7.12 (m, 2H), 6.99-6.92 (m, 4H), 6.81-6.78 (m, 4H), 6.50 (d, 1H), 6.37-6.35 (m, 1H), 2.2 (s, 12H), 2.18 (s, 6H) | 799.82 | 799.82 |
| 44 | δ = 8.46 (d, 1H), 8.40 (d, 1H), 8.08 (dd, 2H), 7.88-7.81 (m, 3H), 7.67-7.65 (m, 1H), 7.59-7.54 (m, 5H), 7.48-7.46 (m, 4H), 7.39-7.37 (m, 1H), 7.30-7.28 (m, 1H), 7.16-7.14 (m, 1H), 6.99-6.94 (m, 3H) 6.81-6.75 (m, 5H), 6.60 (d, 1H), 6.44 (d, 1H), 2.2 (s, 12H), 2.18 (s, 6H) | 809.92 | 809.86 |
| 55 | δ = 8.38 (d, 1H), 8.10 (dd, 2H), 7.96 (d, 1H), 7.80-7.75 (m, 6H), 7.57-7.55 (m, 2H), 7.48-7.45 (m, 3H), 7.44-7.30 (m, 12H), 7.20-7.15 (m, 2H), 6.98 (d, 1H), 6.80 (d, 1H), 6.63-6.60 (m, 3H) 6.44 (d, 1H), 0.24 (s, 9H) | 797.92 | 797.88 |
| 73 | δ = 8.30 (d, 1H), 7.96-7.84 (m, 4H), 7.59-7.44 (m, 4H), 7.32-7.30 (m, 5H), 7.24-7.19 (m, 2H), 7.06 (d, 1H), 6.97-6.93 (m, 5H), 6.85-6.83 (m, 2H), 6.63-6.59 (dd, 2H), 6.42 (d, 1H), 1.94 (s, 3H) | 649.75 | 649.55 |
| 84 | δ = 8.40 (d, 1H), 8.08 (d, 1H), 7.88 (d, 1H), 7.69-7.67 (m, 3H), 7.65-7.63 (m, 4H), 7.51-7.49 (m, 3H), 7.40-7.38 (m, 2H), 7.30-7.28 (m, 2H), 7.19 (d, 1H), 6.83 (dd, 2H), 6.81-6.78 (m, 4H), 6.56 (d, 1H), 6.46 (d, 1H), 2.28 (s, 3H), 2.26 (s, 6H), 2.20 (s, 12H), 2.18 (s, 6H) | 845.91 | 845.91 |
| 90 | δ = 8.41 (d, 1H), 8.03 (d, 1H), 7.96-7.94 (m, 2H), 7.82 (d, 1H), 7.76-7.72 (m, 4H), 7.73-7.65 (m, 3H), 7.60-7.54 (m, 8H), 7.49-7.40 (m, 4H), 7.38-7.36 (m, 3H), 7.27-7.25 (m, 5H), 7.14-7.12 (m, 2H), 6.99 (d, 1H), 6.94-6.92 (m, 3H), 6.50 (d, 1H), 6.37 (d, 1H) | 841.81 | 841.82 |
| 96 | δ = 8.28 (d, 1H), 8.08 (d, 1H), 8.01 (d, 1H), 7.88 (d, 1H), 7.68-7.59 (m, 6H), 7.58-7.50 (m, 8H), 7.46-7.38 (m, 6H), 7.30 (d, 1H), 7.19-7.13 (m, 3H), 7.05-7.00 (m, 2H), 6.86 (m, 1H), 6.81-6.78 (m, 4H), 6.26-6.24 (m, 2H), 2.2 (s, 12H), 2.18 (s, 6H) | 956.12 | 956.02 |

TABLE 1-continued

| Compound | 1H NMR (CDCl$_3$, 400 MHz) | MS/FAB Found | Calc. |
|---|---|---|---|
| 99 | δ = 8.35 (d, 1H), 7.95 (d, 1H), 7.83-7.81 (m, 3H), 7.76-7.72 (m, 4H), 7.70-7.65 (m, 3H), 7.57-7.54 (m, 8H), 7.51-7.46 (m, 3H), 7.40-7.38 (m, 6H), 7.26-7.22 (m, 4H), 7.13-6.90 (m, 7H), 6.40-6.38 (m, 2H) | 867.88 | 867.85 |

Example 1

A indium tin oxide (ITO) glass substrate (available from Corning) having an ITO layer deposited thereon at a thickness of 15 Ω/cm2 (1,200 Å) was cut to a size of 50 mm×50 mm×0.7 mm, sonicated in isopropyl alcohol and pure water for 5 minutes each, and then cleaned with UV and ozone for 30 minutes. The ITO glass substrate was then mounted on a vacuum depositor.

4,4'-Bis[N-phenyl-N-(9-phenylcarbazol-3-yl)amino]-1,1'-biphenyl (HT13) was deposited on the ITO glass substrate to form a hole injection layer having a thickness of 600 Å, N-[1,1'-biphenyl]-4-yl-9,9-dimethyl-N-[4-(9-phenyl-9H-carbazol-3-yl)phenyl]-9H-fluorene-2-amine (HT3) was deposited on the hole injection layer to form a hole transport layer having a thickness of 300 Å, and thus a hole transport region was prepared.

9,10-di-naphthalene-2-yl-anthracene (ADN), as a host, and Compound 4, as a dopant, were co-deposited at a weight ratio of 98:2 on the hole transport region to form an emission layer having a thickness of 300 Å.

Alga was deposited on the emission layer to form an electron transport layer having a thickness of 300 Å, LiF was deposited on the electron transport layer to form an electron injection layer having a thickness of 10 Å, and thus an electron transport region was prepared.

Al was deposited on the electrode injection layer to form a cathode having a thickness of 3000 Å, thereby completing manufacture of an organic light-emitting device.

Al was vacuum deposited on the electron transport region to form a cathode having a thickness of 3,000 Å, thereby completing manufacture of an organic light-emitting device.

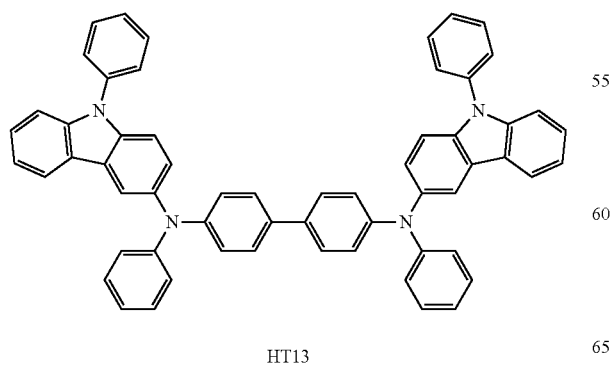

HT13

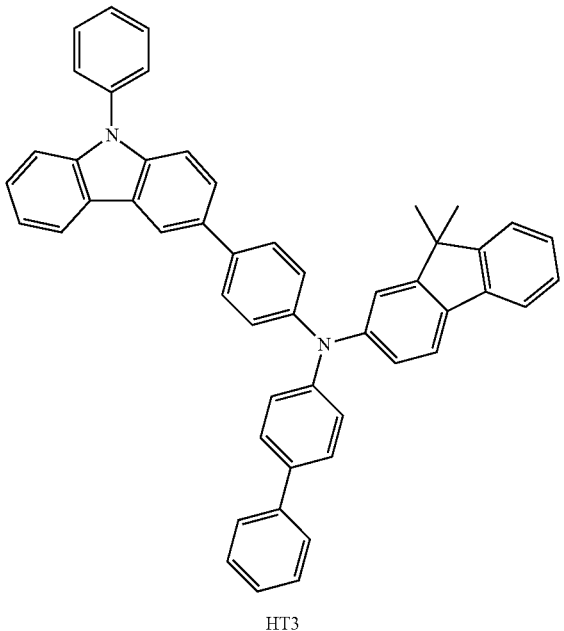

HT3

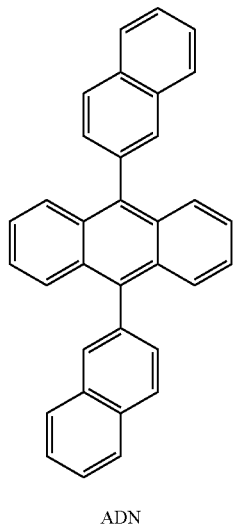

ADN

Example 2

An organic light-emitting device was manufactured in the same manner as in Example 1, except that Compound 11 was used instead of Compound 4 as a dopant in the formation of the emission layer.

Example 3

An organic light-emitting device was manufactured in the same manner as in Example 1, except that Compound 22 was used instead of Compound 4 as a dopant in the formation of the emission layer.

Example 4

An organic light-emitting device was manufactured in the same manner as in Example 1, except that Compound 34 was used instead of Compound 4 as a dopant in the formation of the emission layer.

Example 5

An organic light-emitting device was manufactured in the same manner as in Example 1, except that Compound 37 was used instead of Compound 4 as a dopant in the formation of the emission layer.

Example 6

An organic light-emitting device was manufactured in the same manner as in Example 1, except that Compound 44 was used instead of Compound 4 as a dopant in the formation of the emission layer.

Example 7

An organic light-emitting device was manufactured in the same manner as in Example 1, except that Compound 55 was used instead of Compound 4 as a dopant in the formation of the emission layer.

Example 8

An organic light-emitting device was manufactured in the same manner as in Example 1, except that Compound 73 was used instead of Compound 4 as a dopant in the formation of the emission layer.

Example 9

An organic light-emitting device was manufactured in the same manner as in Example 1, except that Compound 84 was used instead of Compound 4 as a dopant in the formation of the emission layer.

Example 10

An organic light-emitting device was manufactured in the same manner as in Example 1, except that Compound 90 was used instead of Compound 4 as a dopant in the formation of the emission layer.

Example 11

An organic light-emitting device was manufactured in the same manner as in Example 1, except that Compound 96 was used instead of Compound 4 as a dopant in the formation of the emission layer.

Example 12

An organic light-emitting device was manufactured in the same manner as in Example 1, except that Compound 99 was used instead of Compound 4 as a dopant in the formation of the emission layer.

Comparative Example 1

An organic light-emitting device was manufactured in the same manner as in Example 1, except that Compound A was used instead of Compound 4 as a dopant in the formation of the emission layer:

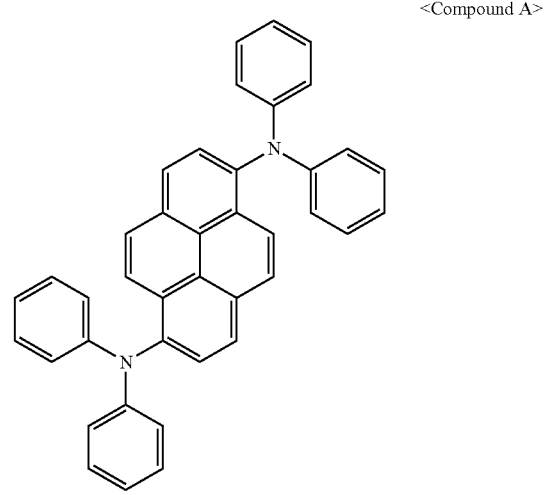 [SMILES: c1ccc(N(c2ccccc2)c2ccc3ccc4c(N(c5ccccc5)c5ccccc5)ccc5ccc2c3c54)cc1]

<Compound A>

Comparative Example 2

An organic light-emitting device was manufactured in the same manner as in Example 1, except that Compound B was used instead of Compound 4 as a dopant in the formation of the emission layer:

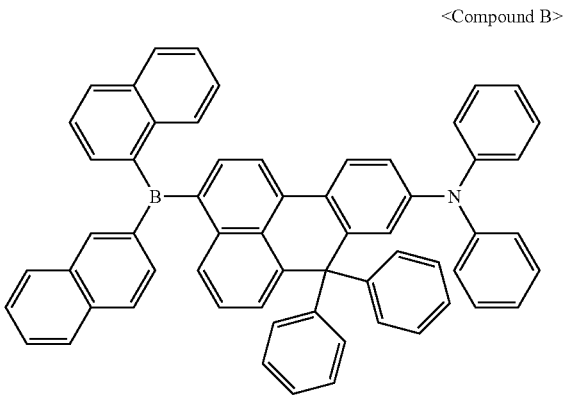 [SMILES: c1ccc(N(c2ccccc2)c2ccc3c(c2)C(c2ccccc2)(c2ccccc2)c2cccc4c(B(c5ccc6ccccc6c5)c5cccc6ccccc56)ccc-3c24)cc1]

<Compound B>

Evaluation Example 1

Driving voltages, current densities, luminances, efficiencies, and half-lives of the organic light-emitting devices prepared in Examples 1 to 12 and Comparative Examples 1 and 2 were evaluated by using Kethley SMU 236 and a luminance meter PR650, and the results are shown in Table 2. The half-life is defined as the time for the luminance of an organic light-emitting device to decline to 50% of its initial luminance.

TABLE 2

| | Emission layer | Driving voltage (V) | Current density (mA/cm$^2$) | Luminance (cd/m$^2$) | Efficiency (cd/A) | Color of emitted light | Half-life (hr@100 mA/cm$^2$) |
|---|---|---|---|---|---|---|---|
| Example 1 | Compound 4 | 6.72 | 50 | 2,990 | 5.98 | blue | 345 |
| Example 2 | Compound 11 | 6.75 | 50 | 3,075 | 6.15 | blue | 294 |
| Example 3 | Compound 22 | 6.70 | 50 | 3,035 | 6.07 | blue | 312 |
| Example 4 | Compound 34 | 6.69 | 50 | 3,140 | 6.28 | blue | 323 |
| Example 5 | Compound 37 | 6.72 | 50 | 3,190 | 6.38 | blue | 346 |
| Example 6 | Compound 44 | 6.70 | 50 | 3,090 | 6.18 | blue | 290 |
| Example 7 | Compound 55 | 6.73 | 50 | 3,150 | 6.30 | blue | 331 |
| Example 8 | Compound 73 | 6.76 | 50 | 3,170 | 6.34 | blue | 309 |
| Example 9 | Compound 84 | 6.70 | 50 | 3,205 | 6.41 | blue | 352 |
| Example 10 | Compound 90 | 6.68 | 50 | 3,160 | 6.32 | blue | 348 |
| Example 11 | Compound 96 | 6.69 | 50 | 3,145 | 6.29 | blue | 335 |
| Example 12 | Compound 99 | 6.65 | 50 | 3,075 | 6.15 | blue | 355 |
| Comparative Example 1 | Compound A | 6.96 | 50 | 2,730 | 5.46 | blue | 248 |
| Comparative Example 2 | Compound B | 6.99 | 50 | 2,950 | 5.30 | blue | 295 |

As shown in Table 2, driving voltages, luminances, efficiencies, and half-lives of the organic light-emitting devices prepared in Examples 1 to 12 were excellent compared to those of the organic light-emitting devices prepared in Comparative Examples 1 and 2.

As described above, according to the one or more of the above embodiments, an organic light-emitting device including the condensed-cyclic compound may have a low driving voltage, high efficiency, high luminance, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:
1. A condensed-cyclic compound represented by Formula 1:

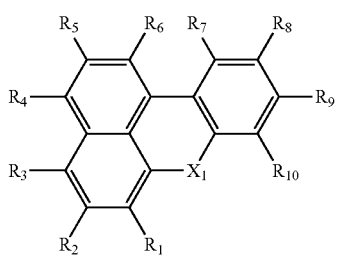

<Formula 1> wherein, in Formula 1,
$X_1$ is one of O, S, N-$(L_3)_{a3}$-$(Ar_5)$, and Si$(R_{11})(R_{12})$;
$R_1$ to $R_{12}$ are each independently one of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si$(Q_1)(Q_2)(Q_3)$, and at least one of $R_1$ to $R_{10}$ is a group represented by Formula 2, and at least one of $R_1$ to $R_{10}$ is a group represented by Formula 3:

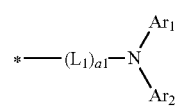

<Formula 2>

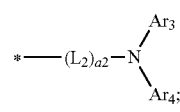

<Formula 3> wherein, in Formulae 1 to 3,
$L_1$ to $L_3$ are each independently one of a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3 are each independently 0, 1, 2, or 3; when a1 is 2 or greater, two or more $L_1$s are identical to or different from each other, when a2 is 2 or greater, two or more $L_2$s are identical to or different from each other, and, when a3 is 2 or greater, two or more $L_2$s are identical to or different from each other;

$Ar_1$ to $Ar_5$ are each independently one of a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is one of:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently one of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed-cyclic compound as claimed in claim 1, wherein $L_1$ to $L_3$ are each independently one of:

a phenylene group, a pentalenylene group, an indenylene group, a naphthylene group, an azulenylene group, a heptalenylene group, an indacenylene group, an acenaphthylene group, a fluorenylene group, a spinofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed-cyclic compound as claimed in claim 1, wherein $L_1$ to $L_3$ are each independently one of groups represented by Formulae 3-1 to 3-35:

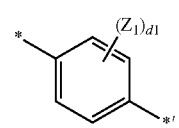

Formula 3-1

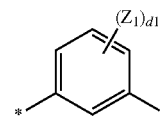

Formula 3-2

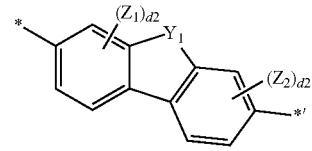

Formula 3-3

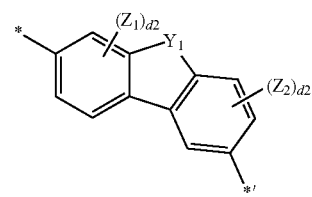

Formula 3-4

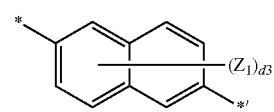

Formula 3-5

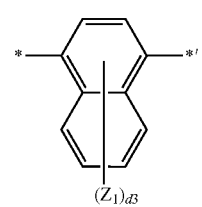

Formula 3-6

-continued
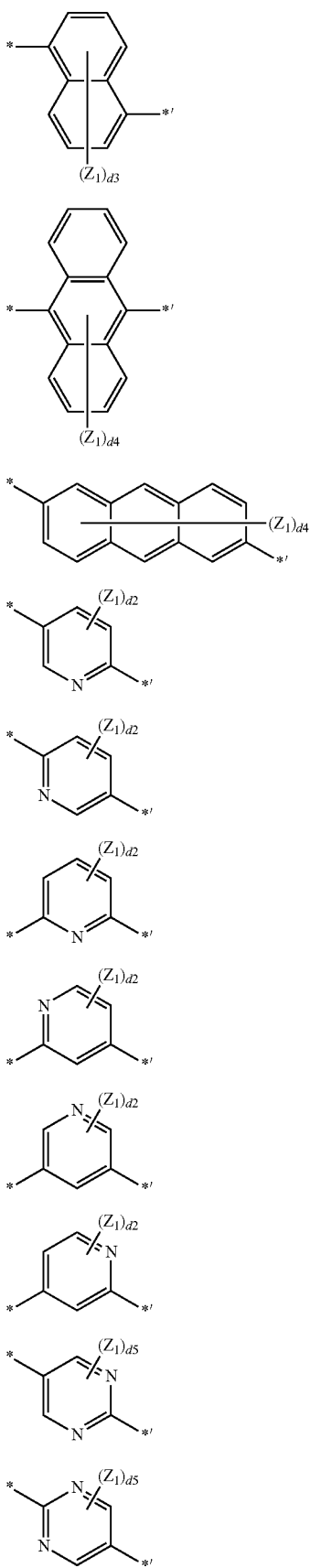
Formula 3-7
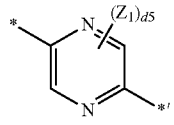
Formula 3-8
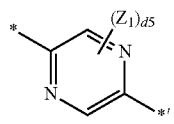
Formula 3-9
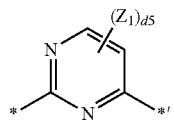
Formula 3-10
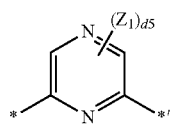
Formula 3-11
Formula 3-12
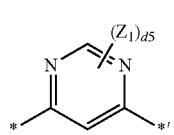
Formula 3-13
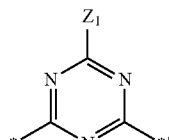
Formula 3-14
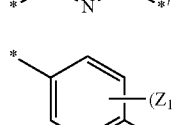
Formula 3-15
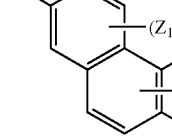
Formula 3-16
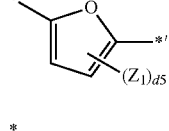
Formula 3-17
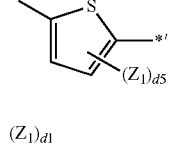
Formula 3-18
Formula 3-19
Formula 3-20
Formula 3-21
Formula 3-22
Formula 3-23
Formula 3-24
Formula 3-25
Formula 3-26
Formula 3-27
Formula 3-28
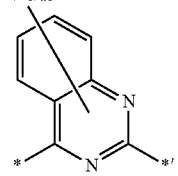

-continued

Formula 3-29
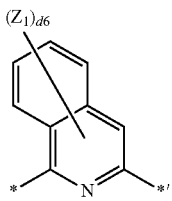

Formula 3-30
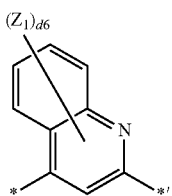

Formula 3-31
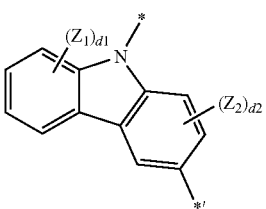

Formula 3-32
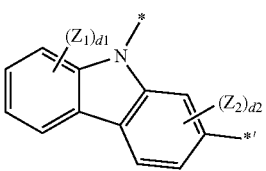

Formula 3-33
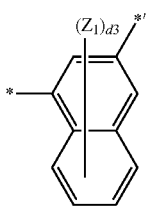

Formula 3-34
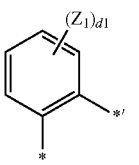

Formula 3-35
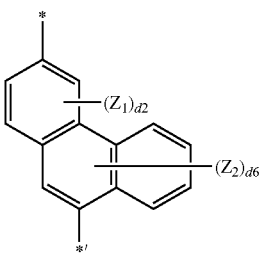

wherein, in Formulae 3-1 to 3-35,
$Y_1$ is O, S, $C(Z_3)(Z_4)$, $N(Z_5)$, or $Si(Z_6)(Z_7)$;
$Z_1$ to $Z_7$ are each independently one of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is an integer from 1 to 4, d2 is an integer from 1 to 3, d3 is an integer from 1 to 6, d4 is an integer from 1 to 8, d5 is an integer of 1 or 2, d6 is an integer from 1 to 5, and * and *' are a binding site to a neighboring atom.

4. The condensed-cyclic compound as claimed in claim 1, wherein $L_1$ to $L_3$ are each independently one of groups represented by Formulae 4-1 to 4-29:

Formula 4-1
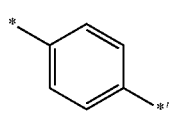

Formula 4-2
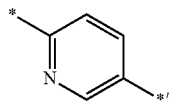

Formula 4-3
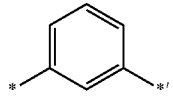

Formula 4-4
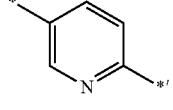

Formula 4-5
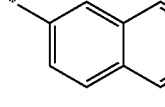

Formula 4-6
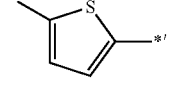

Formula 4-7

Formula 4-8
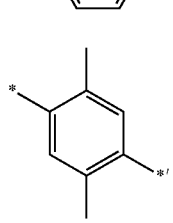

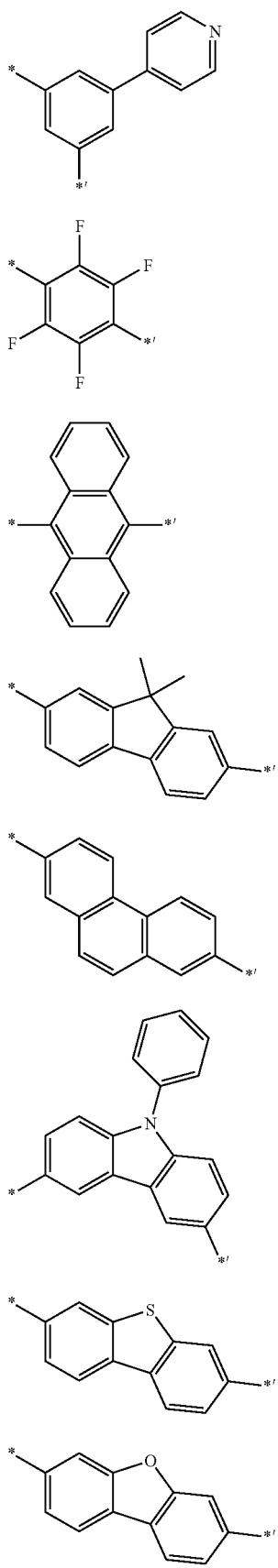
-continued
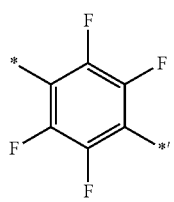
Formula 4-17
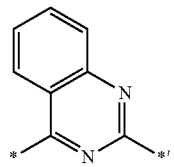
Formula 4-18
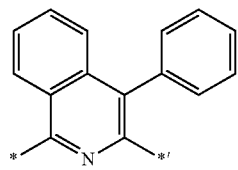
Formula 4-19
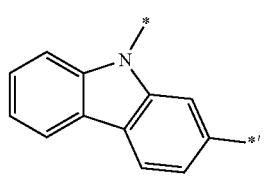
Formula 4-20
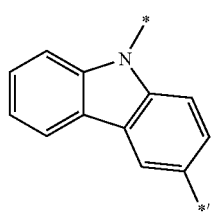
Formula 4-21
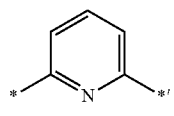
Formula 4-22
Formula 4-23
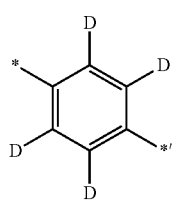
Formula 4-24
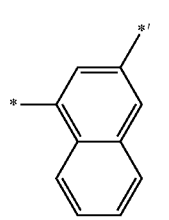
Formula 4-25

-continued

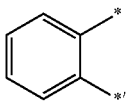

Formula 4-26

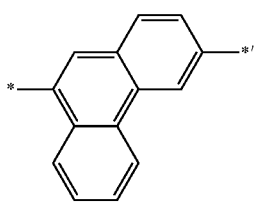

Formula 4-27

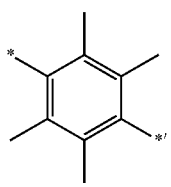

Formula 4-28

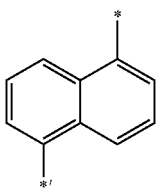

Formula 4-29 wherein, in Formulae 4-1 to 4-29, * and *' are a binding site to a neighboring atom.

5. The condensed-cyclic compound as claimed in claim 1, wherein a1 to a3 are each independently 0 or 1.

6. The condensed-cyclic compound as claimed in claim 1, wherein $Ar_1$ to $Ar_5$ are each independently one of:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and $-Si(Q_{31})(Q_{32})(Q_{33})$, wherein $Q_{31}$ to $Q_{33}$ are each independently one of a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

7. The condensed-cyclic compound as claimed in claim 1, wherein $Ar_1$ to $Ar_5$ are each independently one of:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a Spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and $-Si(Q_{31})(Q_{32})(Q_{33})$, wherein $Q_{31}$ to $Q_{33}$ are each independently one of a $C_1$-$C_{10}$ alkyl group, a $C_1$-$C_{10}$ alkoxy group, a phenyl group, and a naphthyl group.

8. The condensed-cyclic compound as claimed in claim 1, wherein $Ar_1$ to $Ar_5$ are each independently one of:

a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and $-Si(Q_{31})(Q_{32})(Q_{33})$, wherein $Q_{31}$ to $Q_{33}$ are each independently a $C_1$-$C_{10}$ alkyl group, a $C_1$-$C_{10}$ alkoxy group, a phenyl group, and a naphthyl group.

9. The condensed-cyclic compound as claimed in claim 1, wherein $R_1$ to $R_{10}$ are each independently one of:

a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently one of a $C_1$-$C_{10}$ alkyl group, a $C_1$-$C_{10}$ alkoxy group, a phenyl group, and a naphthyl group.

10. The condensed-cyclic compound as claimed in claim 1, wherein $R_1$ to $R_{10}$ are each independently one of:

a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently one of a $C_1$-$C_{10}$ alkyl group, a $C_1$-$C_{10}$ alkoxy group, a phenyl group, and a naphthyl group.

11. The condensed-cyclic compound as claimed in claim 1, wherein $R_{11}$ and $R_{12}$ are each independently one of:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, $C_1$-$C_{10}$ alkyl group, $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$).

12. The condensed-cyclic compound as claimed in claim 1, wherein: $Ar_1$ to $Ar_4$ are each independently one of groups represented by Formulae 5-1 to 5-43, and $R_1$ to $R_{10}$ are each independently one represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-43, wherein $Q_1$ to $Q_3$ are each independently one of a $C_1$-$C_{10}$ alkyl group, a $C_1$-$C_{10}$ alkoxy group, a phenyl group, and a naphthyl group:

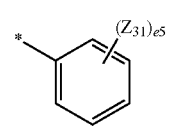

Formula 5-1

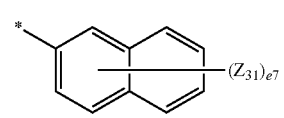

Formula 5-2

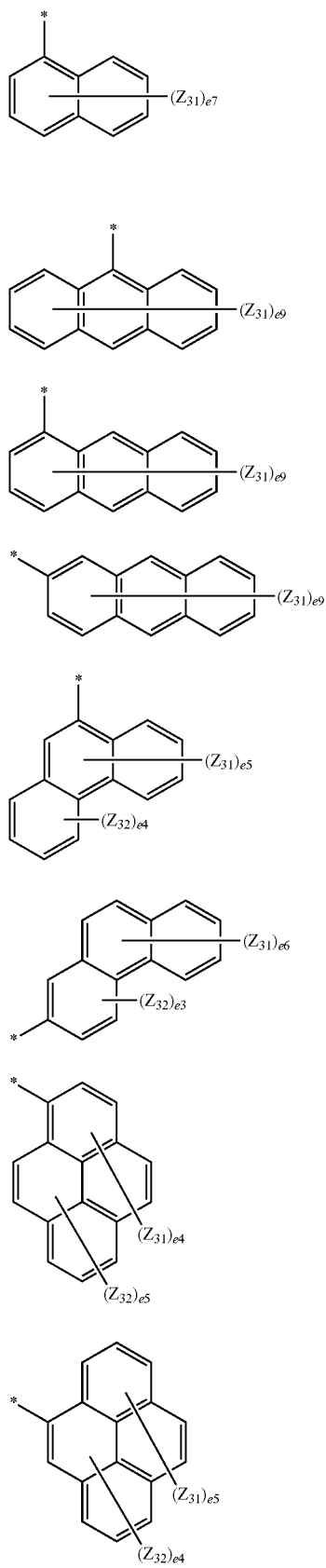
Formula 5-3
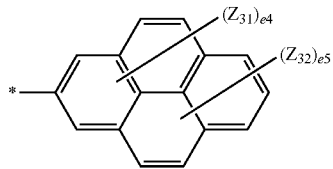
Formula 5-11
Formula 5-4
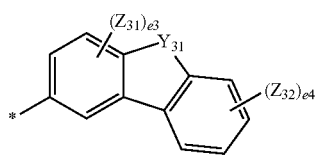
Formula 5-12
Formula 5-5
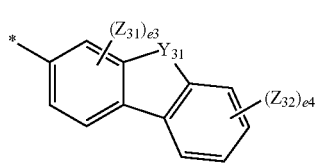
Formula 5-13
Formula 5-6
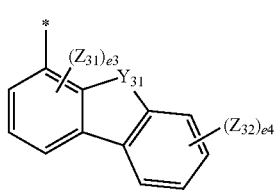
Formula 5-14
Formula 5-7
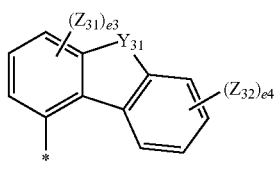
Formula 5-15
Formula 5-8
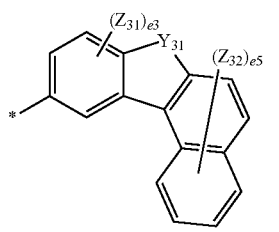
Formula 5-16
Formula 5-9
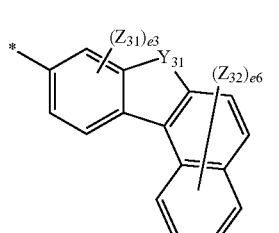
Formula 5-17
Formula 5-10
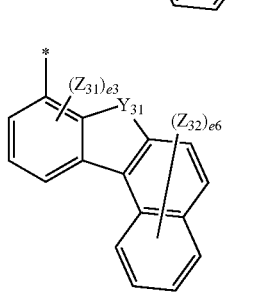
Formula 5-18

-continued
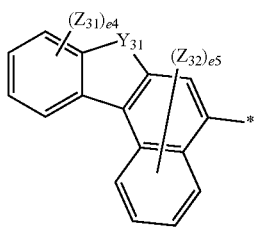
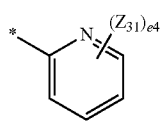
Formula 5-19
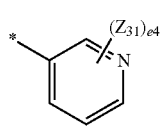
Formula 5-20
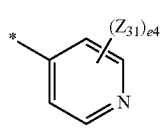
Formula 5-21
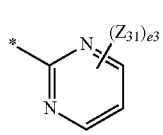
Formula 5-22
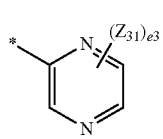
Formula 5-23
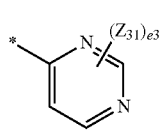
Formula 5-24
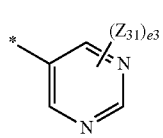
Formula 5-25
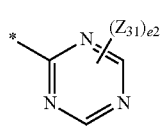
Formula 5-26
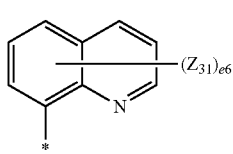
Formula 5-27
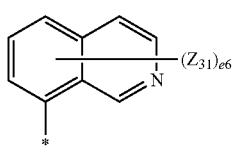
Formula 5-28
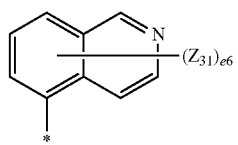
Formula 5-29
-continued
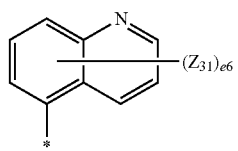
Formula 5-30
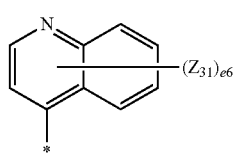
Formula 5-31
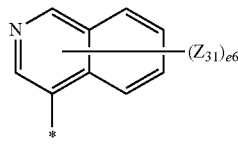
Formula 5-32
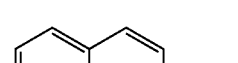
Formula 5-33
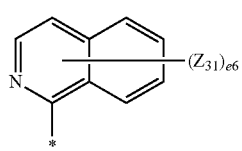
Formula 5-34
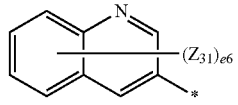
Formula 5-35
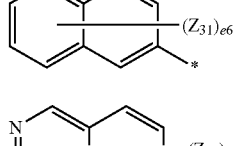
Formula 5-36
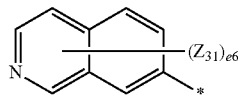
Formula 5-37
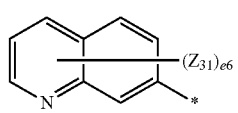
Formula 5-38
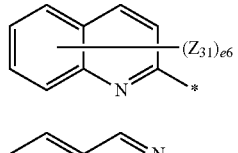
Formula 5-39
Formula 5-40
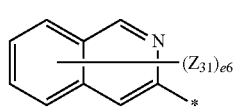
Formula 5-41

Formula 5-42

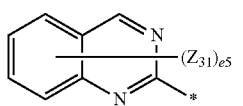

Formula 5-43

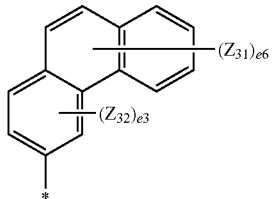

wherein, in Formulae 5-1 to 5-43, $Y_{31}$ is O, S, $C(Z_{33})(Z_{34})$, $N(Z_{35})$, or $Si(Z_{36})(Z_{37})$;

$Z_{31}$ to $Z_{37}$ are each independently one of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e2 is an integer of 1 or 2, e3 is an integer of from 1 to 3, e4 is an integer of from 1 to 4, e5 is an integer of from 1 to 5, e6 is an integer of from 1 to 6, e7 is an integer of from 1 to 7, e8 is an integer of from 1 to 8, e9 is an integer of from 1 to 9, and * is a binding site to a neighboring atom.

13. The condensed-cyclic compound as claimed in claim 1, wherein $Ar_1$ to $Ar_4$ are each independently one of groups represented by Formulae 6-1 to 6-40, and $R_1$ to $R_{10}$ are each independently one of a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —$Si(Q_1)(Q_2)(Q_3)$, a phenyl group, a naphthyl group, a pyridinyl group, a pyrimidinyl group, and a triazinyl group, wherein $Q_1$ to $Q_3$ are each independently one of a $C_1$-$C_{10}$ alkyl group, a $C_1$-$C_{10}$ alkoxy group, a phenyl group, and a naphthyl group:

Formula 6-1

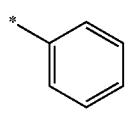

Formula 6-2

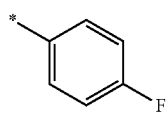

Formula 6-3

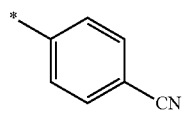

Formula 6-4

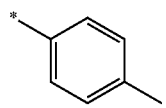

Formula 6-5

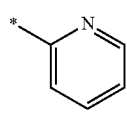

Formula 6-6

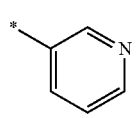

Formula 6-7

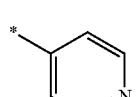

Formula 6-8

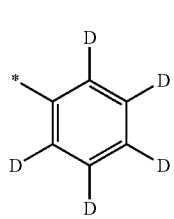

Formula 6-9

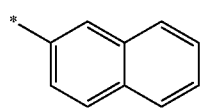

Formula 6-10

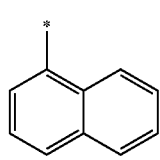

Formula 6-11

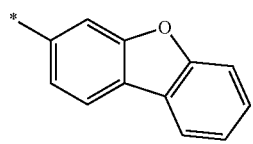

Formula 6-12

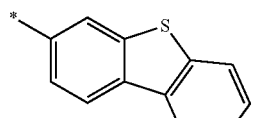

Formula 6-13

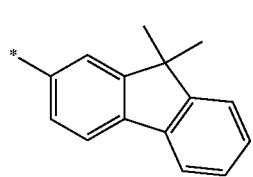

-continued
Formula 6-14
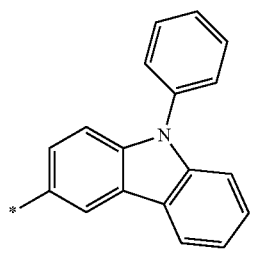
Formula 6-15
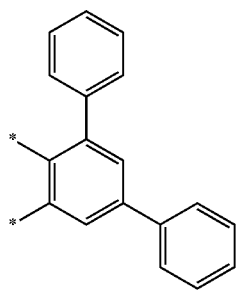
Formula 6-16
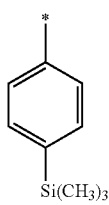
Formula 6-17
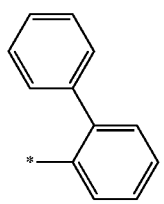
Formula 6-18
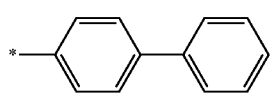
Formula 6-19
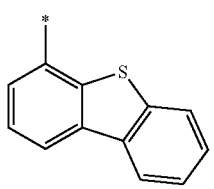
Formula 6-20
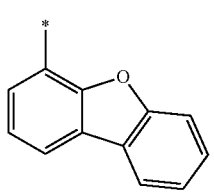
-continued
Formula 6-21
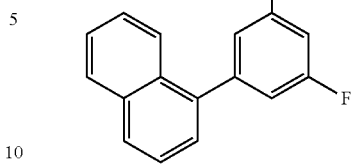
Formula 6-22
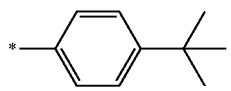
Formula 6-23
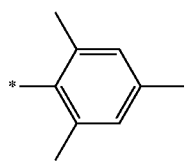
Formula 6-24
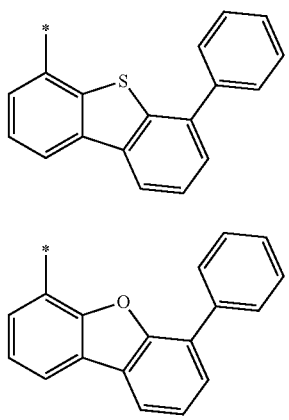
Formula 6-25
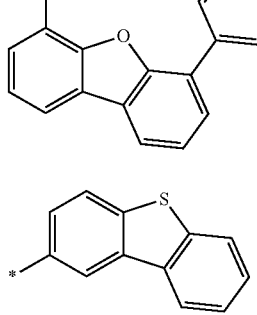
Formula 6-26
Formula 6-27
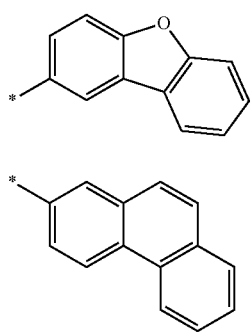
Formula 6-28
Formula 6-29
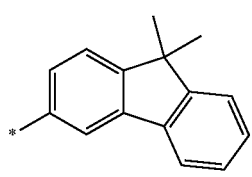

-continued
Formula 6-30
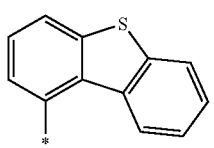
Formula 6-31
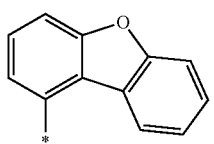
Formula 6-32
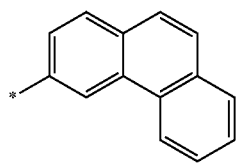
Formula 6-33
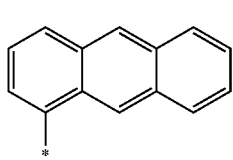
Formula 6-34
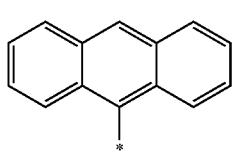
Formula 6-35
Formula 6-36
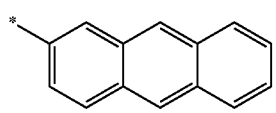
Formula 6-37
Formula 6-38
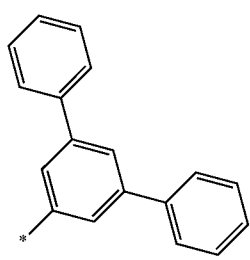
Formula 6-39
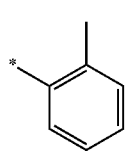
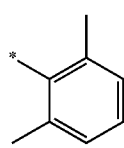
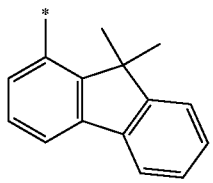
-continued
Formula 6-40
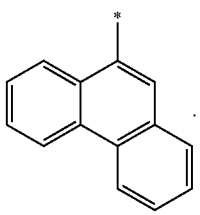
14. The condensed-cyclic compound as claimed in claim 1, wherein the condensed-cyclic compound is represented by one of Formulae 1-1 to 1-6:
<Formula 1-1>
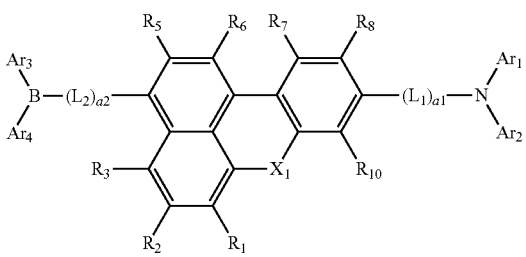
<Formula 1-2>
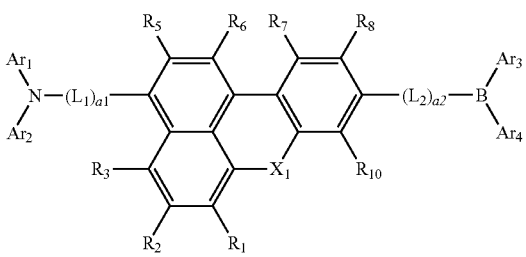
<Formula 1-3>
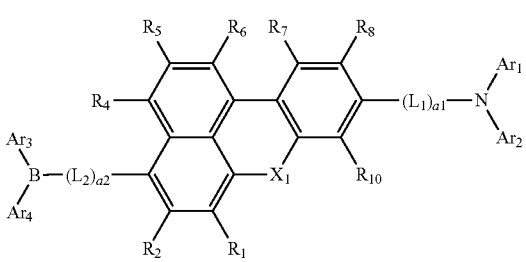
<Formula 1-4>
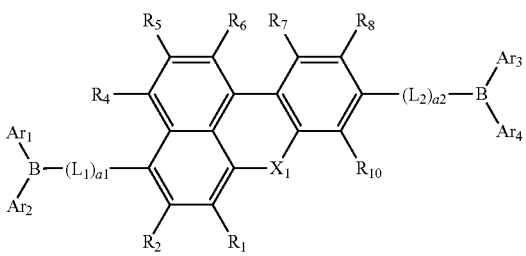

-continued

<Formula 1-5>

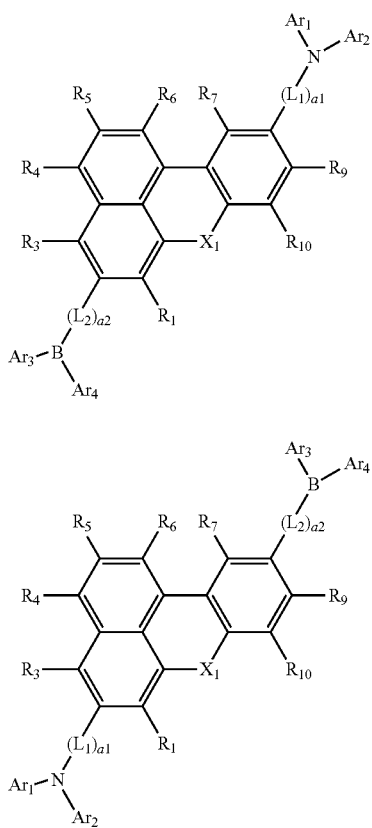

<Formula 1-6> wherein, in Formulae 1-1 to 1-6, $X_1$, $L_1$ to $L_3$, a1 to a3, $Ar_1$ to $Ar_5$, and $R_1$ to $R_{14}$ are the same as defined in claim 1.

15. The condensed-cyclic compound as claimed in claim 1, wherein the condensed-cyclic compound is represented by one of Formulae 1-1(A) to 1-1(D):

<Formula 1-1(A)>

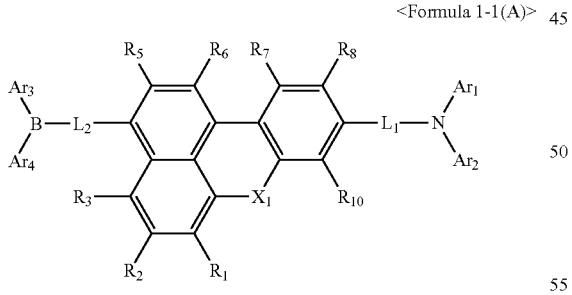

<Formula 1-1(B)>

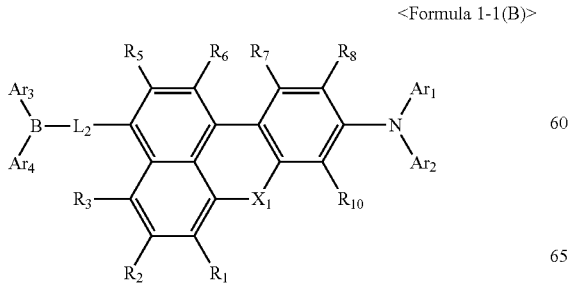

-continued

<Formula 1-1(C)>

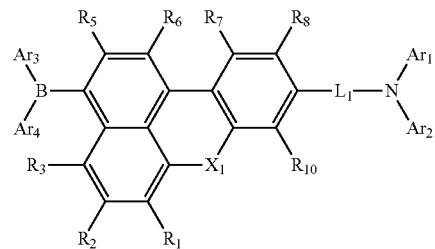

<Formula 1-1(D)>

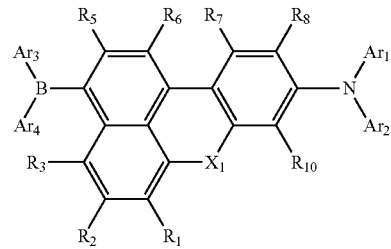

wherein, in Formulae 1-1(A) to 1-1(D), $X_1$ is O or S, $L_1$ and $L_2$ are each independently one of a phenylene group, a naphthylene group, a pyridinylene group, a pyrimidinylene group, and a triazinylene group; and a phenylene group, a naphthylene group, a pyridinylene group, a pyrimidinylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group;

$Ar_1$ to $Ar_4$ are each independently one of groups represented by Formulae 5-1 to Formula 5-43;

Formula 5-1

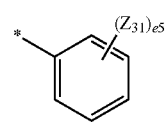

Formula 5-2

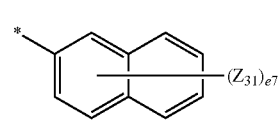

Formula 5-3

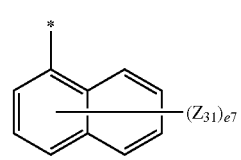

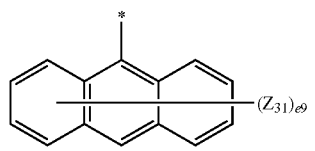
Formula 5-4
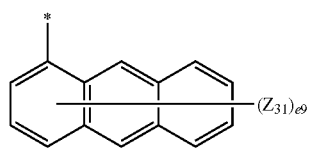
Formula 5-5
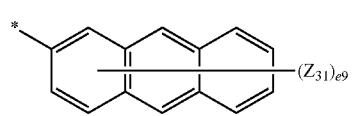
Formula 5-6
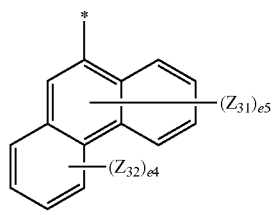
Formula 5-7
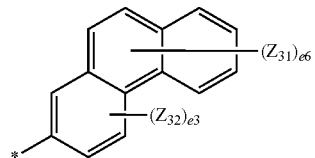
Formula 5-8
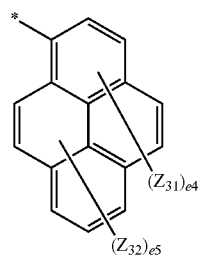
Formula 5-9
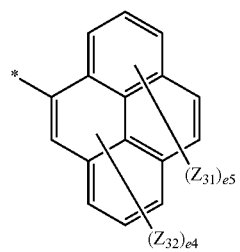
Formula 5-10
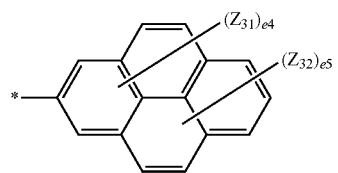
Formula 5-11
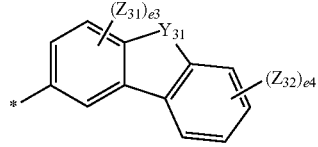
Formula 5-12
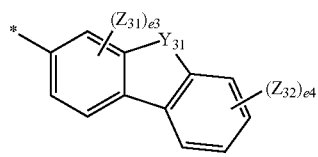
Formula 5-13
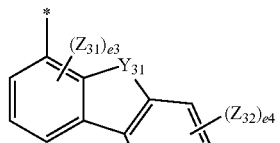
Formula 5-14
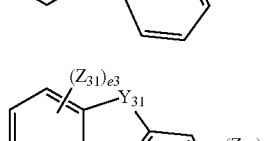
Formula 5-15
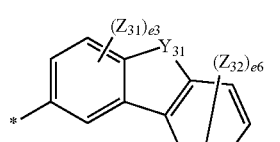
Formula 5-16
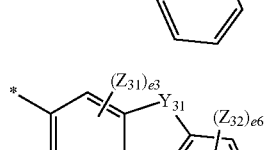
Formula 5-17
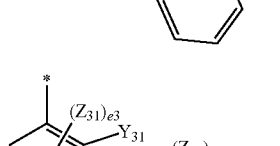
Formula 5-18
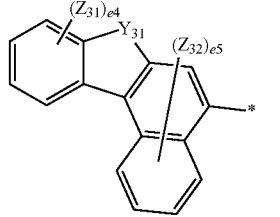
Formula 5-19

| | |
|---|---|
| Formula 5-20 | Formula 5-30 |
| Formula 5-21 | Formula 5-31 |
| Formula 5-22 | Formula 5-32 |
| Formula 5-23 | Formula 5-33 |
| Formula 5-24 | Formula 5-34 |
| Formula 5-25 | Formula 5-35 |
| Formula 5-26 | Formula 5-36 |
| Formula 5-27 | Formula 5-37 |
| Formula 5-28 | Formula 5-38 |
| Formula 5-29 | Formula 5-39 |

-continued

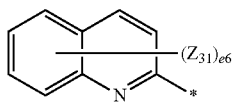
Formula 5-40

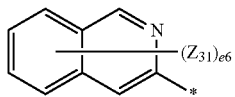
Formula 5-41

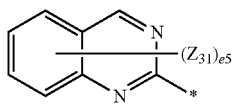
Formula 5-42

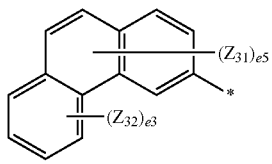
Formula 5-43 wherein, in Formulae 5-1 to 5-43, $Y_{31}$ is O, S, $C(Z_{33})(Z_{34})$, $N(Z_{35})$, or $Si(Z_{36})(Z_{37})$;

$Z_{31}$ to $Z_{37}$ are each independently one of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e2 is an integer of 1 or 2, e3 is an integer of from 1 to 3, e4 is an integer of from 1 to 4, e5 is an integer of from 1 to 5, e6 is an integer of from 1 to 6, e7 is an integer of from 1 to 7, e8 is an integer of from 1 to 8, e9 is an integer of from 1 to 9, and * is a binding site to a neighboring atom, $R_1$ to $R_3$, $R_5$ to $R_8$, and $R_{10}$ are each independently one of a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group.

16. The condensed-cyclic compound as claimed in claim 1, wherein the condensed-cyclic compound is one of Compounds 1 to 100:

1

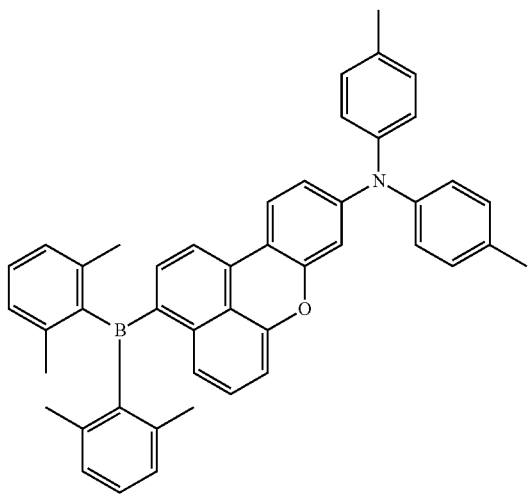

2

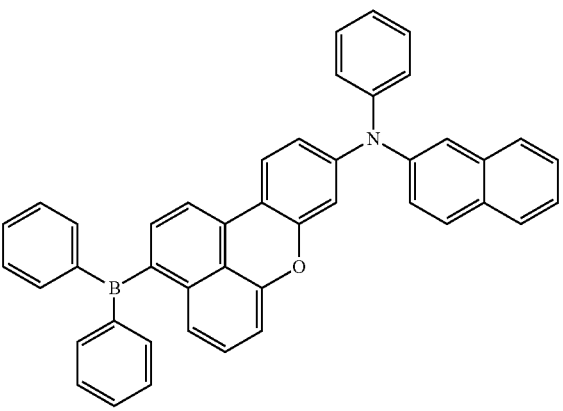

3

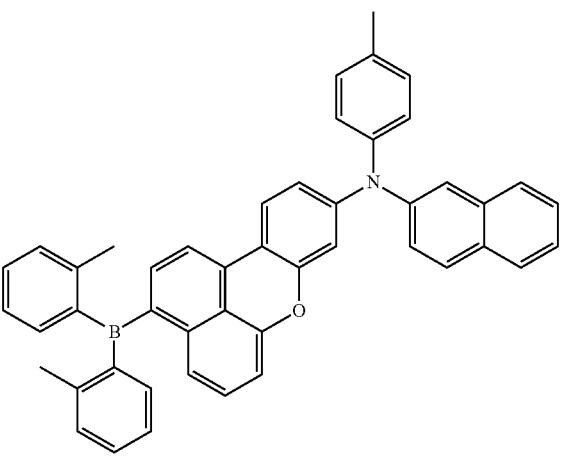

-continued
4
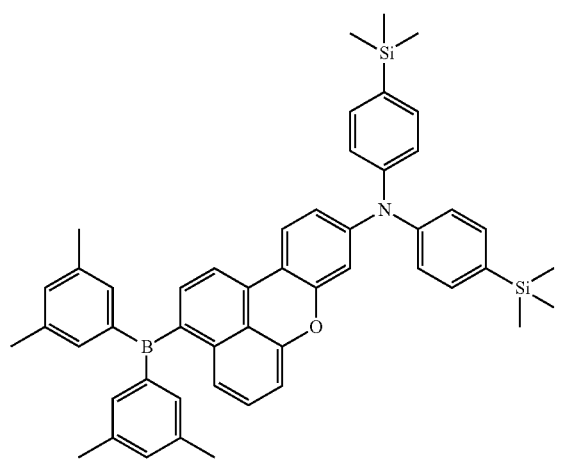
5
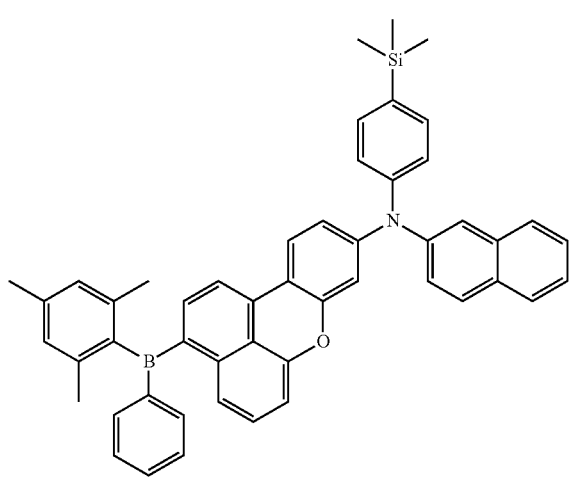
6
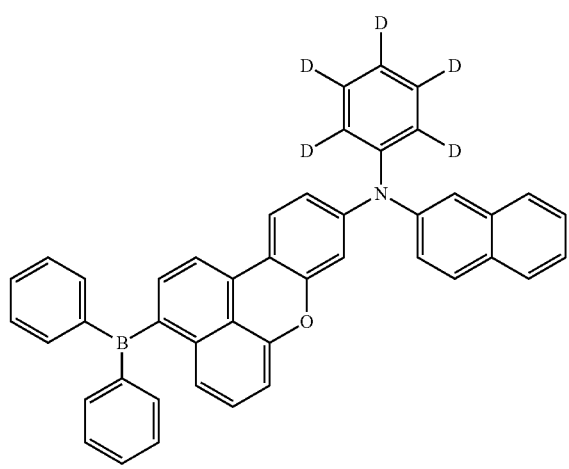
-continued
7
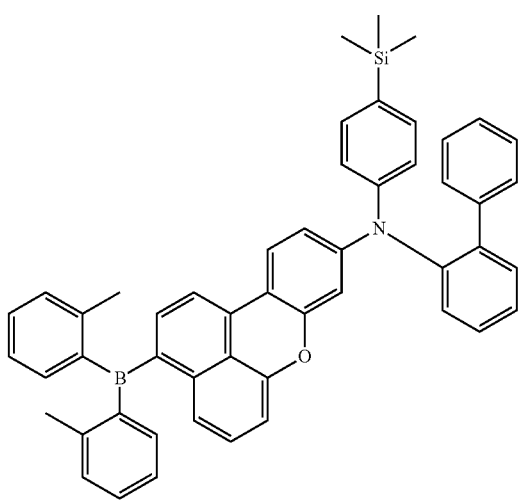
8
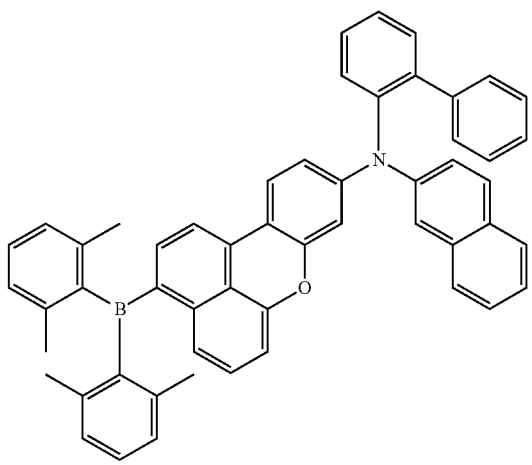
9
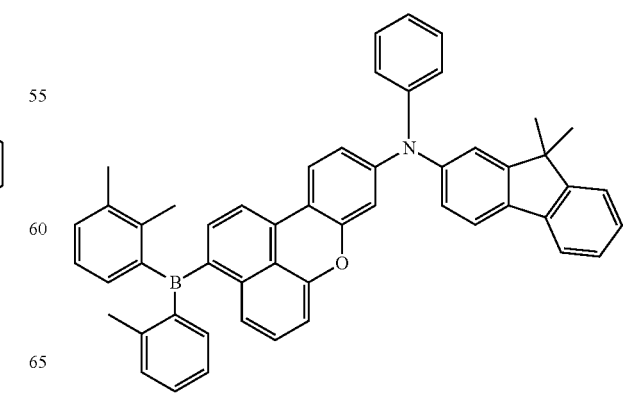

183
-continued
10
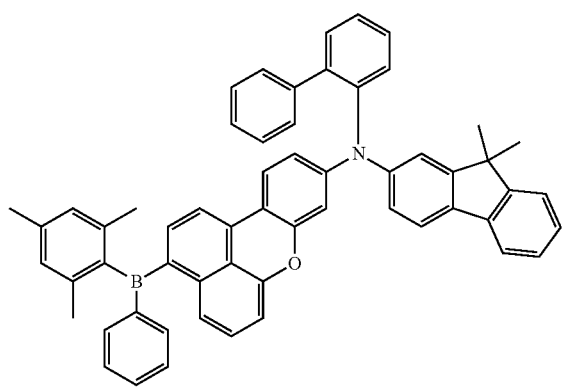
11
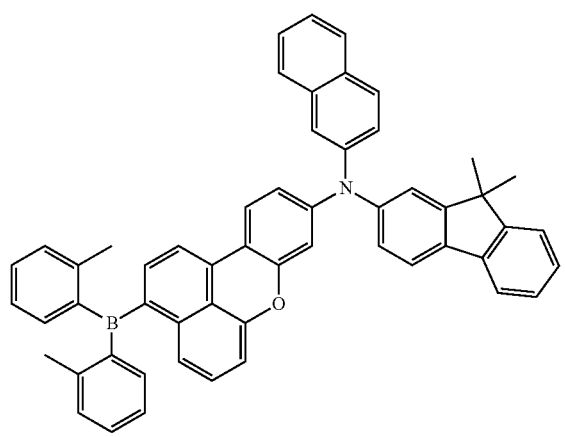
12
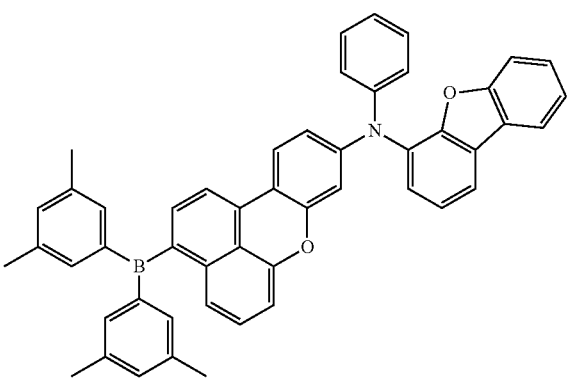
184
-continued
13
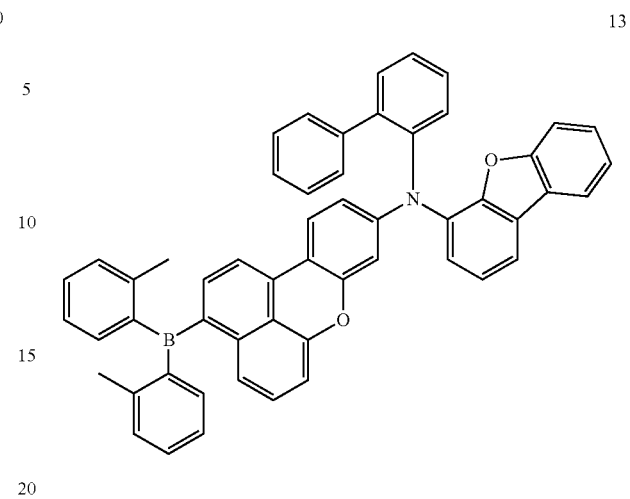
14
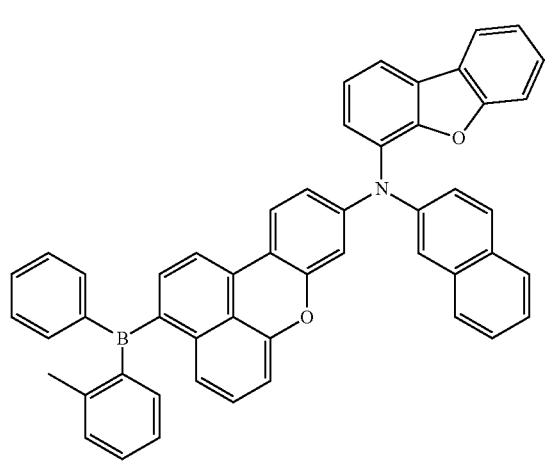
15
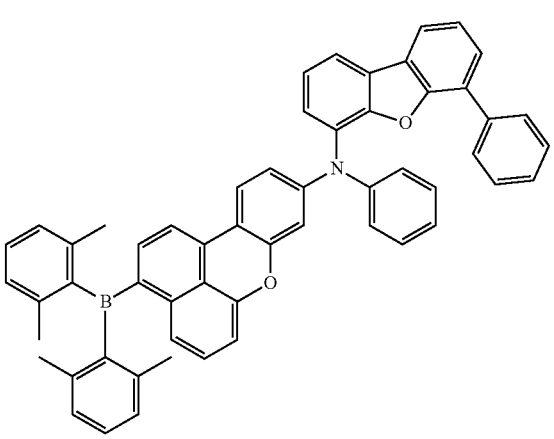

-continued
16
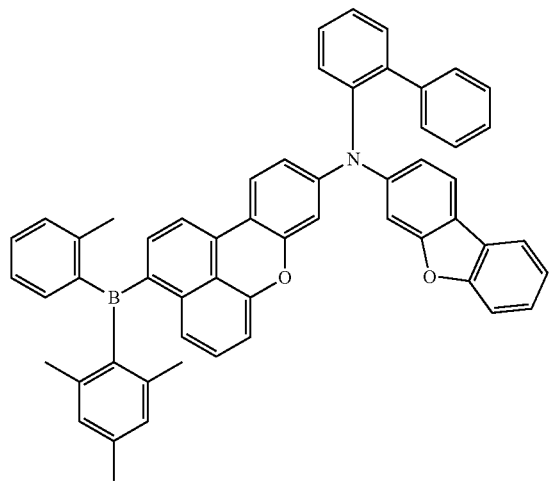
17
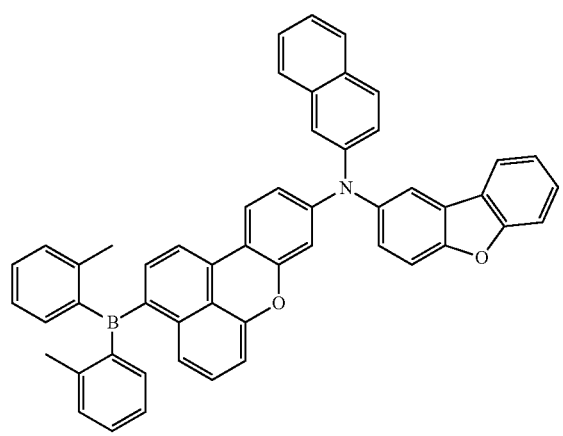
18
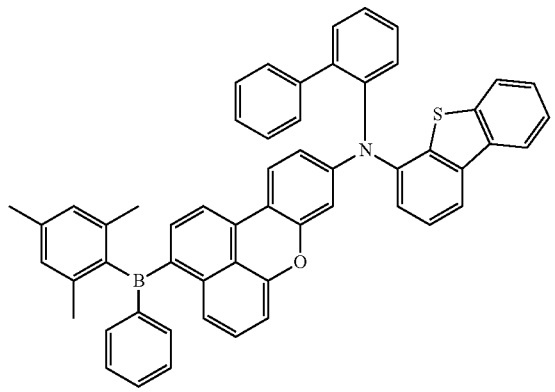
-continued
19
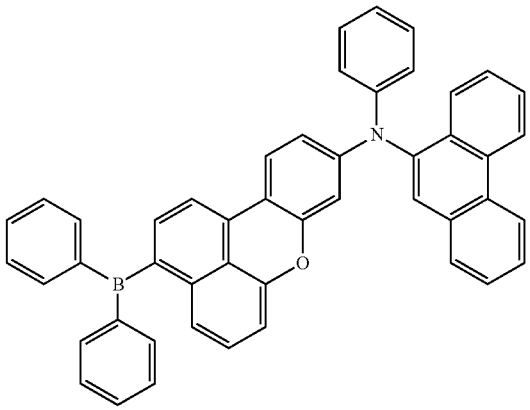
20
21
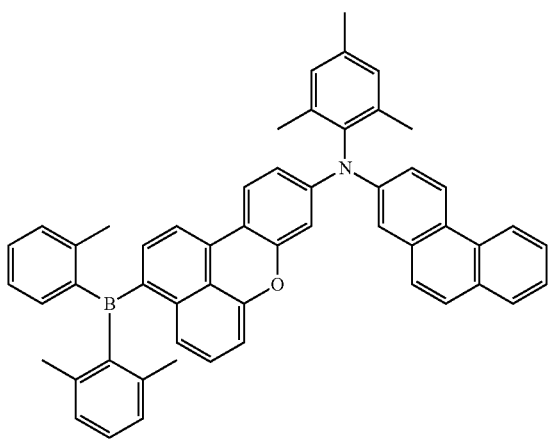

-continued
22
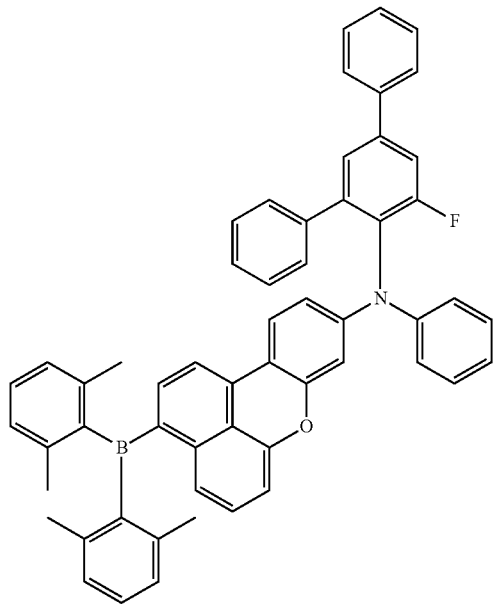
23
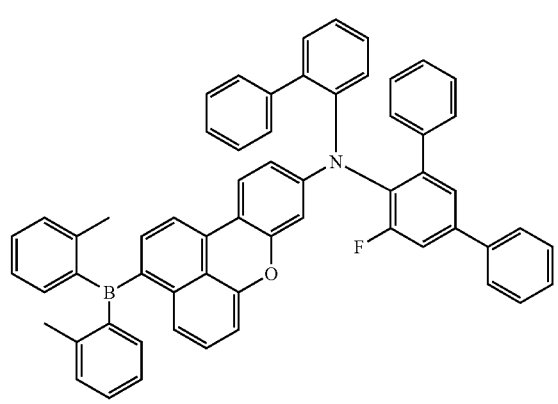
24
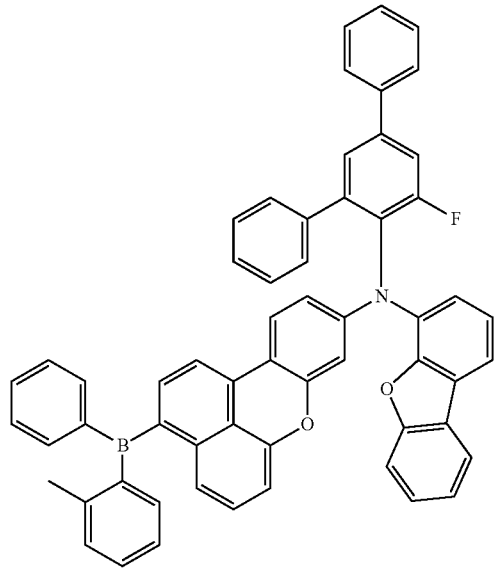
-continued
25
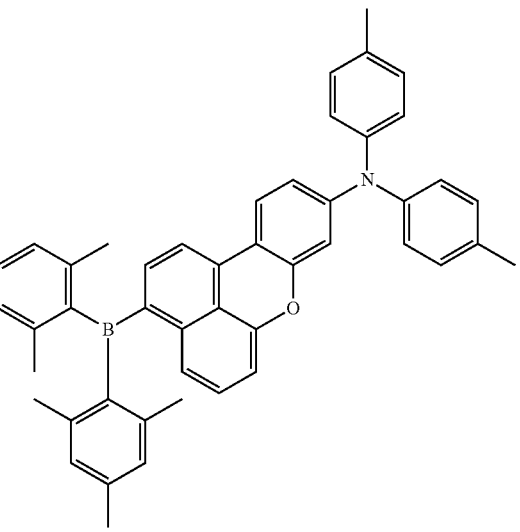
26
27

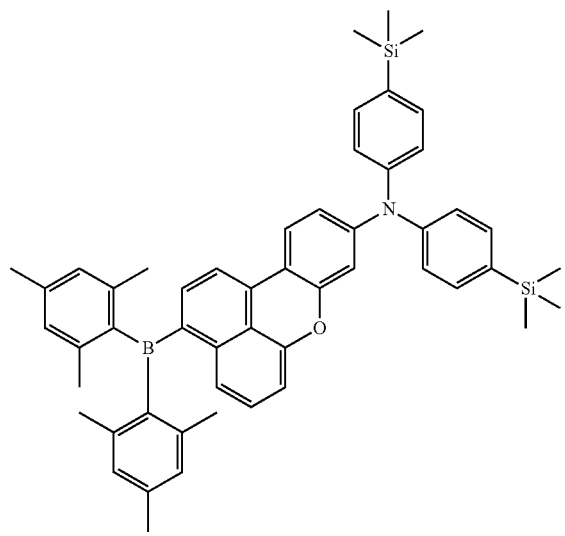
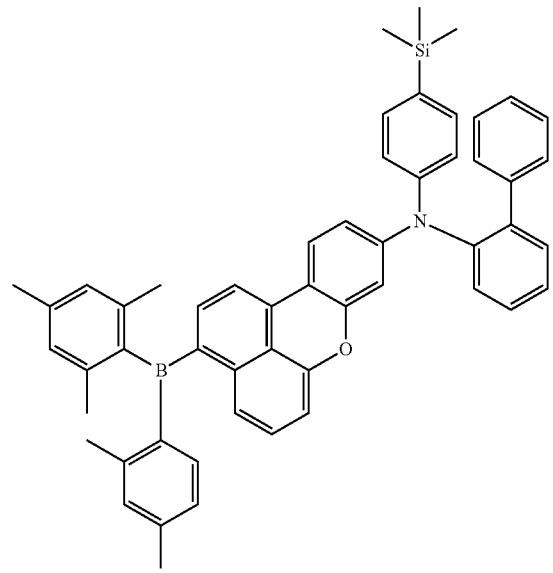
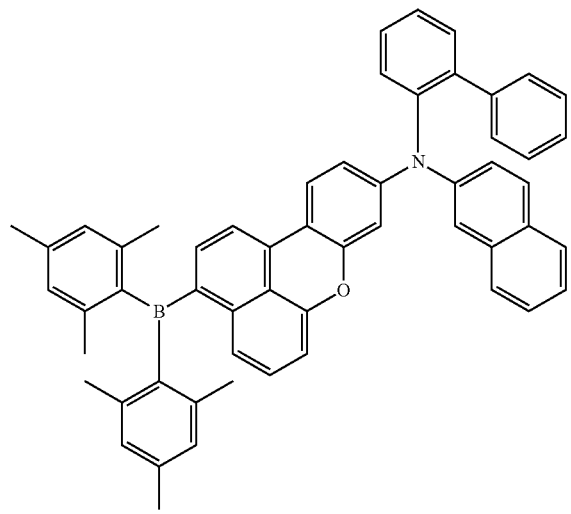
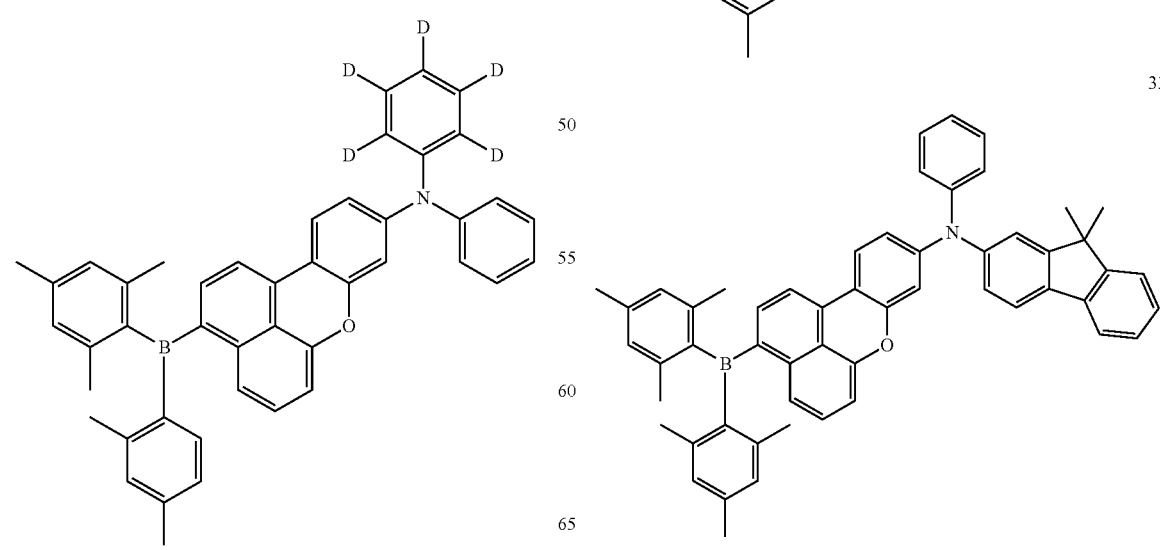

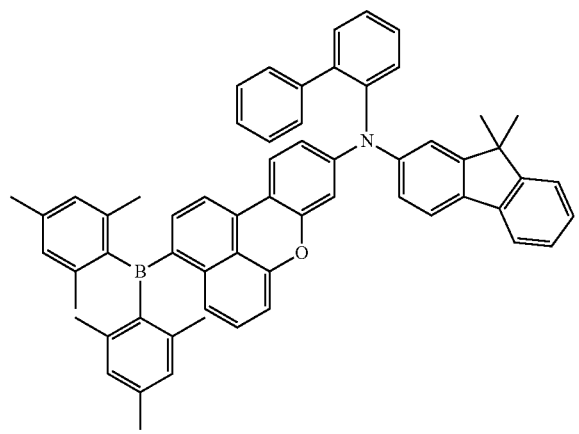
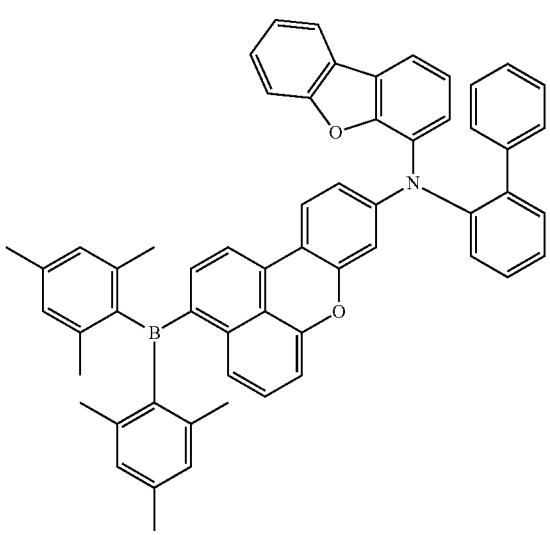
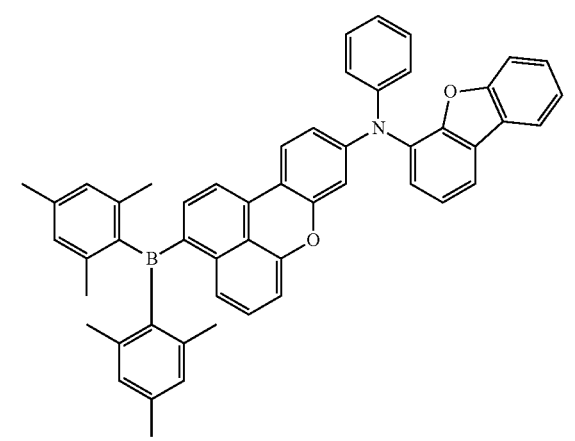
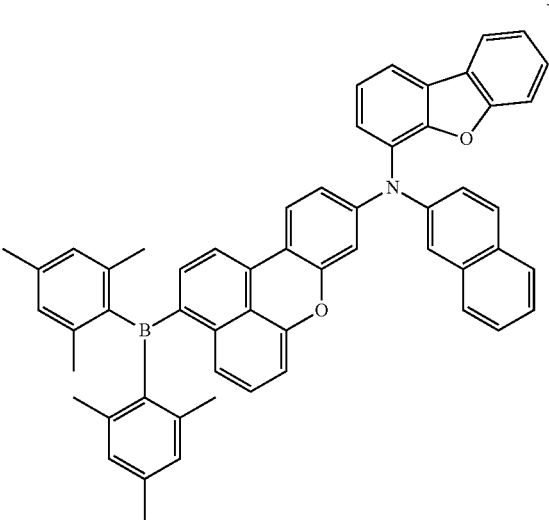

40
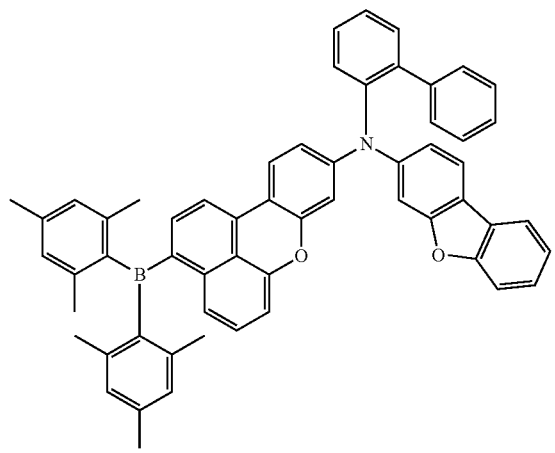
41
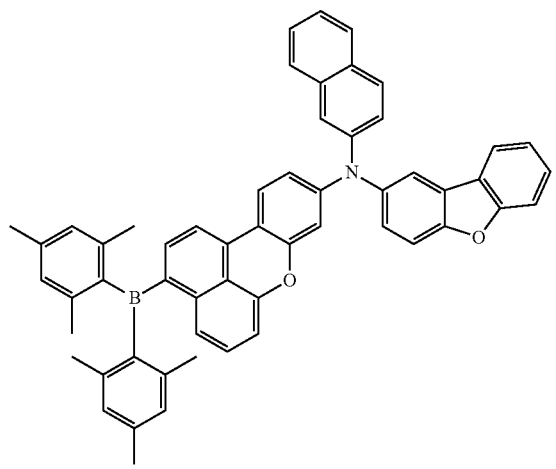
42
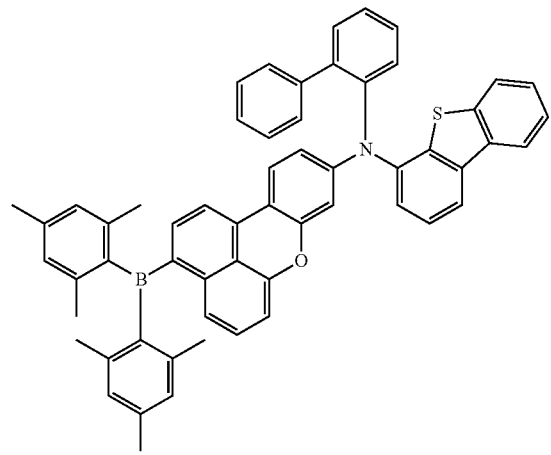
43
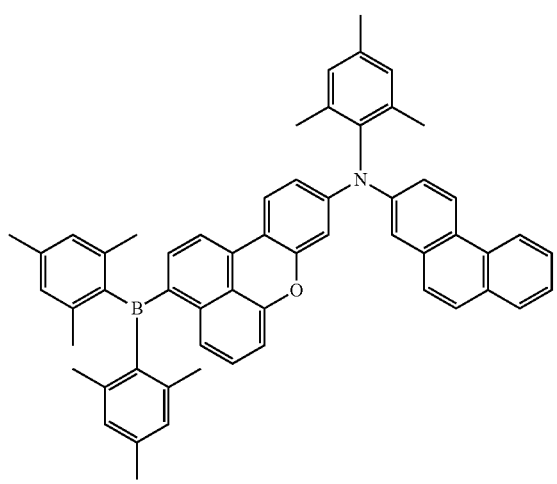
44
45

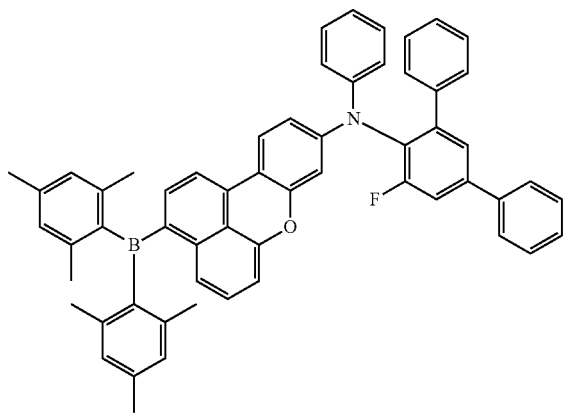
46
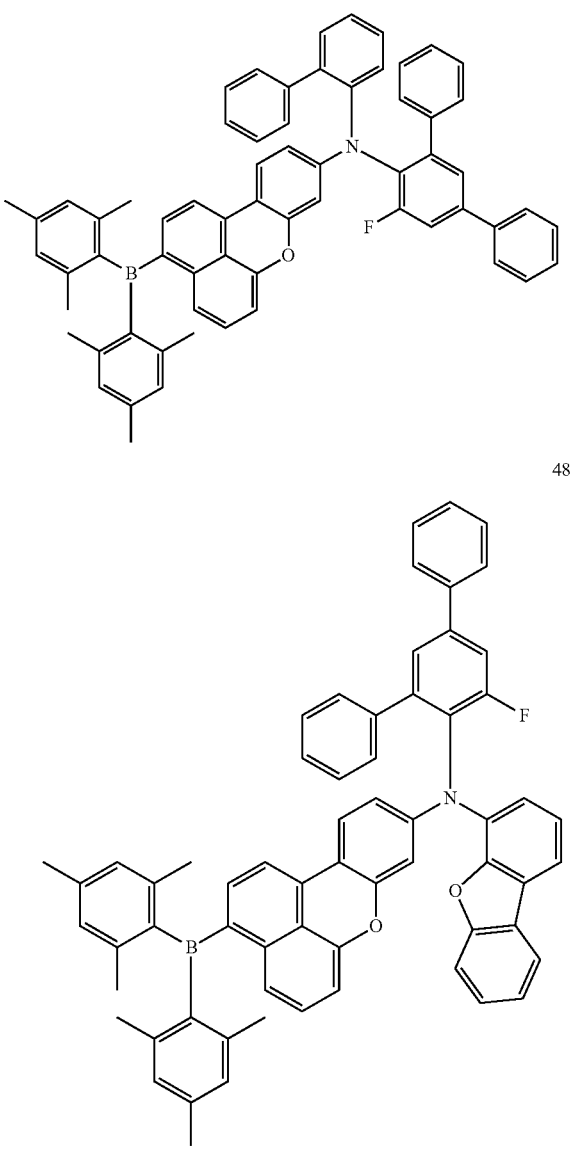
47
48
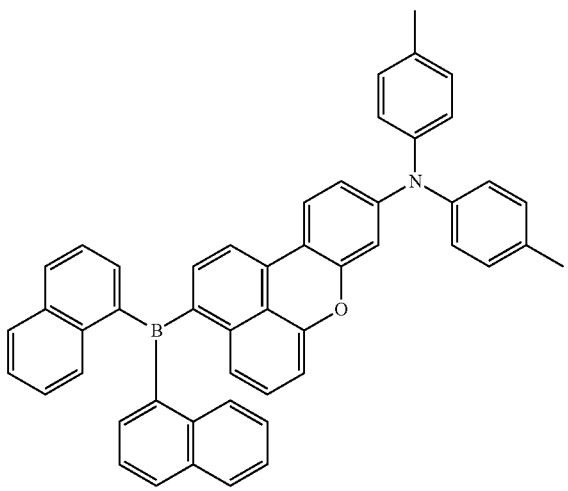
49
50
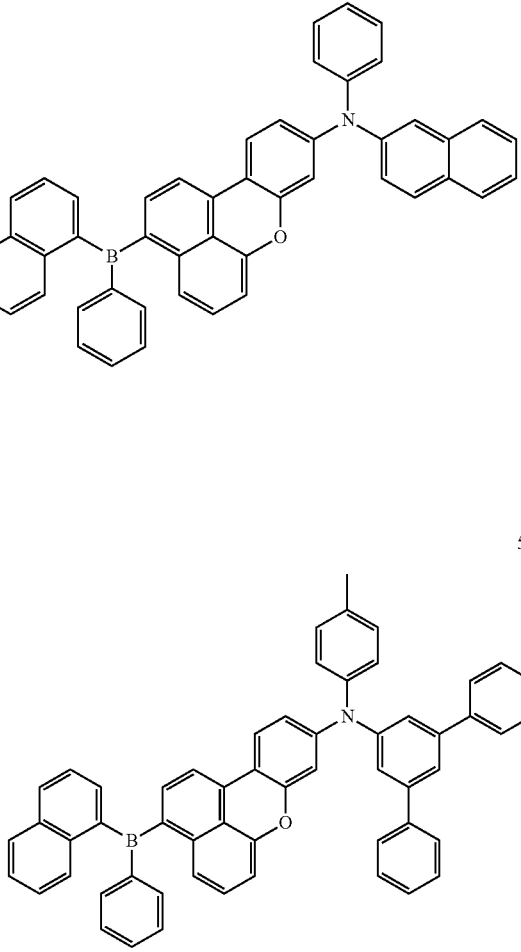
51

52
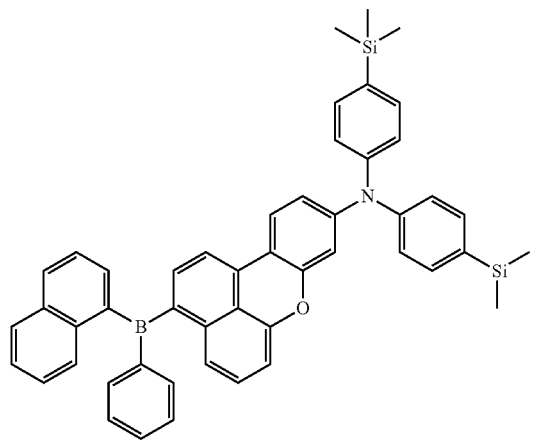
53
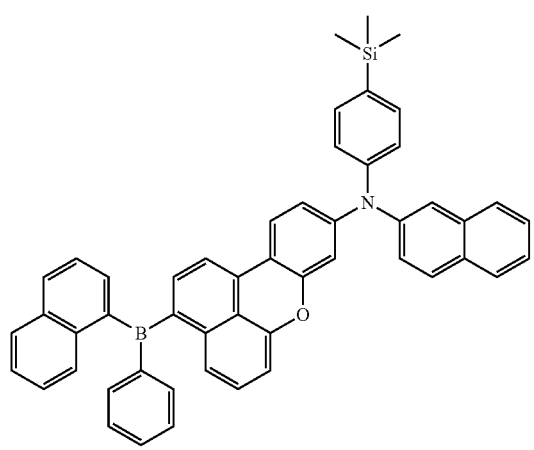
54
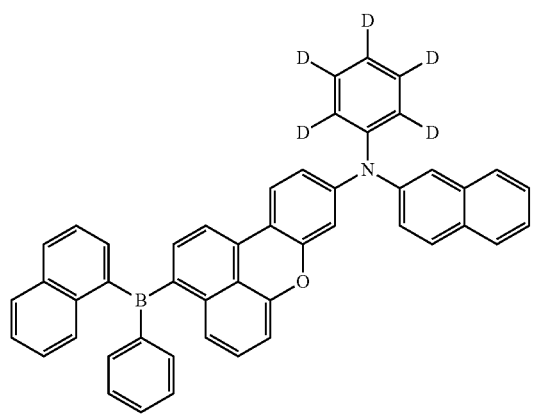
55
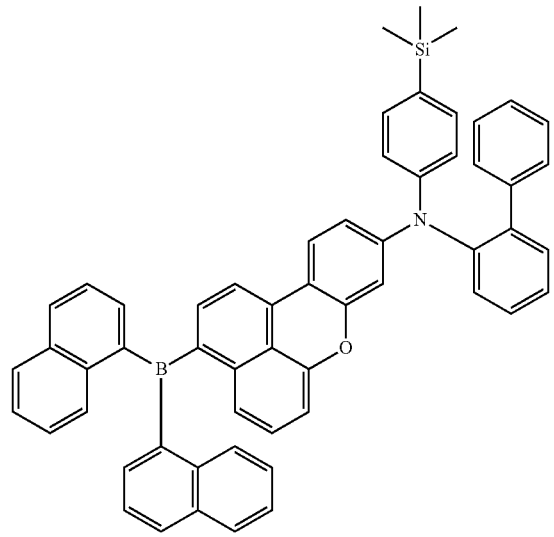
56
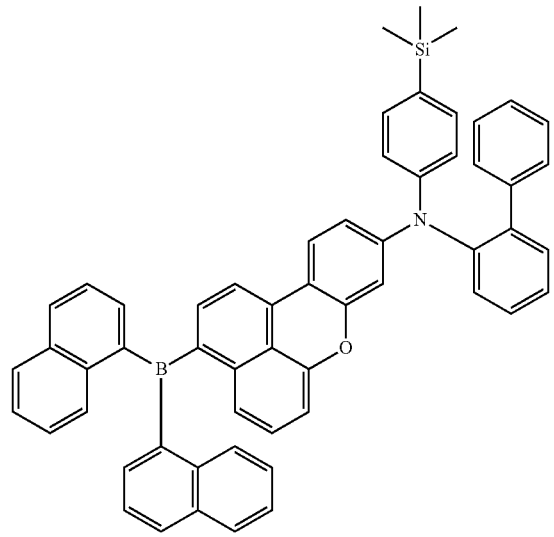
57
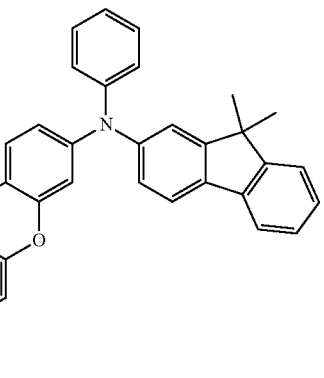

58
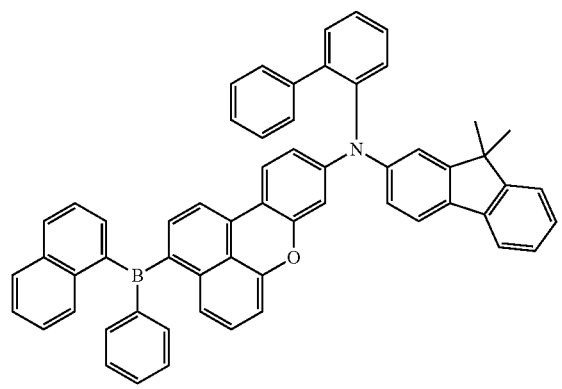
59
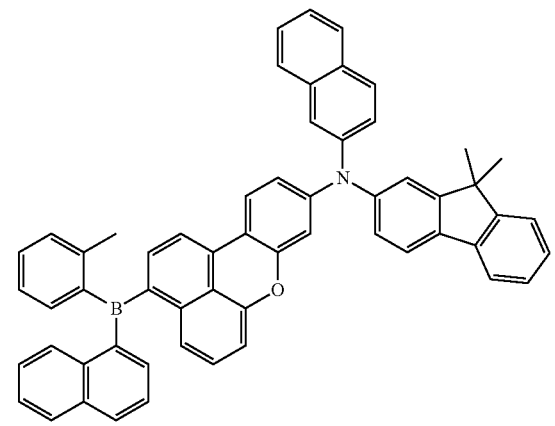
60
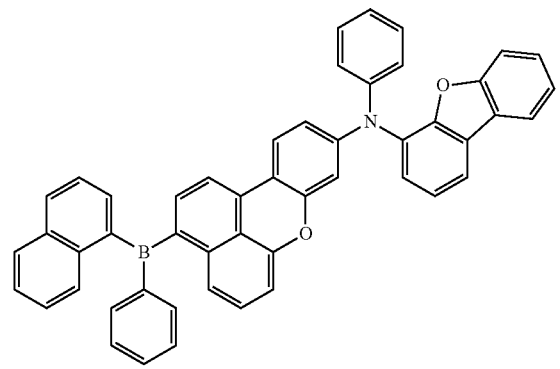
61
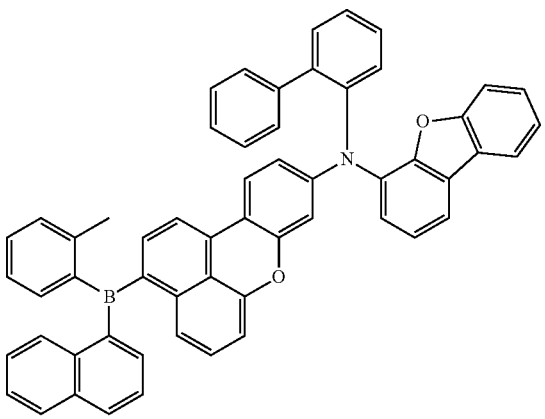
62
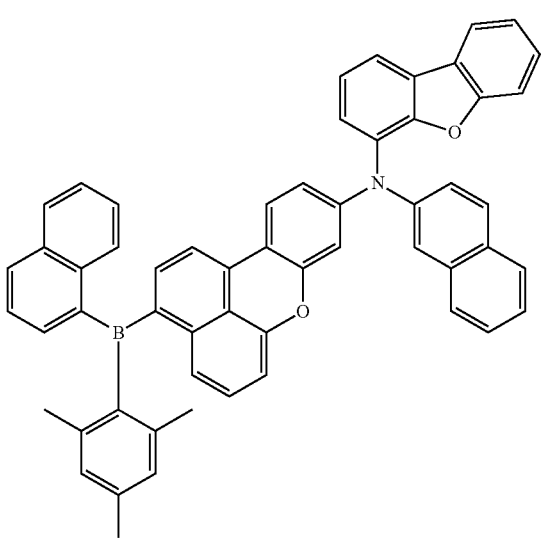
63
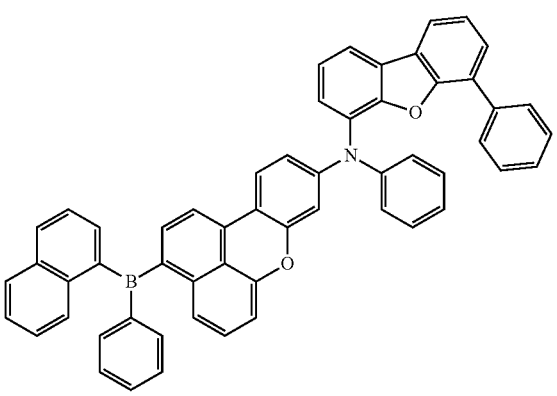

201
-continued
64
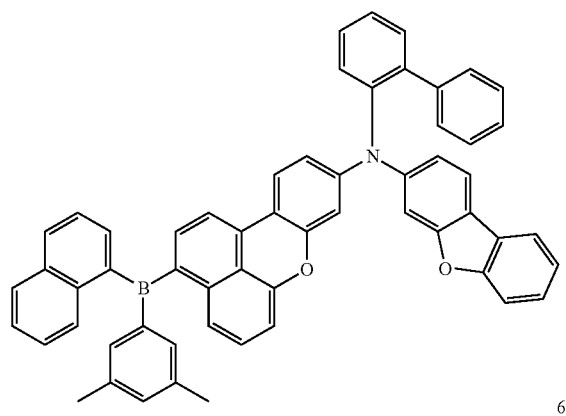
65
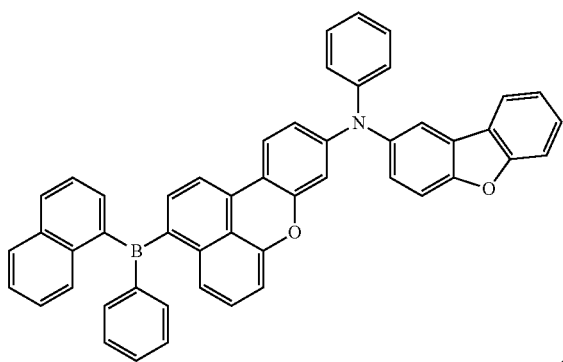
66
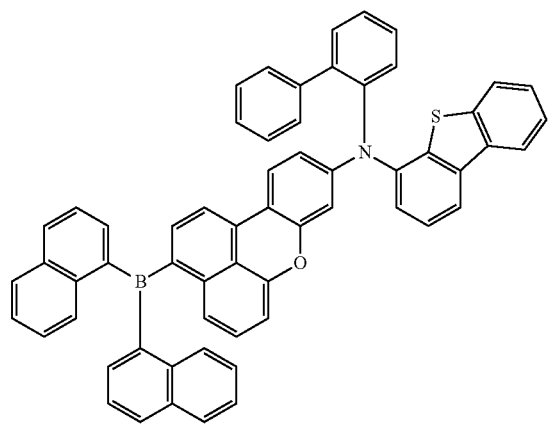
67
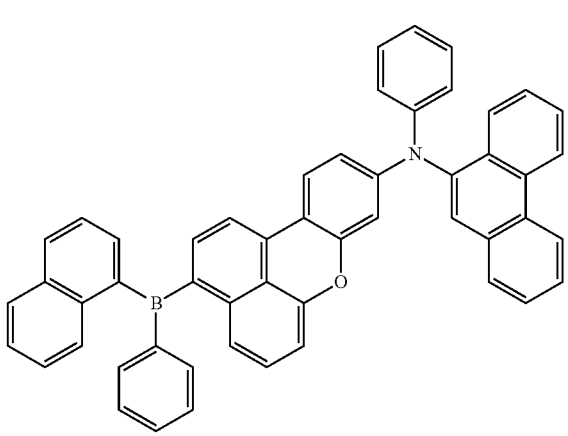
202
-continued
68
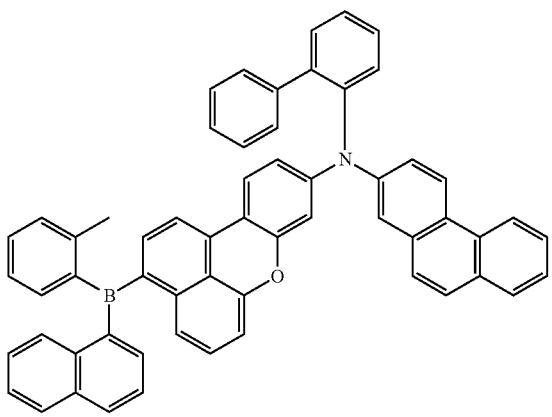
69
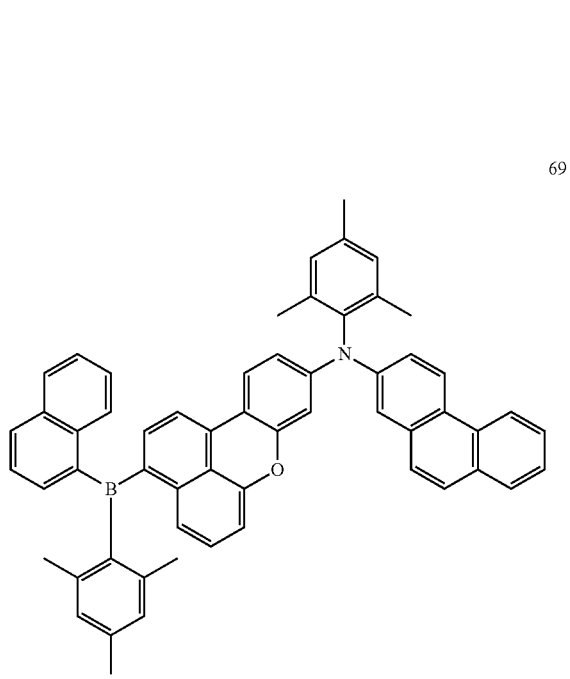
70
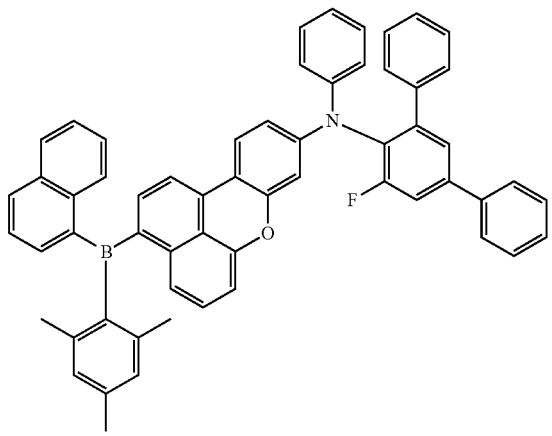

-continued
71
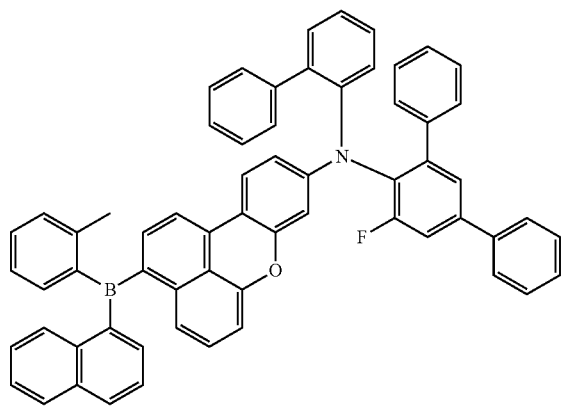
72
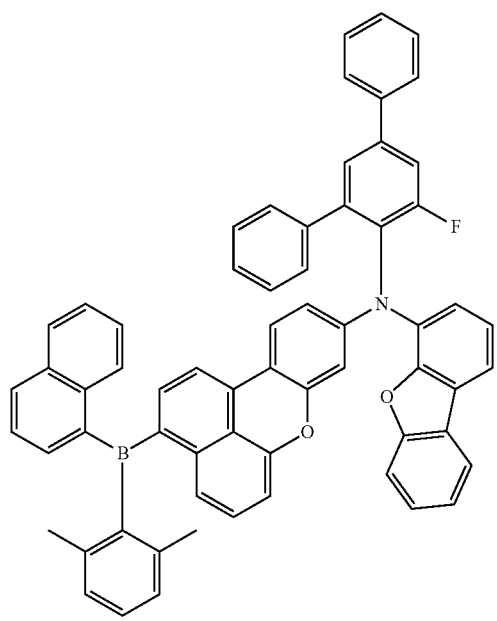
73
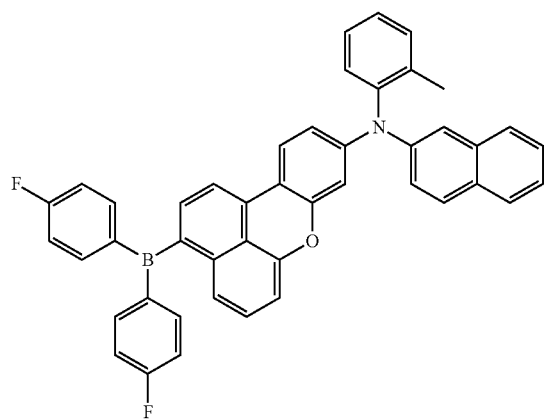
-continued
74
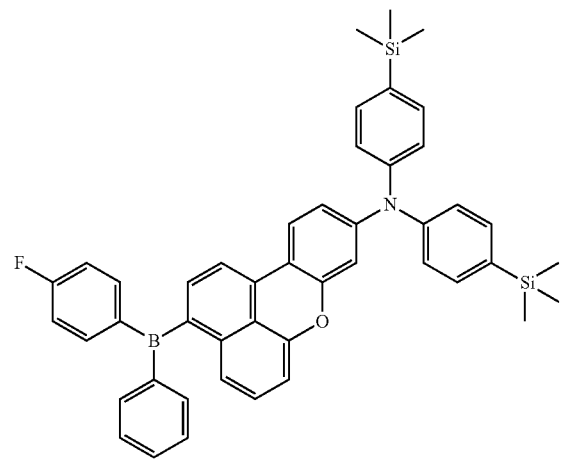
75
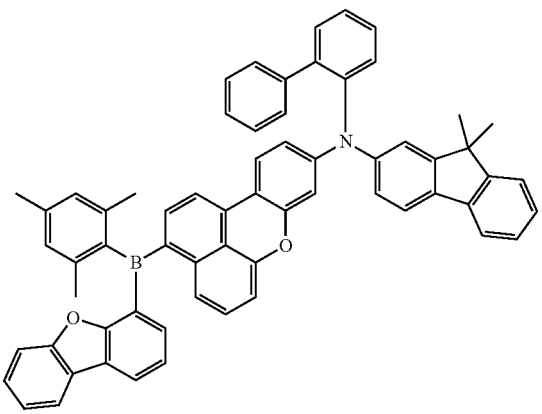
76
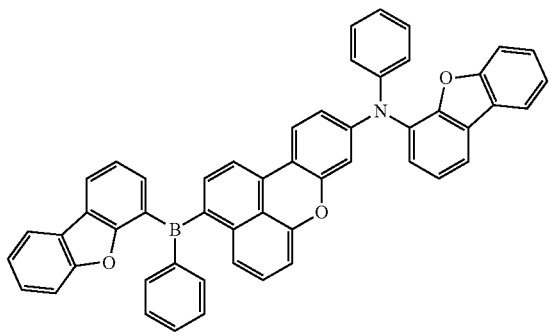

77
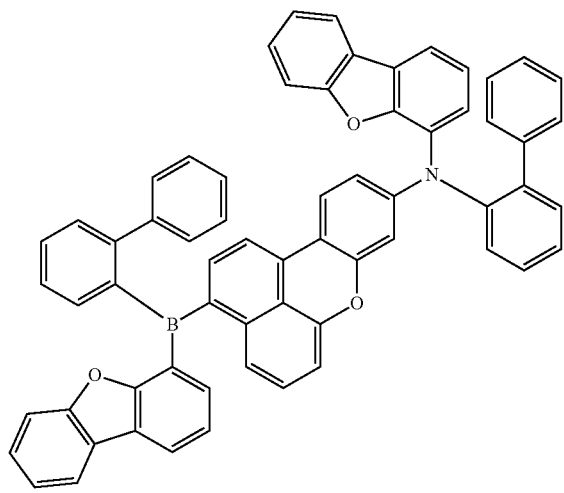
78
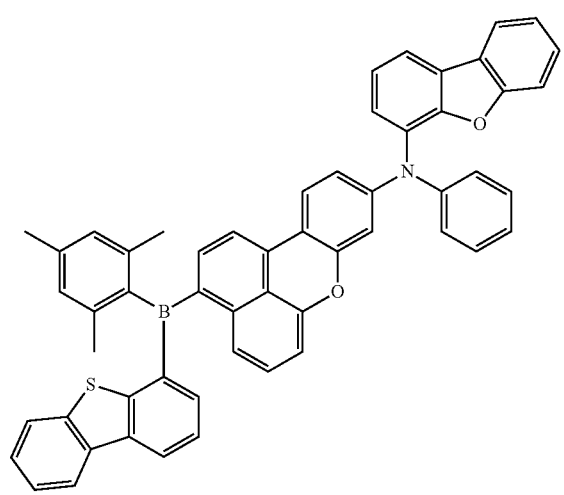
79
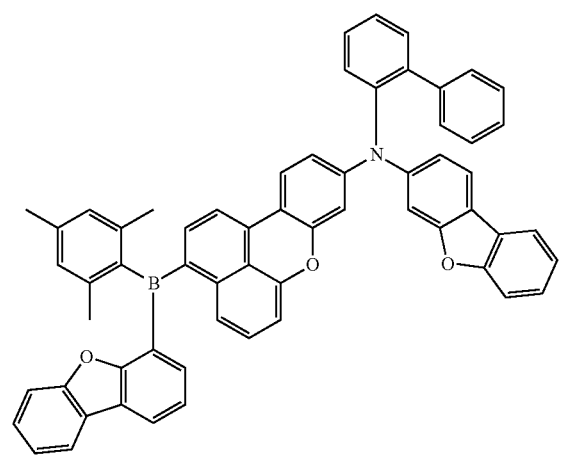
80
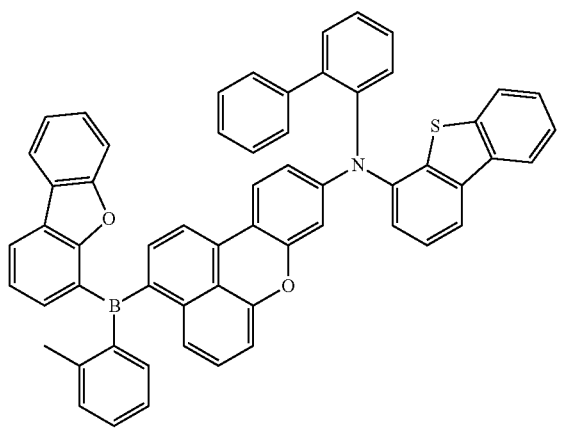
81
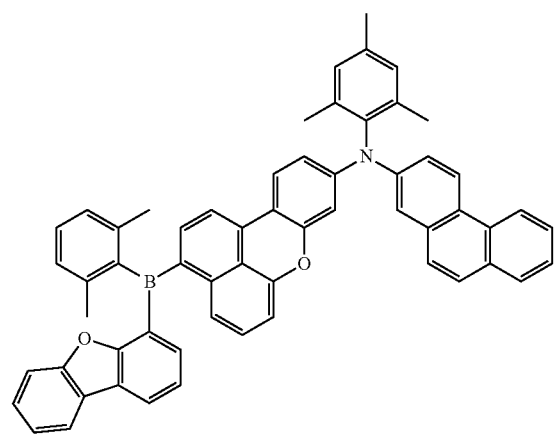
82
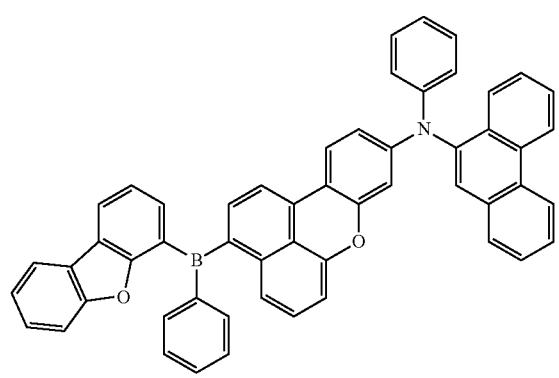

83
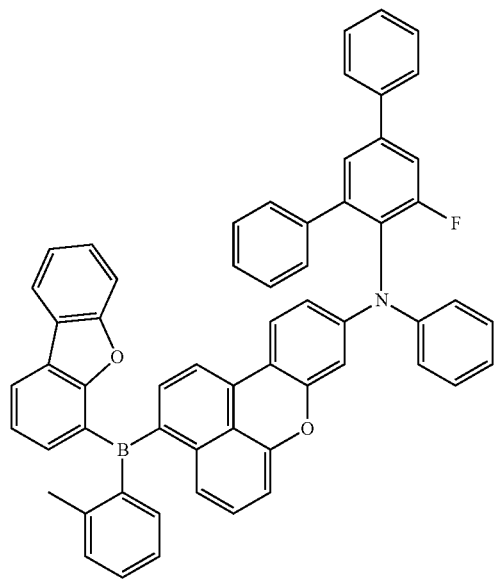
84
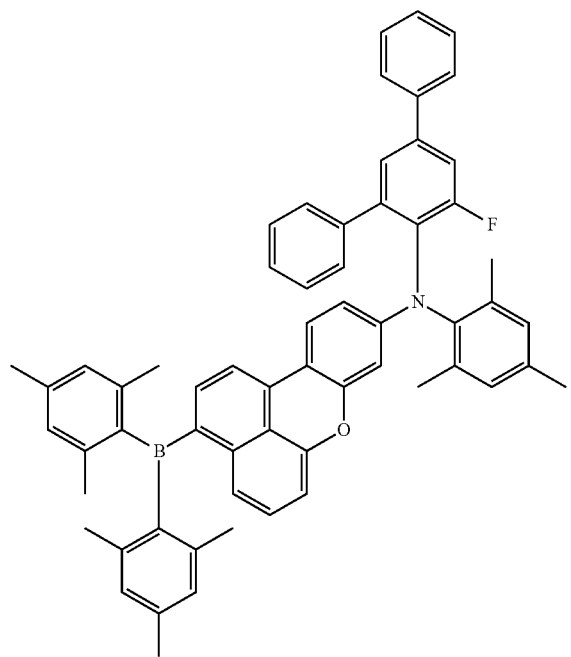
85
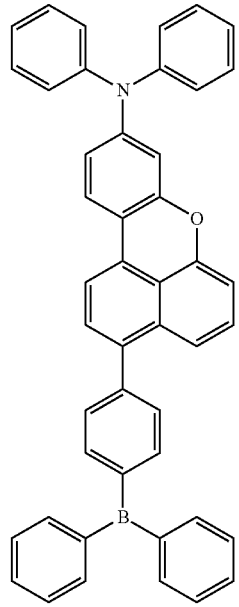
86
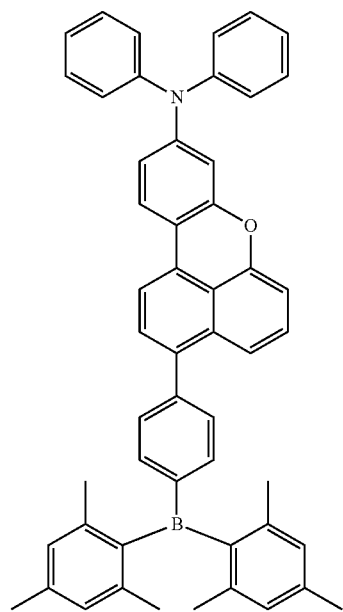

209
-continued
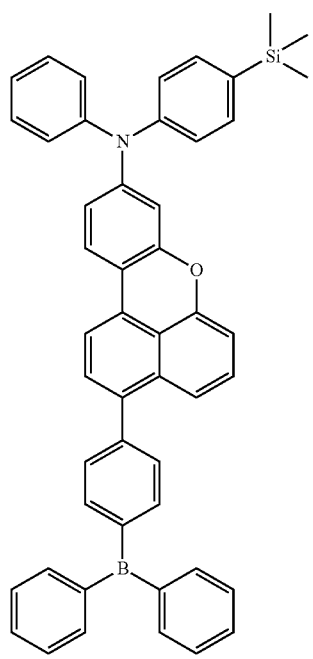
87
88
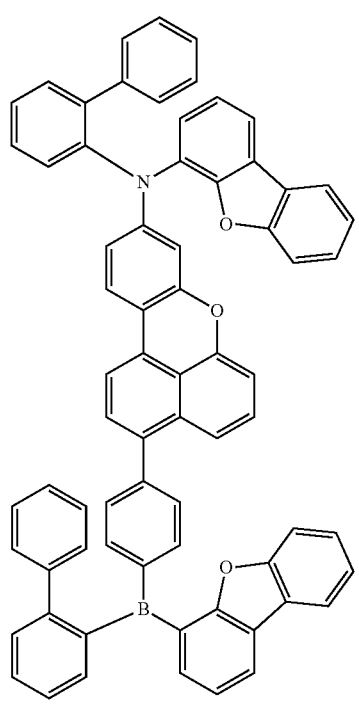
210
-continued
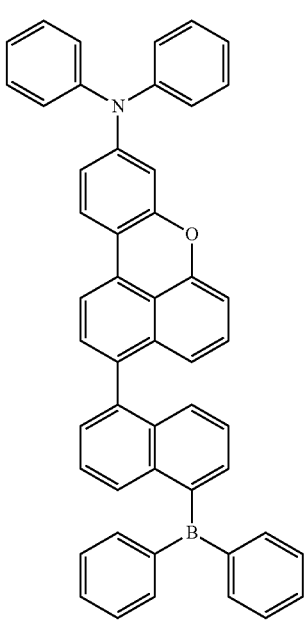
89
90
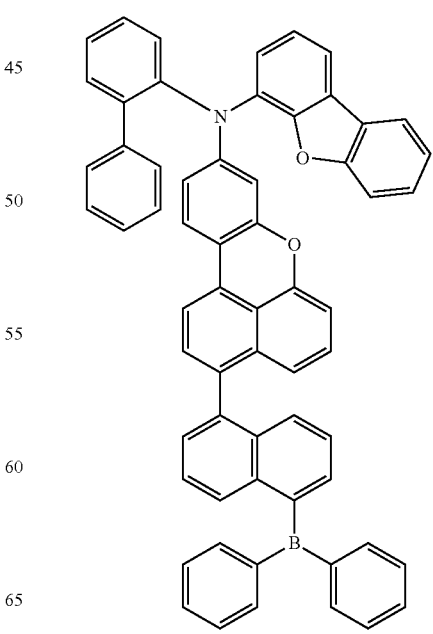

US 9,991,452 B2
211
-continued
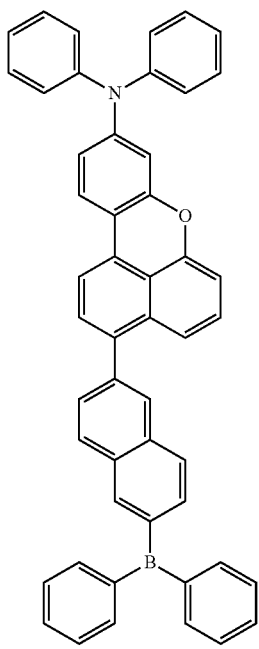
91
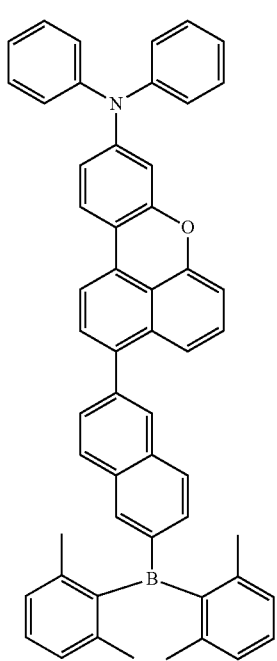
92
212
-continued
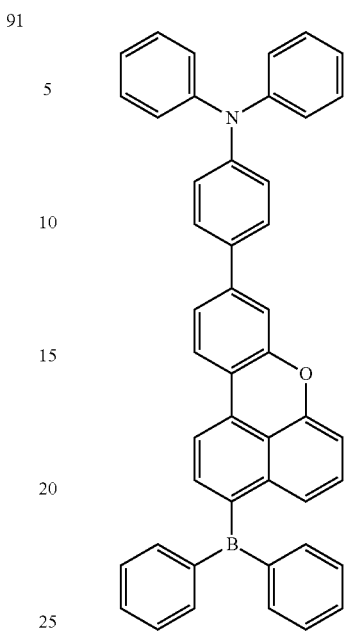
93
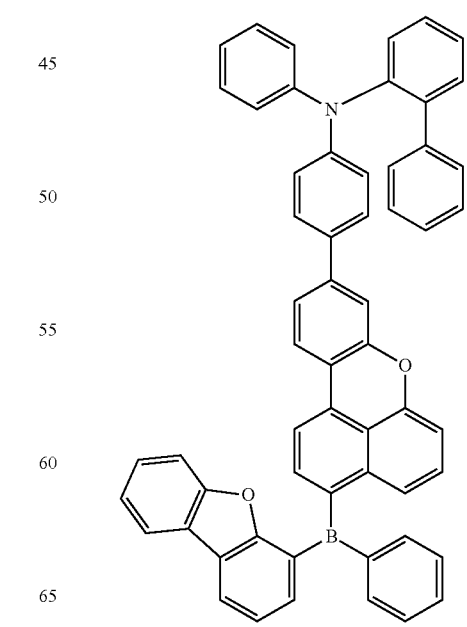
94

95
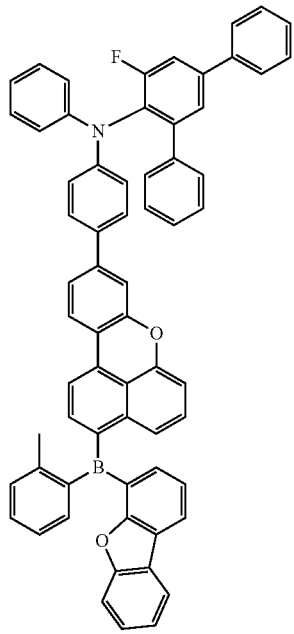
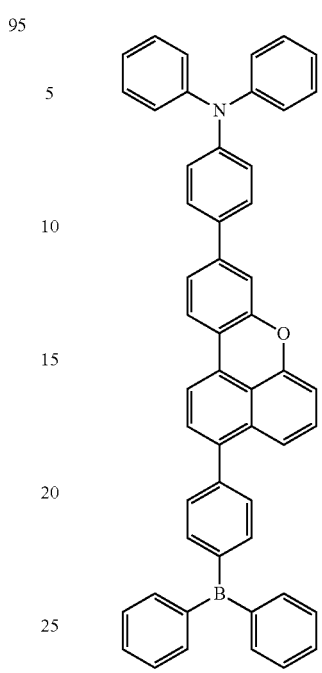
97
96
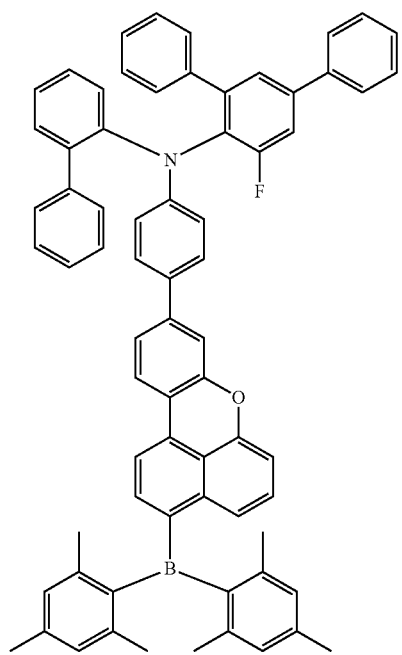
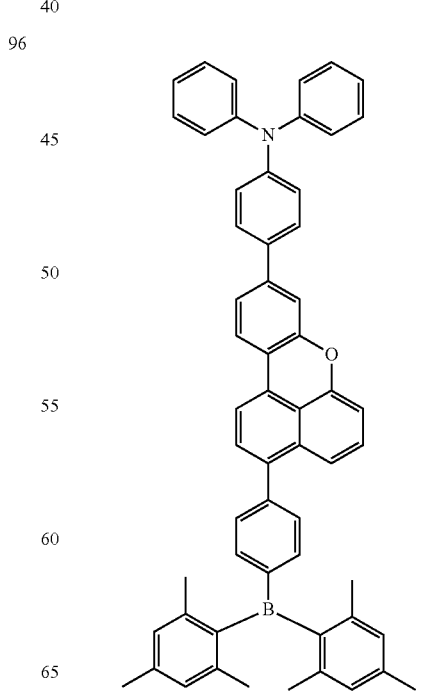
98

-continued

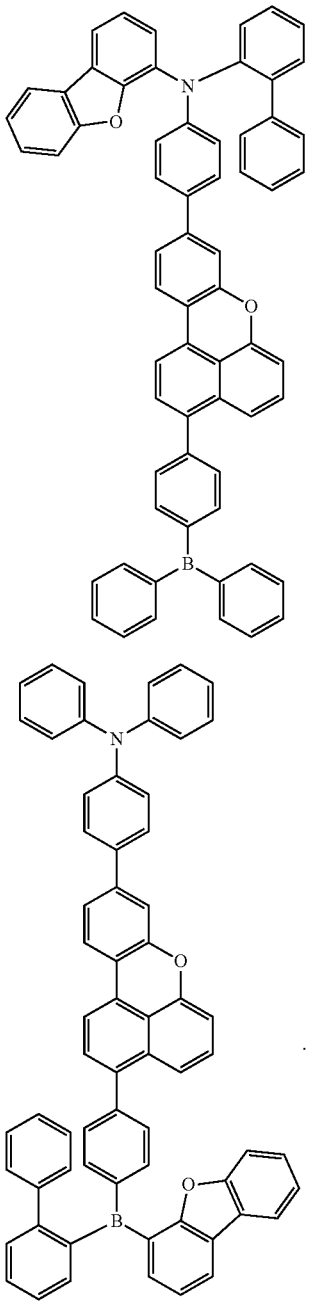

17. An organic light-emitting device, comprising
a first electrode;
a second electrode facing the first electrode; and
an organic layer between the first electrode and the second electrode, the organic layer including an emission layer, wherein the organic layer includes at least one type of the condensed-cyclic compound as claimed in claim 1.

18. The organic light-emitting device as claimed in claim 17, wherein
the first electrode is an anode,
the second electrode is a cathode,
the organic layer includes i) a hole transport region between the first electrode and the emission layer, the hole transport region including at least one of a hole injection layer, a hole transport layer, a buffer layer, and an electron blocking layer, and ii) an electron transport region between the emission layer and the second electrode, the electron transport region at least one of a hole blocking layer, an electron transport layer, and an electron injection layer.

19. The organic light-emitting device as claimed in claim 17, wherein the emission layer includes the condensed-cyclic compound.

20. The organic light-emitting device as claimed in claim 19, wherein the emission layer further includes a compound represented by Formula 301:

$$Ar_{301}-[(L_{301})_{xb1}-R_{301}]_{xb2}$$ <Formula 301> wherein, in Formula 301,
$Ar_{301}$ is one of:
a naphthalene, a heptalene, a fluorene, a Spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene; and
a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of:
a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$),
wherein $Q_{301}$ to $Q_{303}$ are each independently one of a hydrogen, a $C_1$-$C_{60}$ alkyl group, a $C_2$-$C_{60}$ alkenyl group, a $C_6$-$C_{60}$ aryl group, and $C_2$-$C_{60}$ heteroaryl group;
$L_{301}$ is one of a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;
$R_{301}$ is one of:
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is 0, 1, 2, or 3; and xb2 is 1, 2, 3, or 4.

* * * * *